US007741308B2

(12) United States Patent
Dutreix et al.

(10) Patent No.: US 7,741,308 B2
(45) Date of Patent: *Jun. 22, 2010

(54) DBAIT AND USES THEREOF

(75) Inventors: Marie Dutreix, L'Hay les Roses (FR); Jian-Sheng Sun, Saint Maur Des Fosses (FR)

(73) Assignees: Institut Curie, Paris Cedex (FR); Centre National de la Recherche Scientifique (CNRS), Paris Cedex (FR); Museum National d'Historie Naturelle, Paris Cedex (FR); Institut National de la Sante Et de la Recherche Medicale (INSERM), Paris Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/324,030

(22) Filed: Nov. 26, 2008

(65) Prior Publication Data

US 2009/0156541 A1 Jun. 18, 2009

Related U.S. Application Data

(60) Division of application No. 11/524,528, filed on Sep. 21, 2006, now Pat. No. 7,476,729, which is a continuation-in-part of application No. 10/576,818, filed as application No. PCT/EP2004/012857 on Oct. 25, 2004, now Pat. No. 7,595,302.

(30) Foreign Application Priority Data

Oct. 24, 2003 (EP) .................................. 03292666

(51) Int. Cl.
*A61H 31/70* (2006.01)
*C07H 21/04* (2006.01)

(52) U.S. Cl. ........................ 514/44; 536/23.1; 536/24.5
(58) Field of Classification Search ....................... None
See application file for complete search history.

(56) References Cited

U.S. PATENT DOCUMENTS

| 7,060,690 B2 | 6/2006 | Klem |
| 2003/0176376 A1 | 9/2003 | Klem |
| 2007/0111961 A1 | 5/2007 | Dutreix et al. |
| 2007/0197458 A1 | 8/2007 | Dutreix et al. |

FOREIGN PATENT DOCUMENTS

| EP | 0 978 561 A1 | 2/2000 |
| WO | WO 94/01550 A1 | 1/1994 |
| WO | WO 03/069306 A2 | 8/2003 |
| WO | WO 03/070914 A2 | 8/2003 |

OTHER PUBLICATIONS

International Search Report of PCT/EP2004/012857, mailed Mar. 4, 2005.
Partial European Search Report of EP 03 29 2666, completed May 14, 2004.
Omori et al., "Suppression of a DNA doublepstrand break repair gene, *Ku70*, increases radio- and chemosensitivity in a human lung carcinoma cell line", DNA Repair, pp. 299-310.
Ohnishi et al., "In vitro and in vivo potentiation of radiosensitivity of malignant gliomas by antisense inhibition of the RAD51 gene", Biochemical and Biophysical Research Communications, vol. 245, No. 2, 1998, pp. 319-324.
Verrelle et al., "Modulation de la reponse cellulaire aux radiations ionisantes: vers de nouvelles cibles moleculaires?", Cancer/Radiother, vol. 1, 1997, pp. 484-493.
Li et al, "Role of the non-homologous DNA end joining pathway in the early steps of retroviral infection", The EMBO Journal 2001, vol. 20, No. 12, pp. 3272-3281.
Jackson et al, "Sensing and repairing DNA double-strand breaks", Carcinogenesis 2002, vol. 23, pp. 687-696.
Marthinet et al, "Modulation of the typical multidrug resistance henotype by targeting the MED-1 region of human MDR1 promoter", Gene Therapy (2000) 7, 1224-1233.
Opalinska et al, "Nucleic-Acid Therapeutics: Basic Principles and Recent Applications", Nature Reviews, vol. 1, Jul. 2002, pp. 503-514.

*Primary Examiner*—Tracy Vivlemore
(74) *Attorney, Agent, or Firm*—Nixon & Vanderhye P.C.

(57) ABSTRACT

The invention relates to compositions and methods for interfering with the DNA repair of double strand breaks (DSBs). The invention discloses novel double-stranded nucleic acid molecules. that act as baits and hijack the holocomplex of enzymes responsible of DNA DSB sensing, signaling and/or repair pathways, in particular the non homologous end joining (NHEJ) pathway of DSB repair.

The invention discloses the use of these molecules as adjuvant compositions to be used in association with a DNA breaking treatment, particularly radiotherapy or chemotherapy, in combination with a pharmaceutically acceptable carrier, in an efficient amount to be introduced in the tumor cell nuclei in order to neutralize transiently their DNA repair capacity and trigger their death.

23 Claims, 24 Drawing Sheets

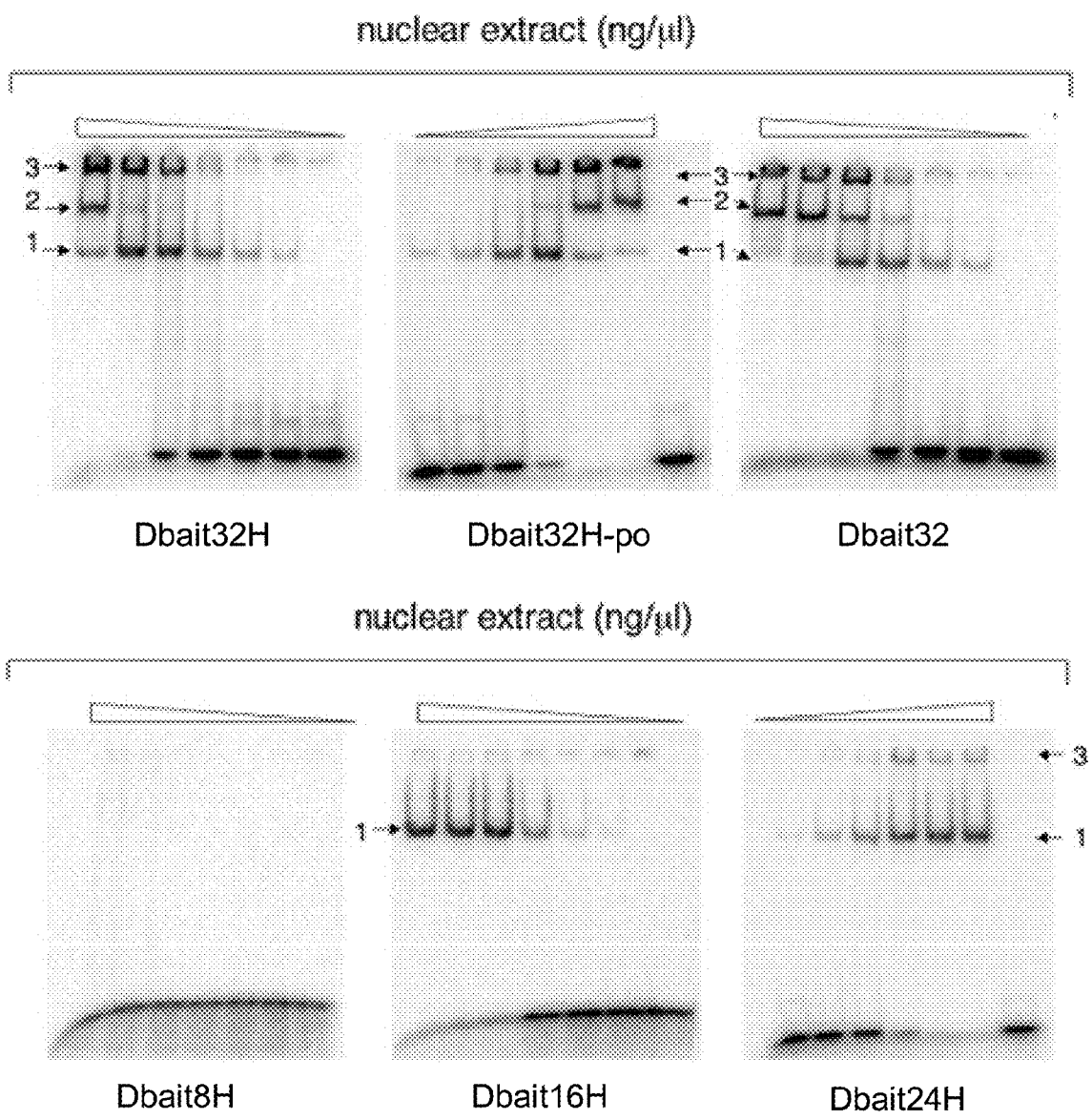
Figure 1.1

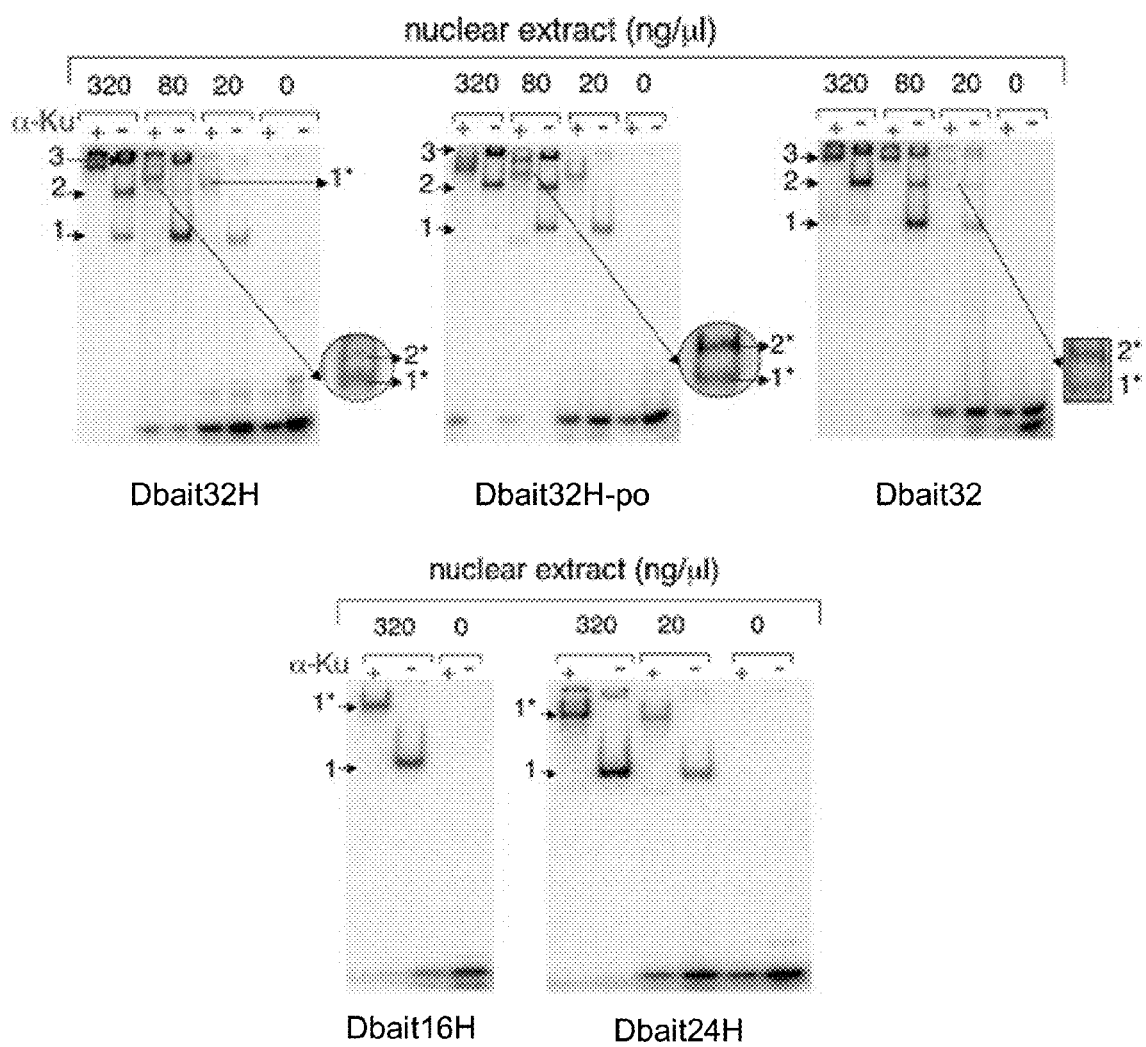
Figure 1.2

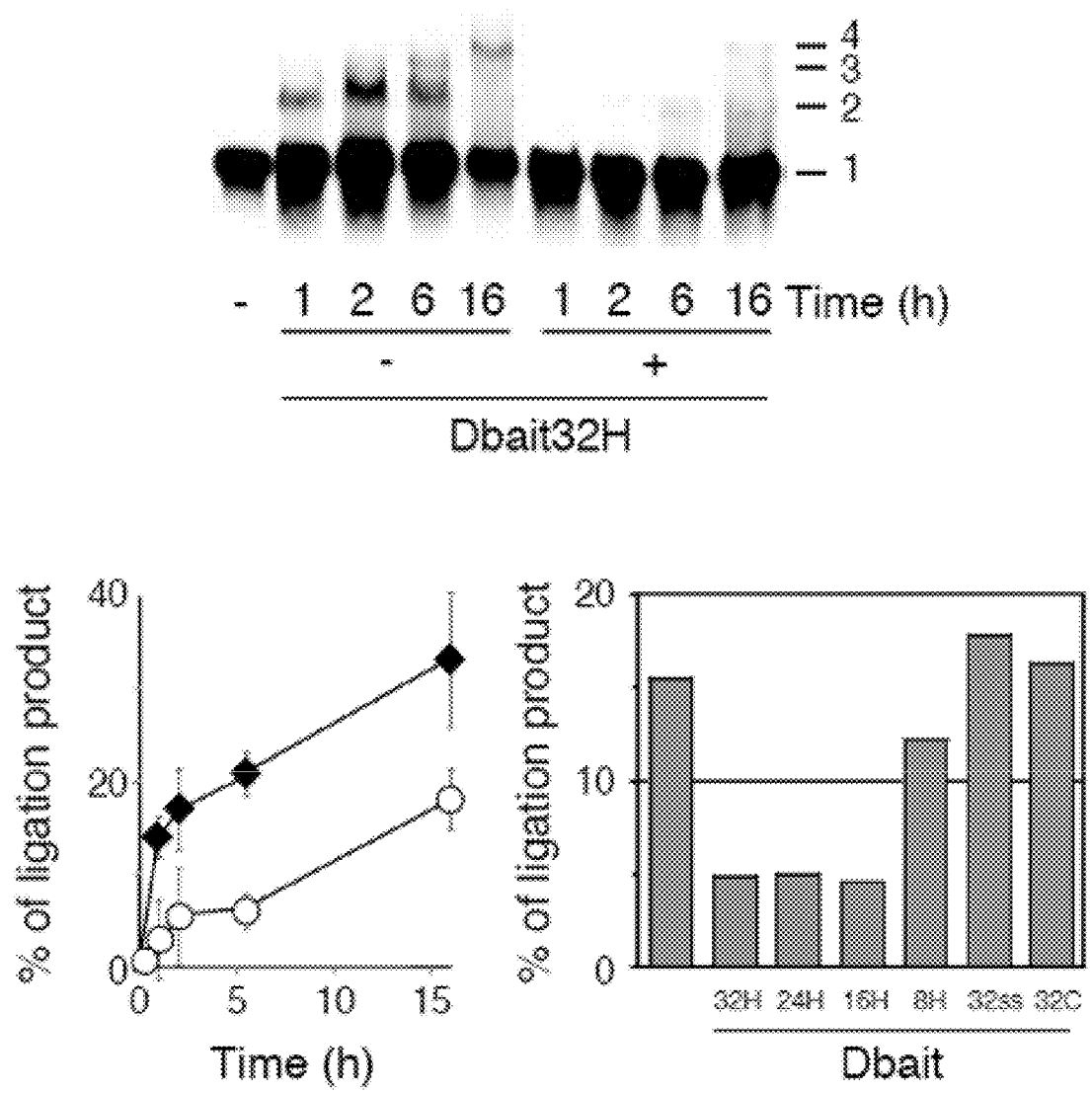
Figure 1.3

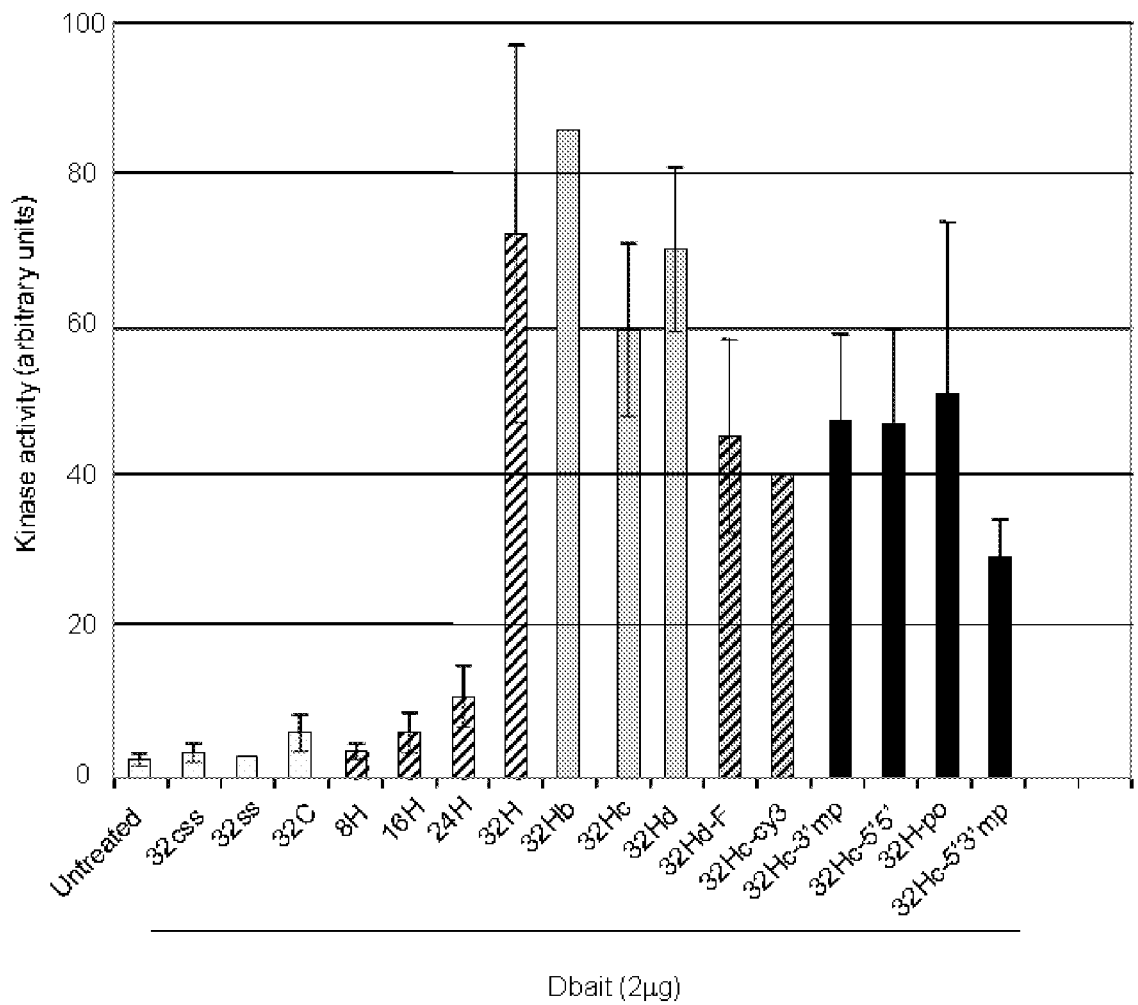
Figure 1.4

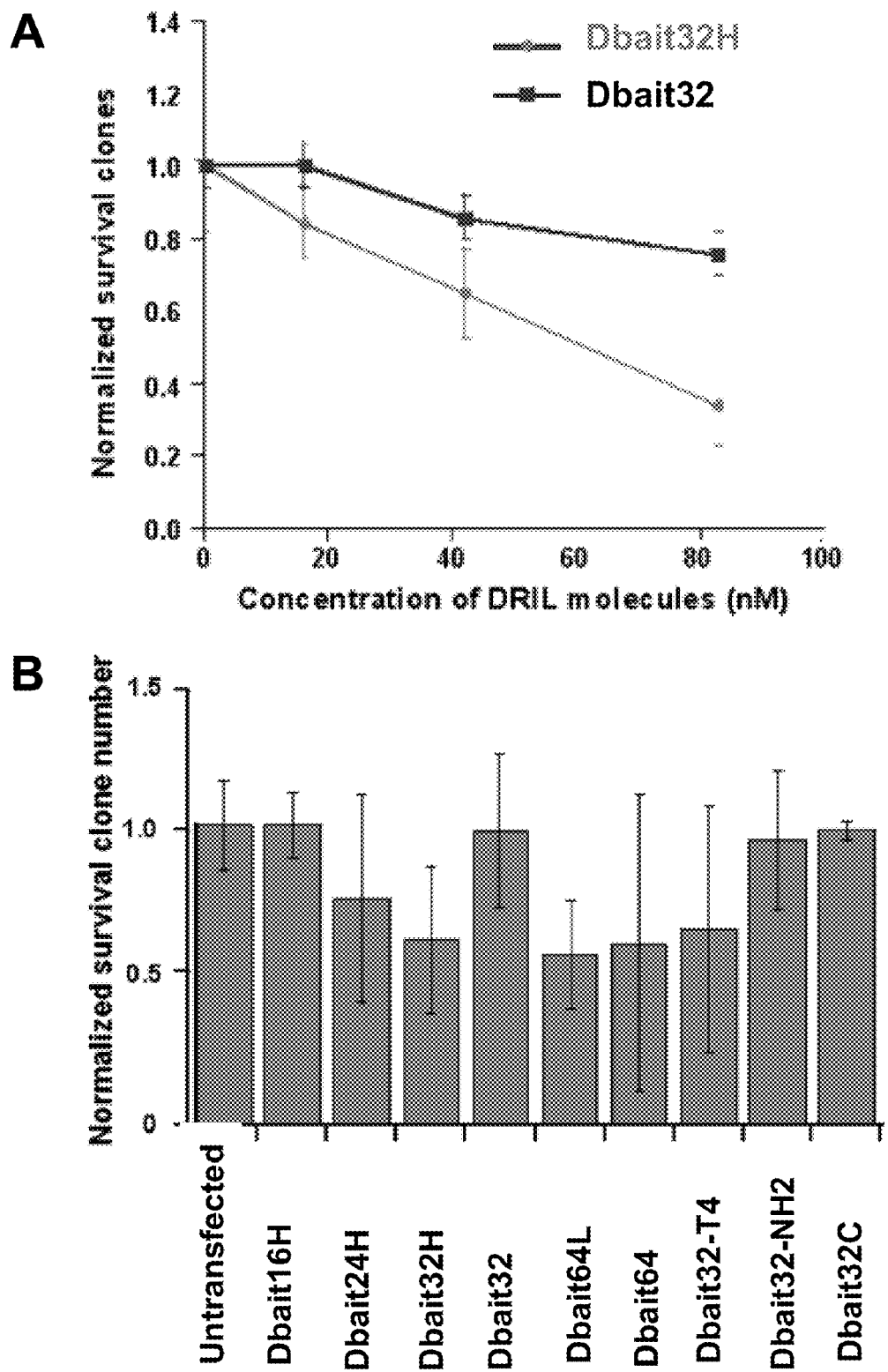
Figure 2.1

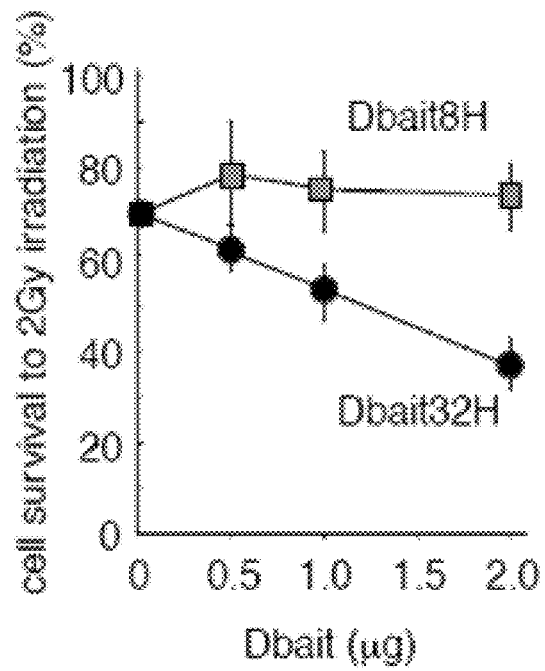
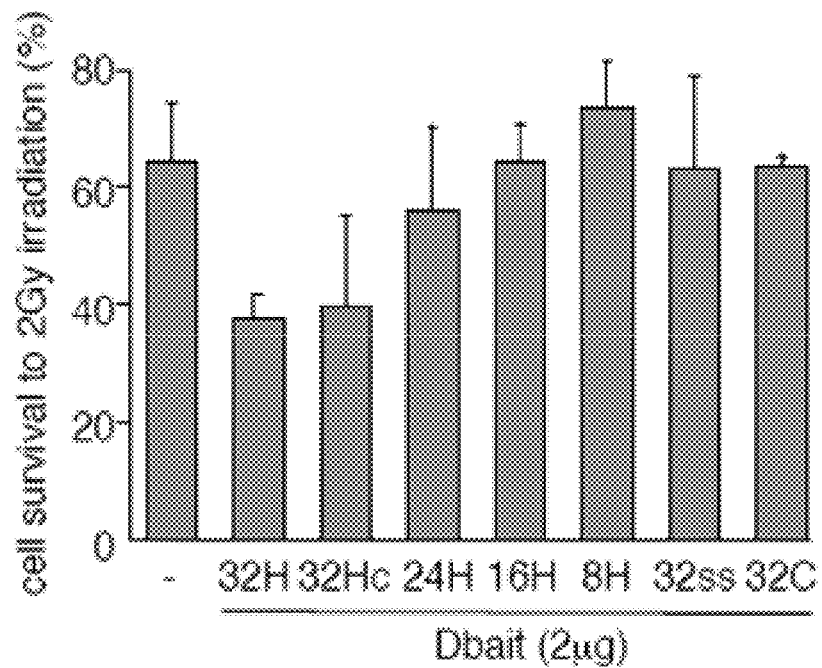
Figure 2.2

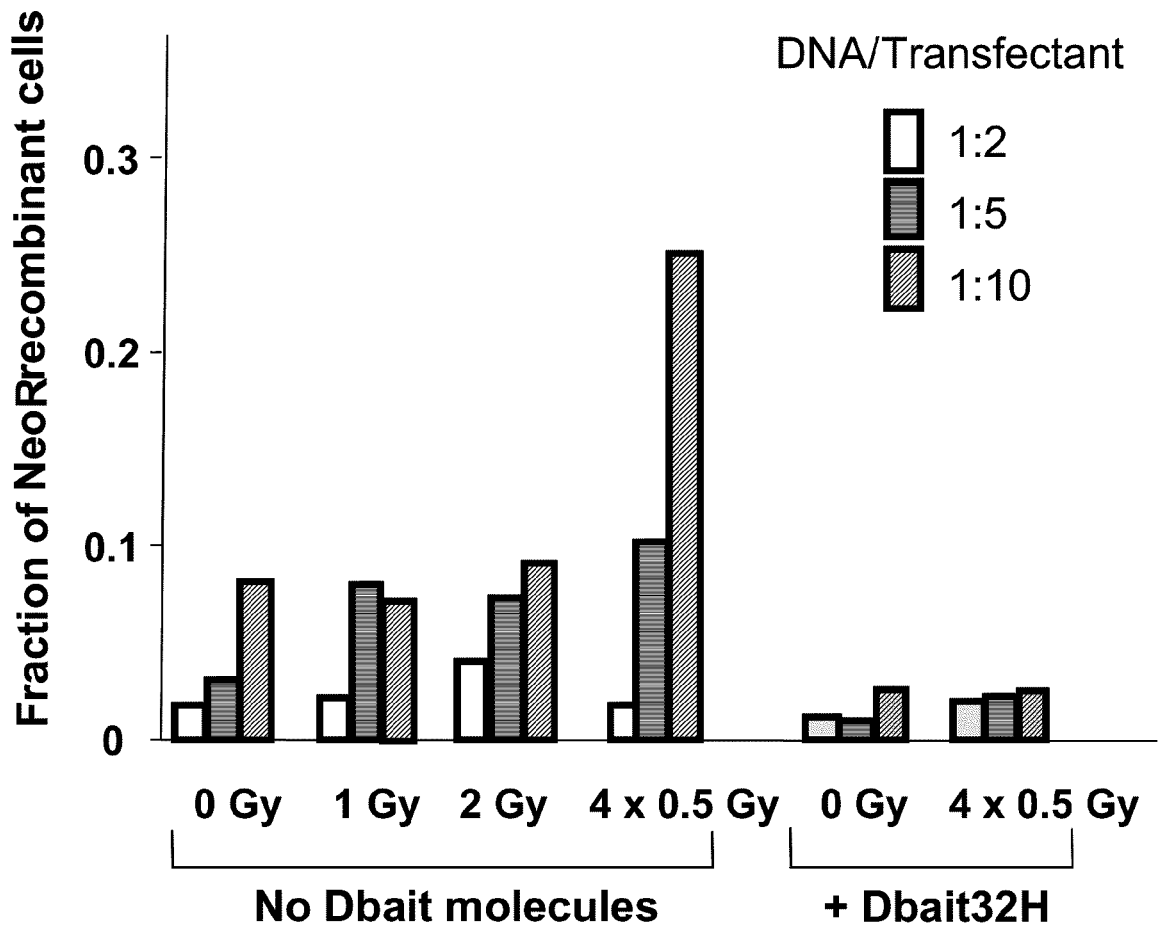
Figure 2.3

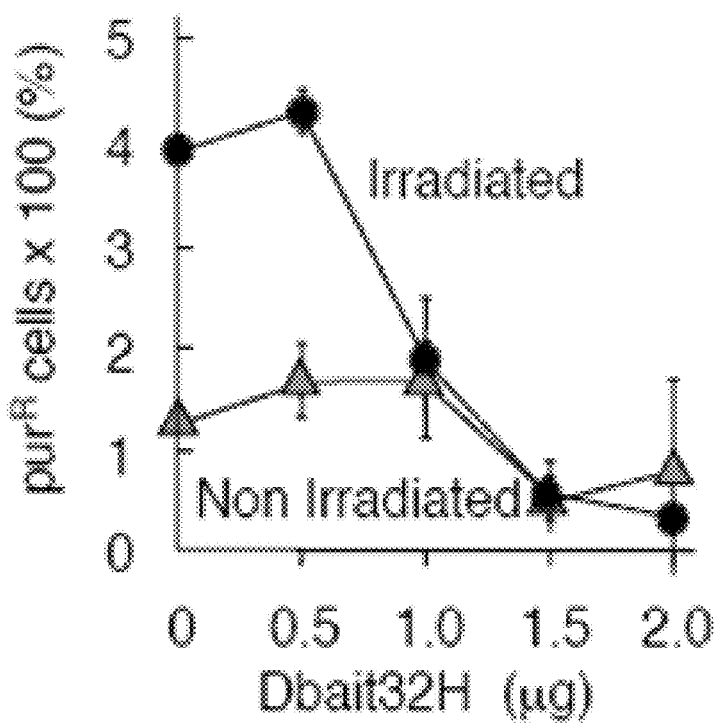
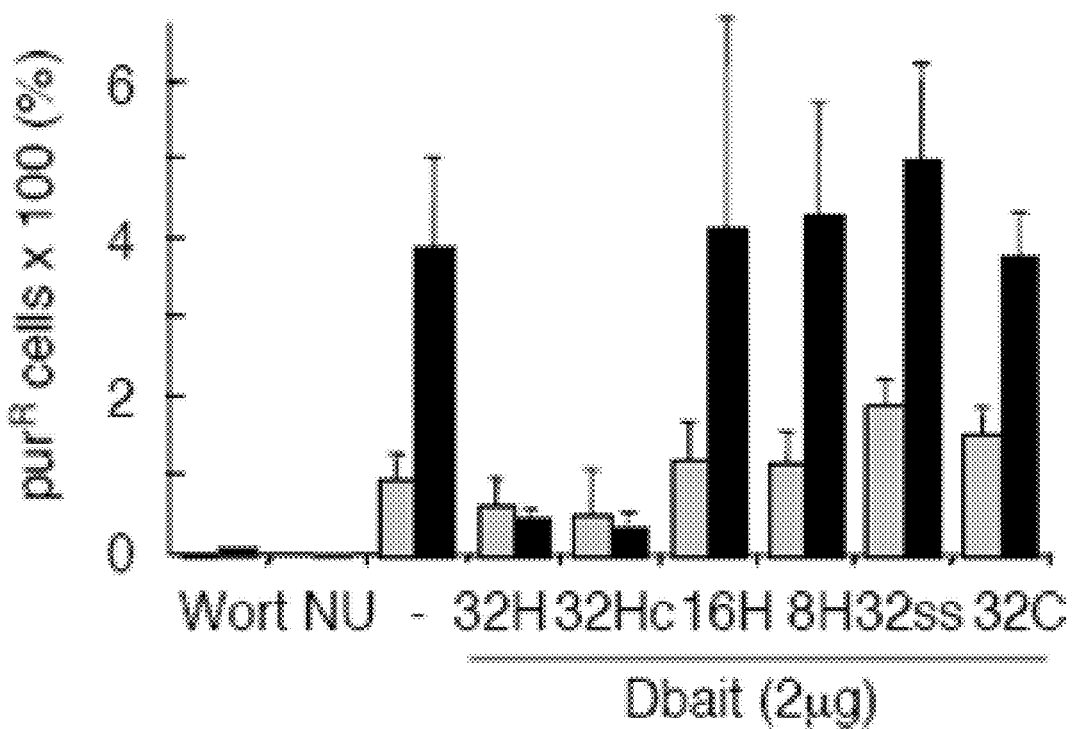
Figure 2.4

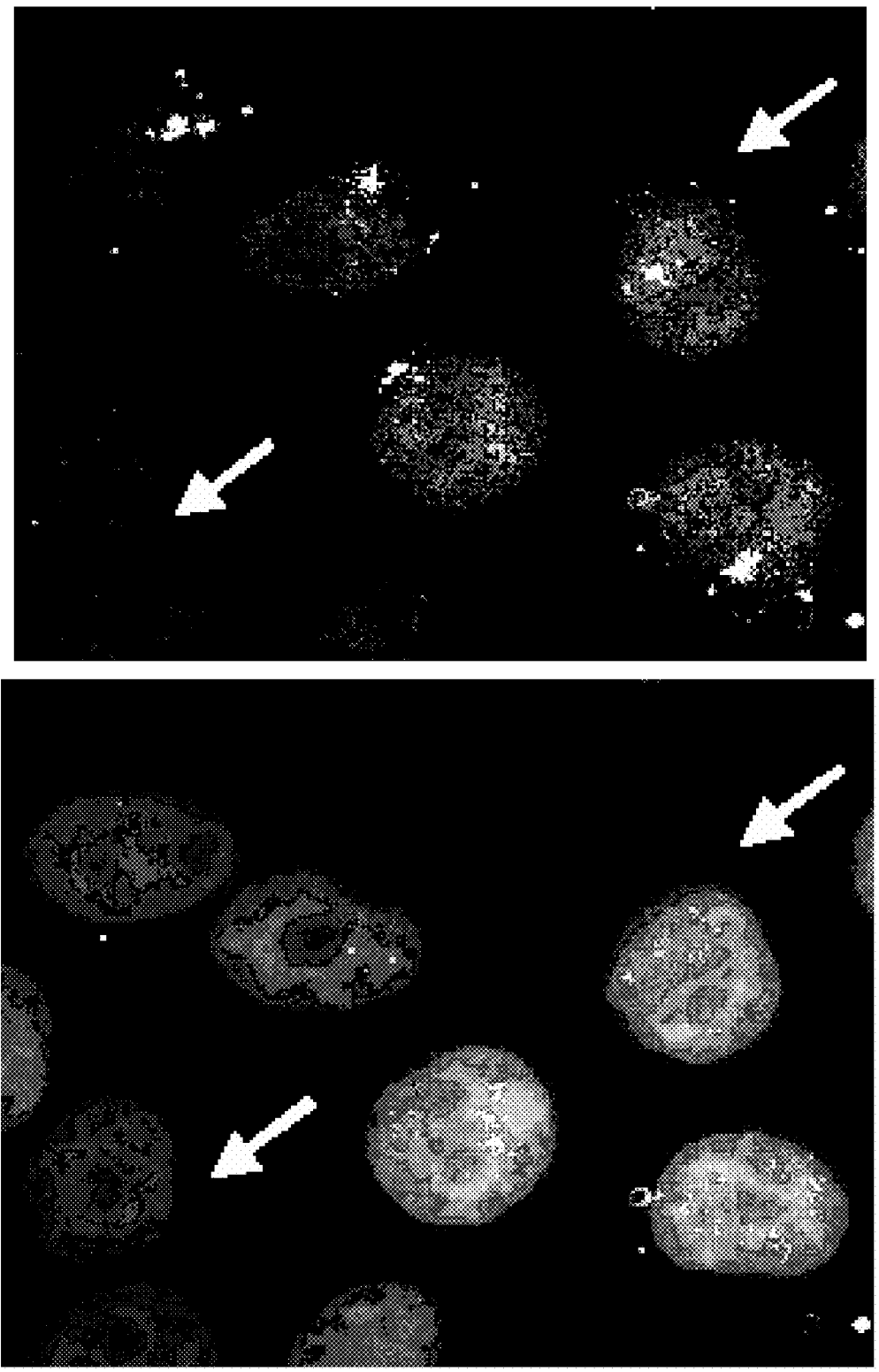
Figure 2.5

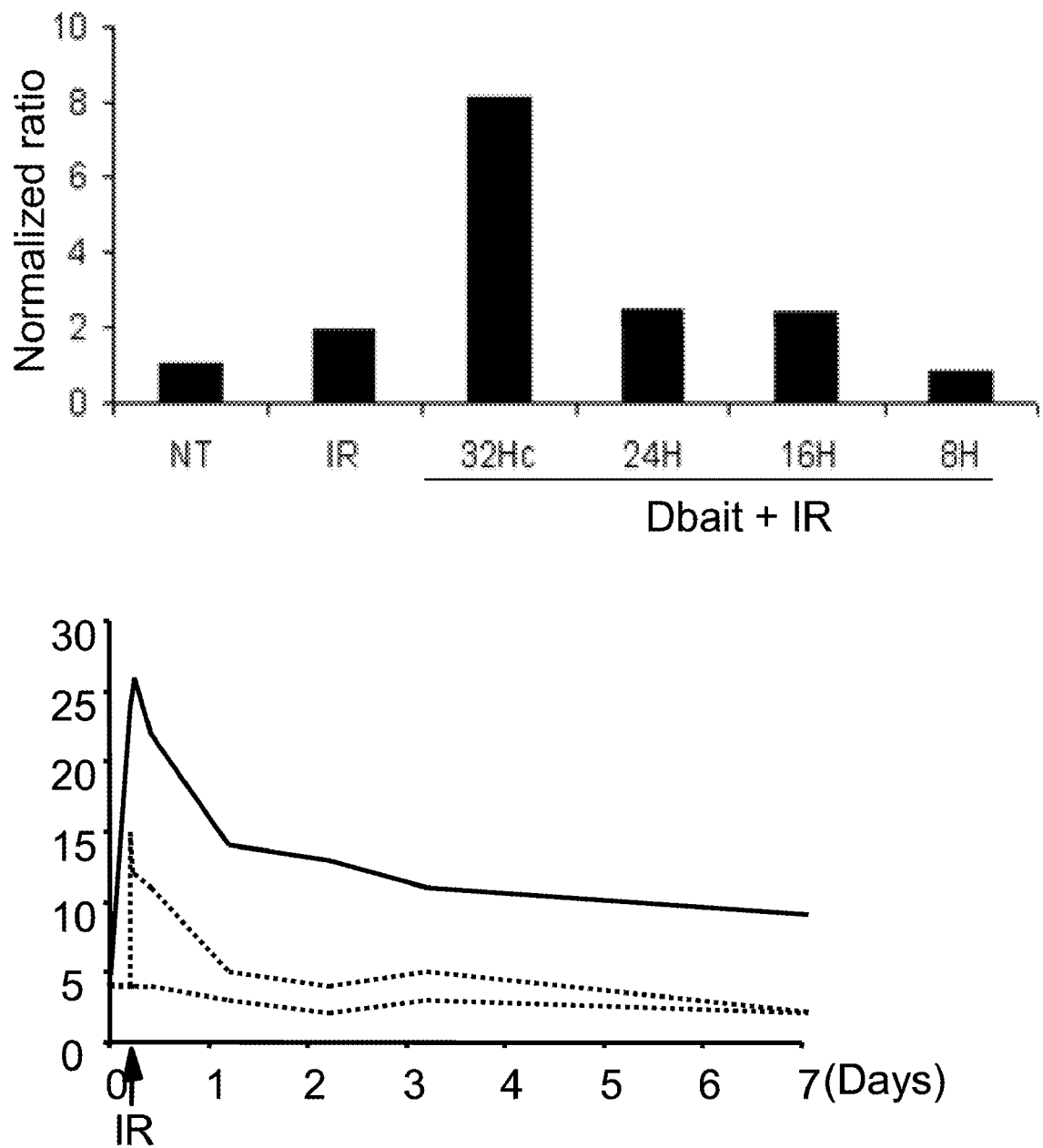
Figure 2.6

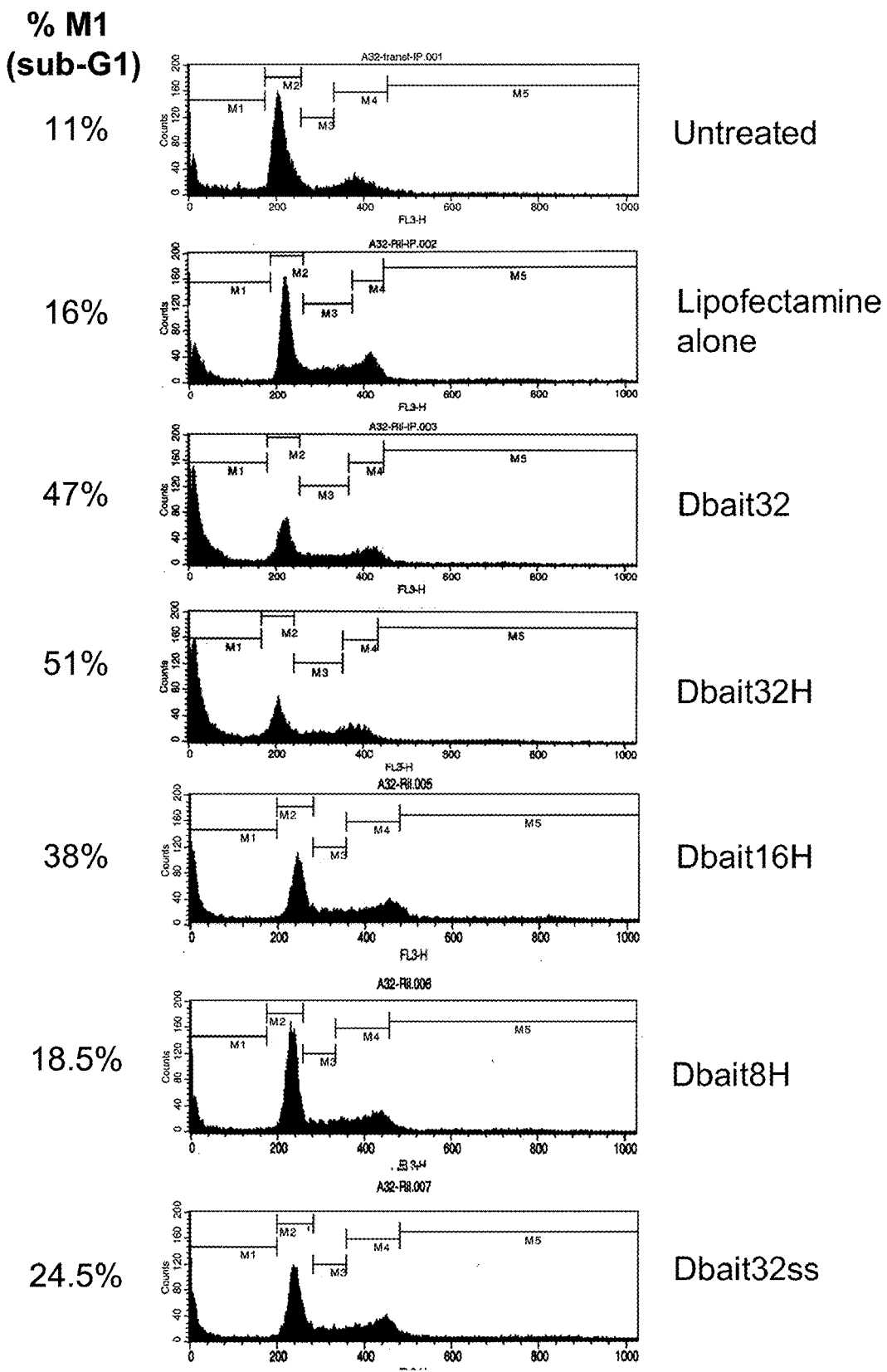
Figure 3.1

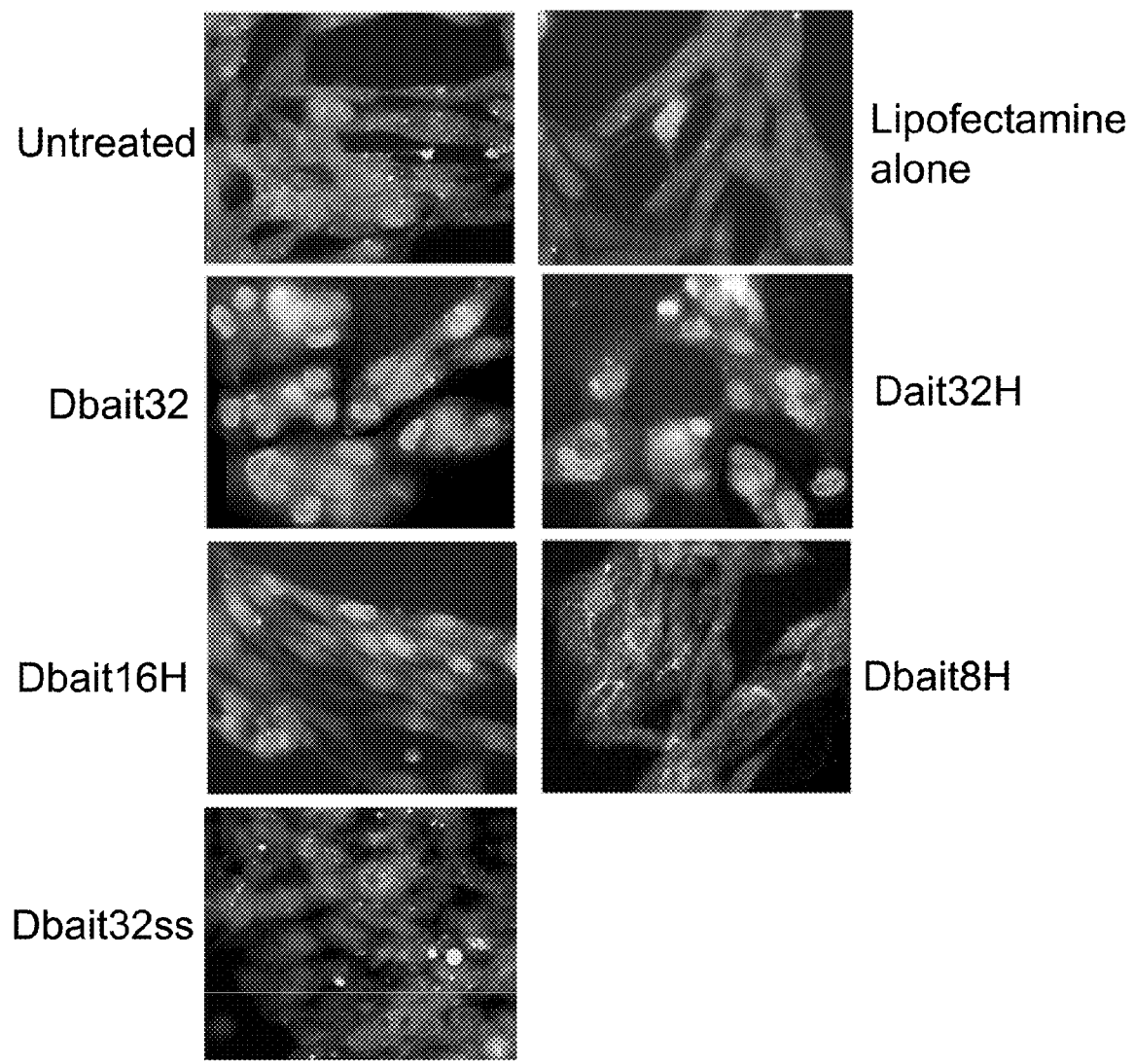
Figure 3.2

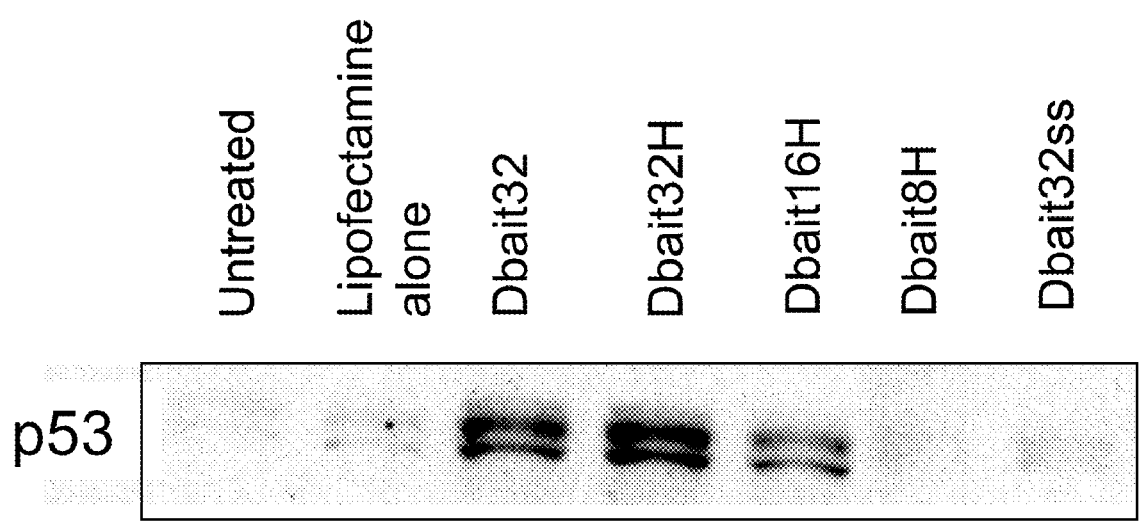
Figure 3.3

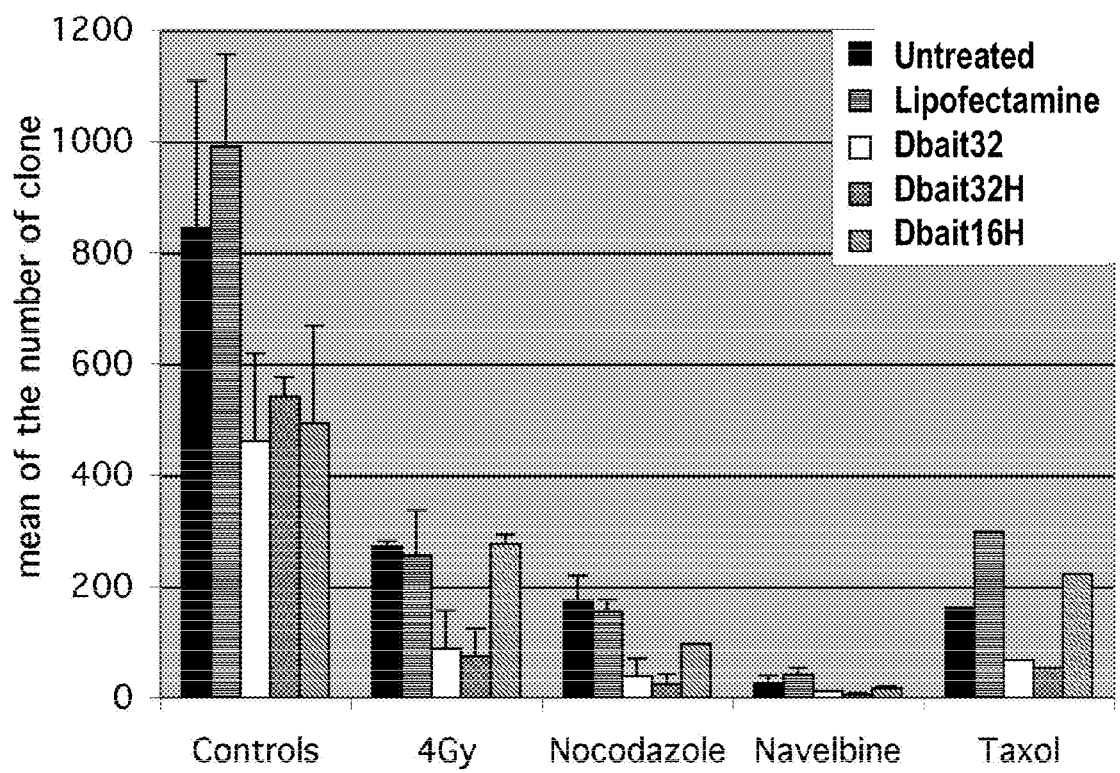
Figure 3.4

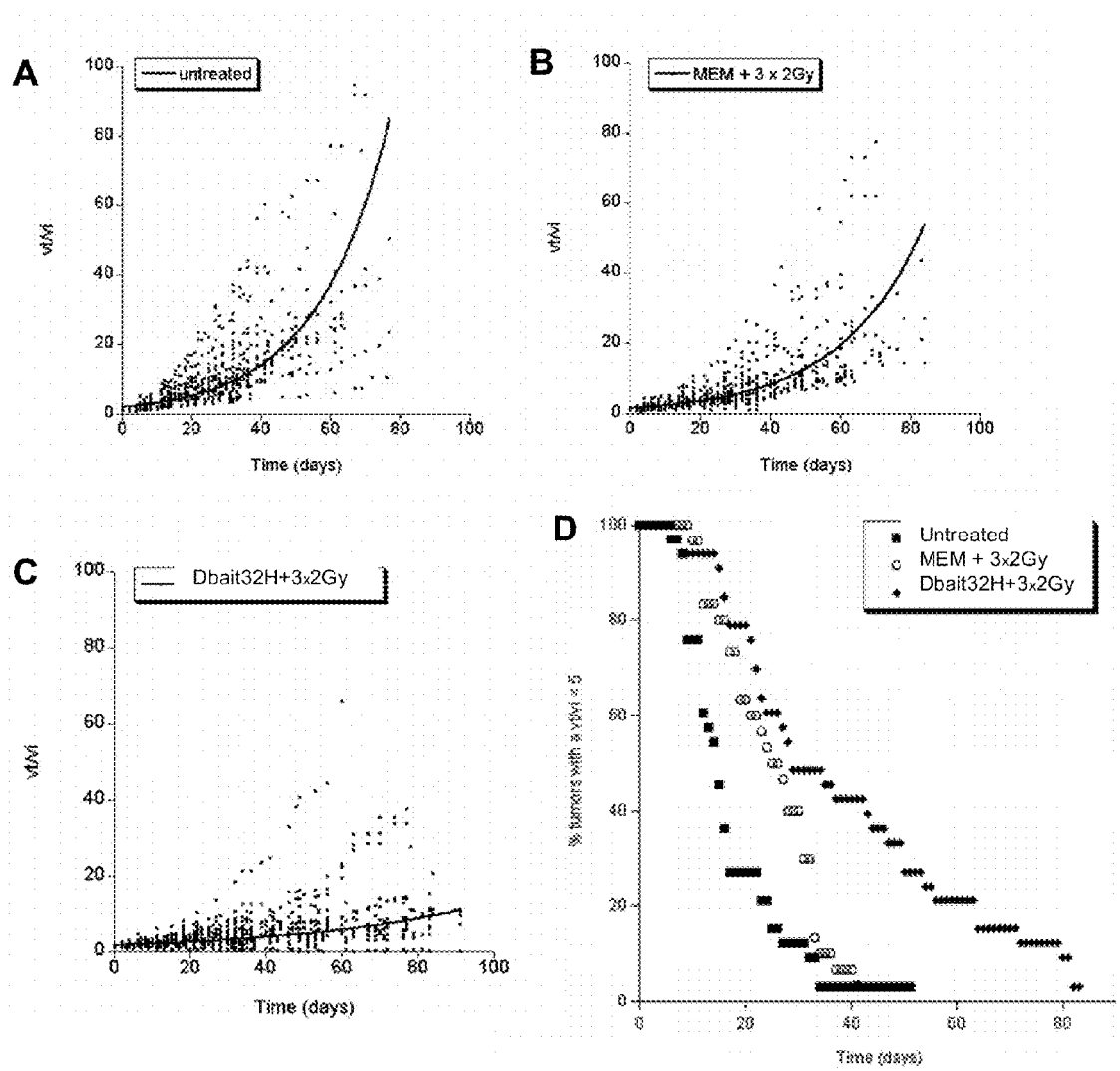
Figure 4.1

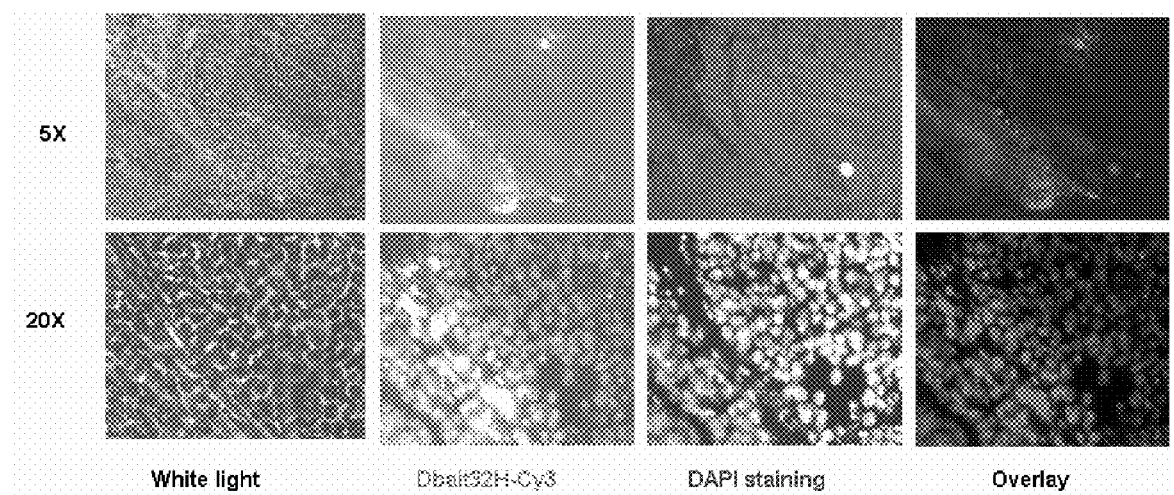
Figure 4.2

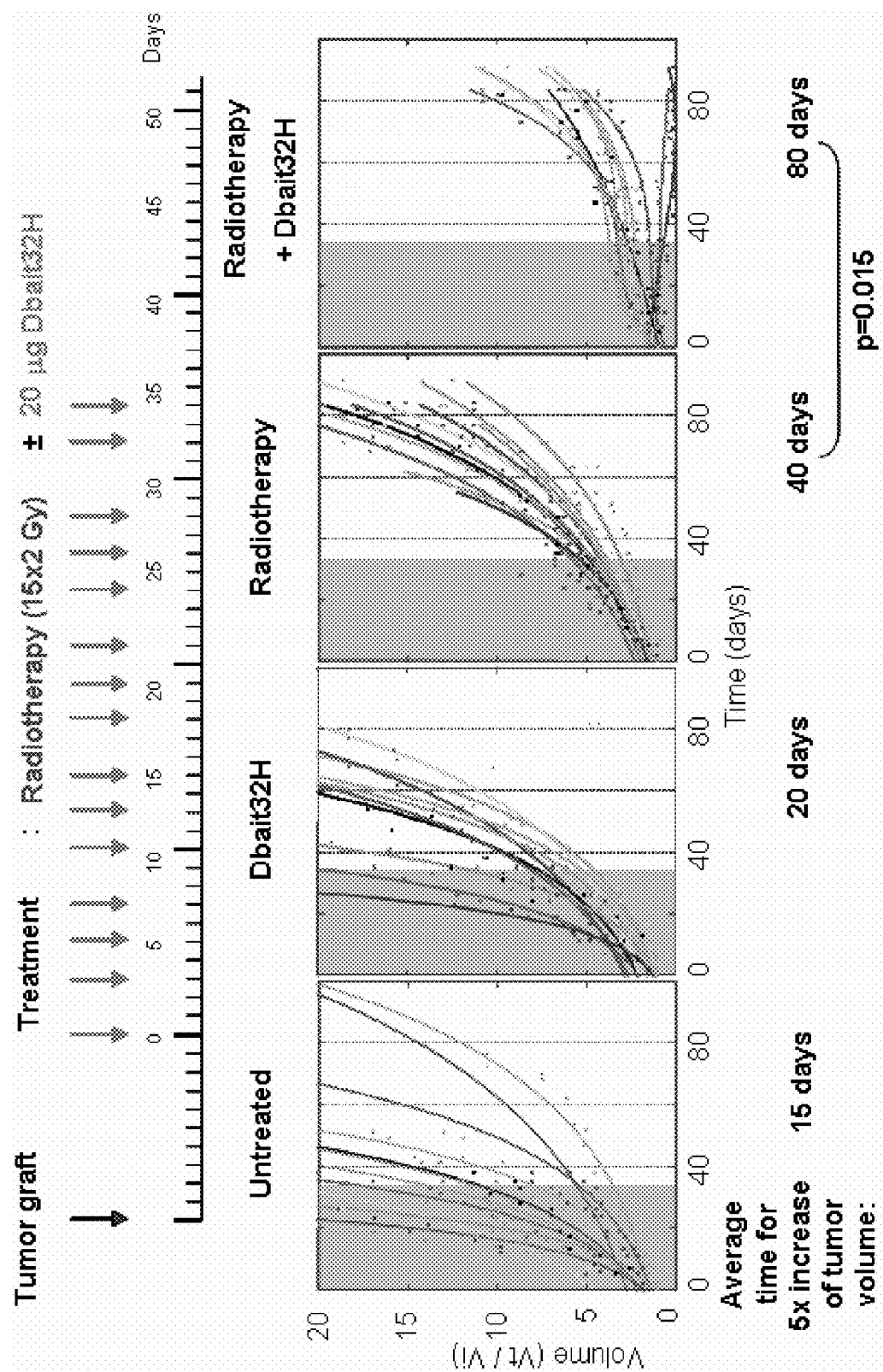
Figure 4.3

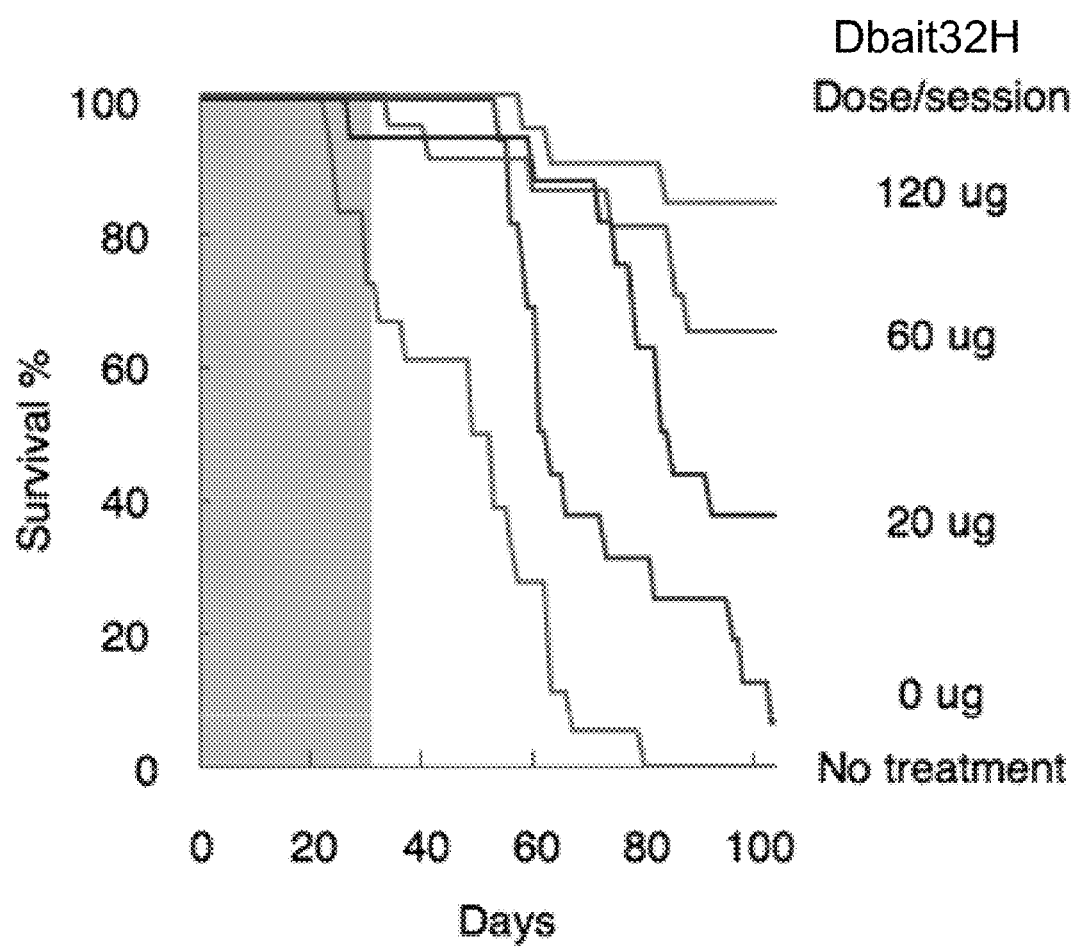
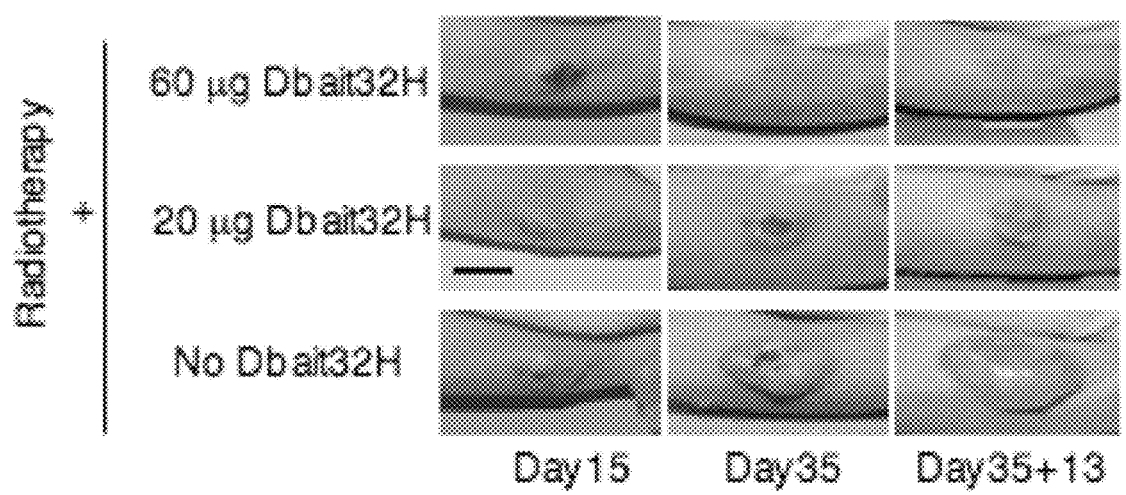
Figure 4.4

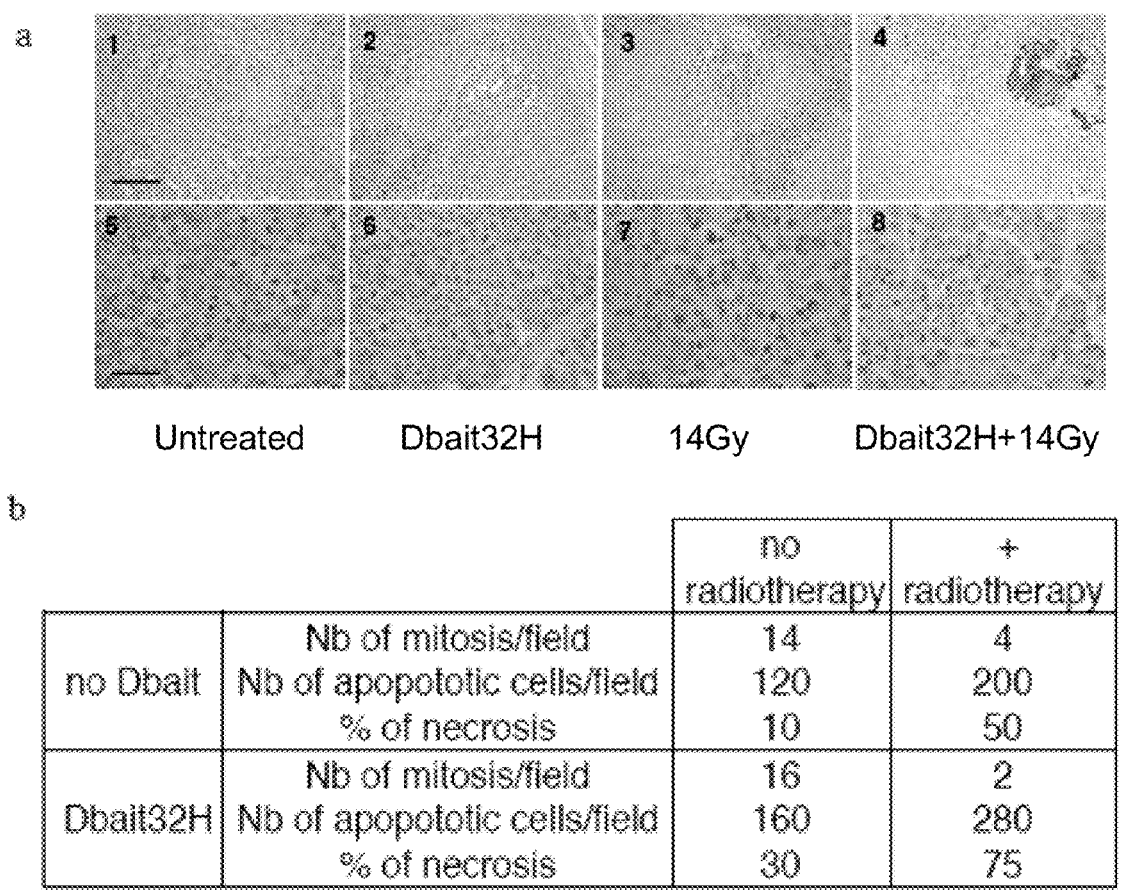
Figure 4.5

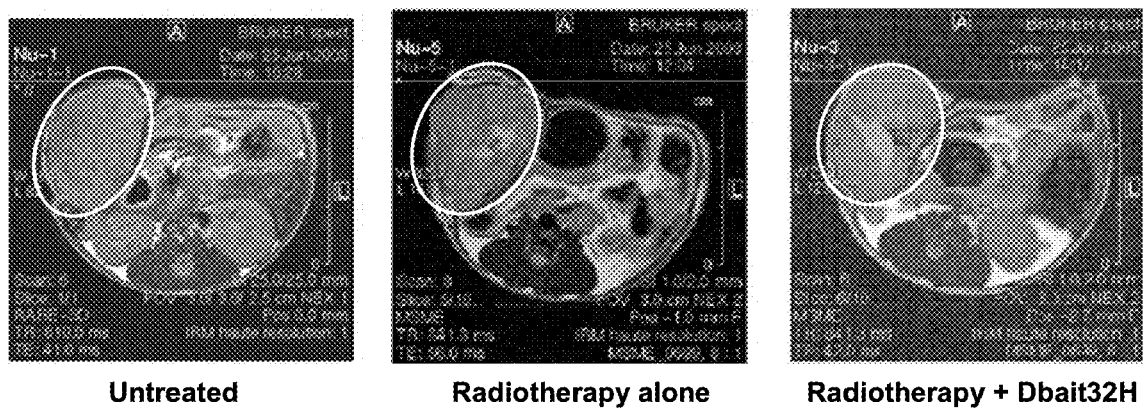
Figure 4.6

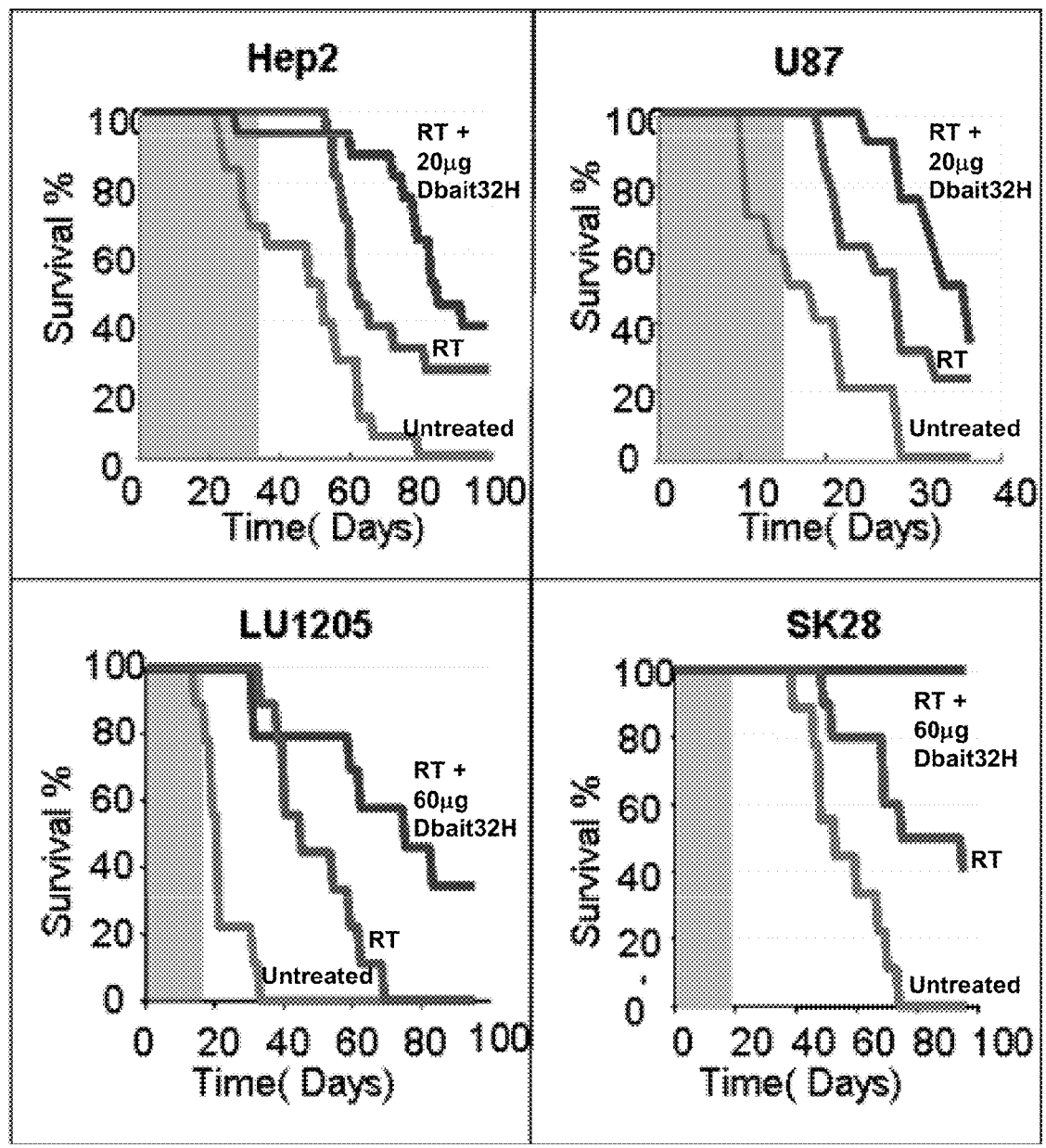
Figure 4.7

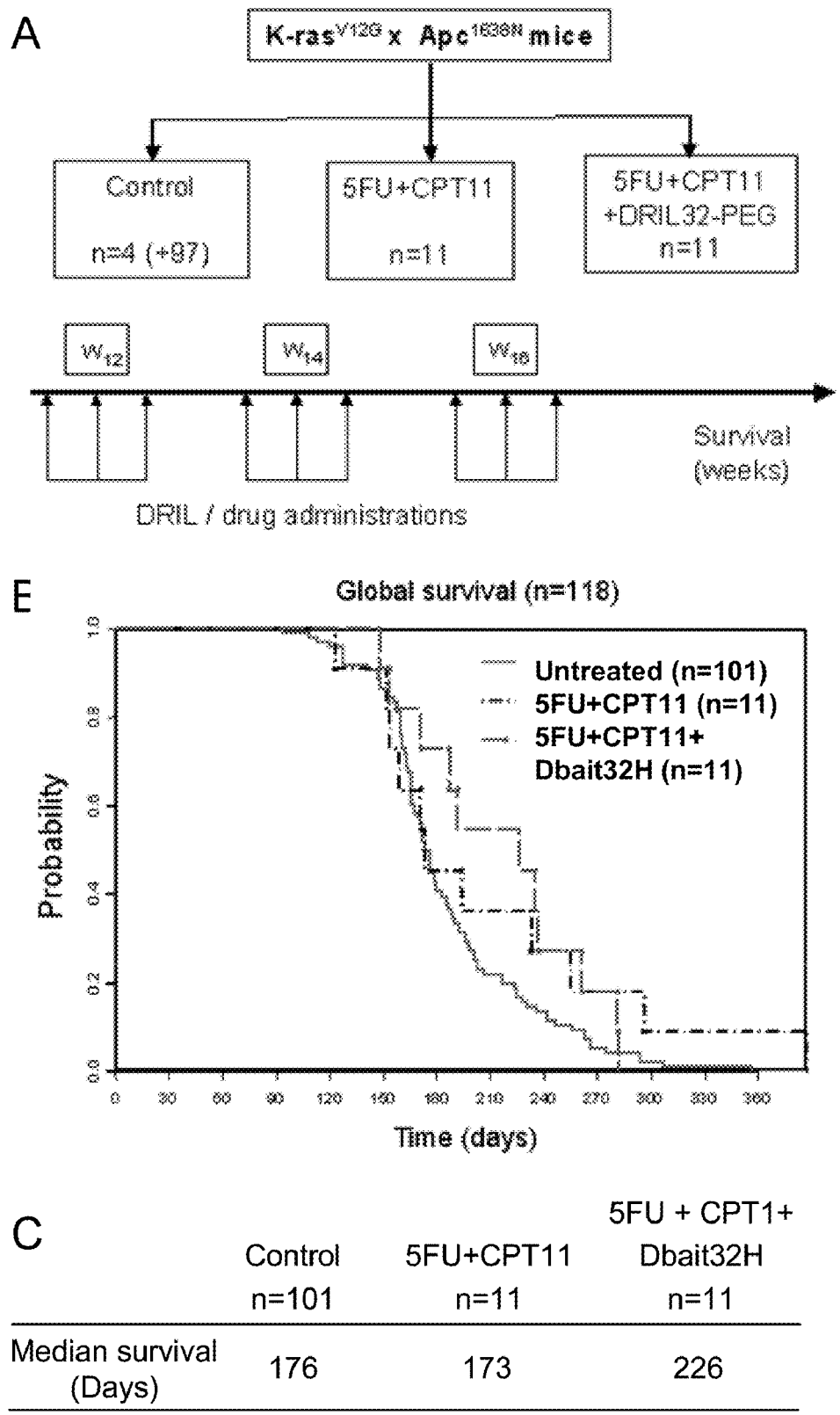
Figure 5.1

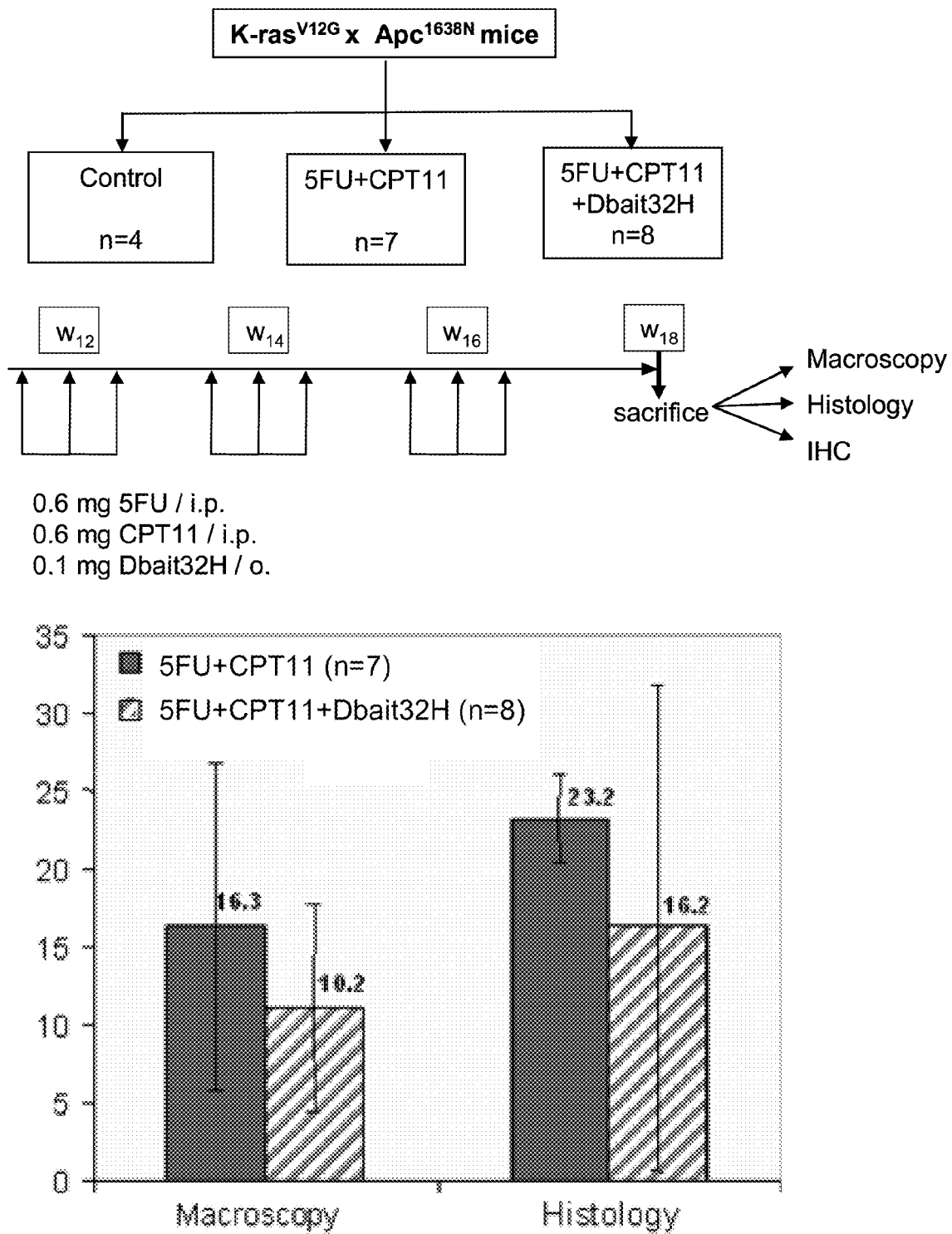
Figure 5.2

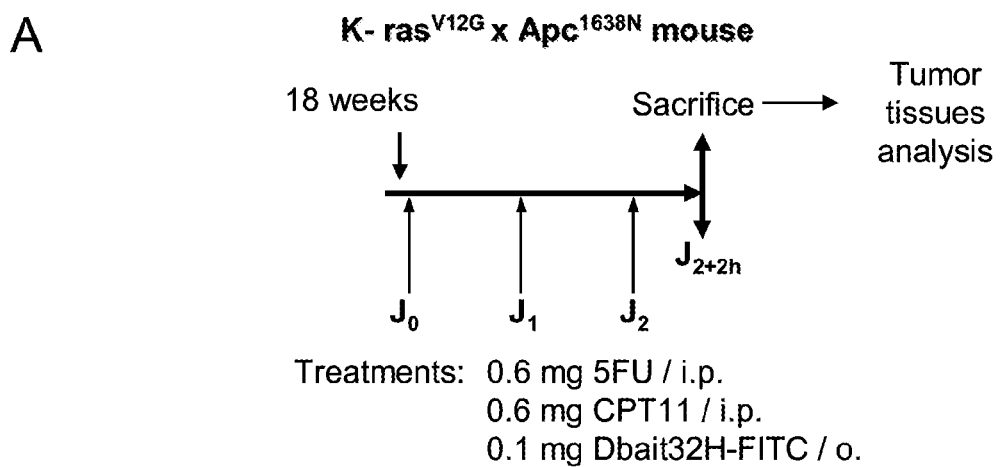
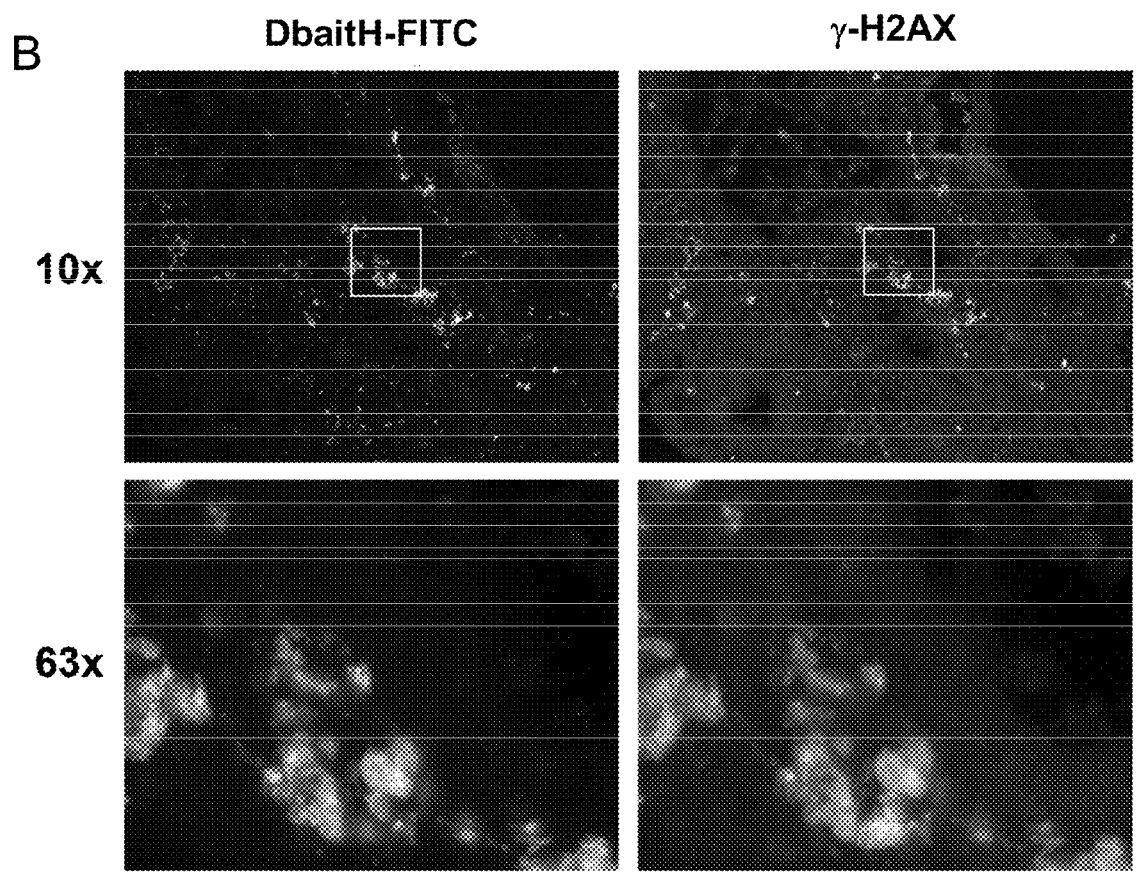
Figure 5.3

DBAIT AND USES THEREOF

The present application is a divisional of application Ser. No. 11/524,528 (now U.S. Pat. No. 7,476,729), filed Sep. 21, 2006, which is a continuation-in-part of application Ser. No. 10/576,818 (now U.S. Pat. No. 7,595,302), filed Jul. 19, 2006, which is a 371 National Phase of PCT/EP2004/012857, filed Oct. 25, 2004, and claims benefit of EP 03292666.9, filed Oct. 24, 2003, the entire contents of each of which is hereby incorporated by reference in this application.

This invention relates to compositions and methods of interfering with DNA repair pathways in mammalian cells. The invention particularly relates to nucleic acid molecules that interfere with DNA damage sensing, signaling and/or repair pathways, in particular the non homologous end joining (NHEJ) pathway of double-stranded break (DSB) repair, as well as to the uses thereof, particularly for triggering cell lethality of tumors submitted to anticancer therapies. The invention discloses a novel class of nucleic acid molecules, termed "DSB bait" or "Dbait", which may be used in a variety of therapeutic conditions in mammalian subjects, to interfere with DNA DSB repair pathways.

BACKGROUND

Radiotherapy and chemotherapy, alone or combined together with surgery, are essential therapeutic arsenals against human cancer.

Ionizing radiations cause directly or indirectly double-stranded breaks (DSBs) and trigger cell/tissue death (necrosis or apoptosis). The cytotoxic effect of ionizing radiation forms the basis for radiotherapy, which is widely used in the treatment of human cancer. The efficacy of radiotherapy is currently limited by the radio-resistance of certain tumors (for example, glioblastoma, head and neck squamous cell carcinoma) and by the side effects caused by irradiation of nearby normal tissues (for example, in the treatment of breast and cervical cancer).

In the past years, many studies have focused on biological mechanisms related to the ionizing radiation response, in order to gain insights into the complexity of phenomena underlying radio-sensitivity or radio-resistance of tumor cells. The understanding of the different pathways which finely regulate the response to ionizing radiation is an important step towards the identification of molecular targets for new drugs and therapies that, in association with radiotherapy, can improve the chance of recovery from tumors highly resistant to radiation, such as brain or head and neck tumors.

The use of chemotherapeutic agents can cause DNA damages, including direct or indirect DSBs. Examples of mostly used families of chemotherapeutic agents (chemical cytotoxics) are: inhibitors of topoisomerases I or II (camptothecin/topotecan, epirubicin/etoposide), DNA crosslinkers (cisplatin/carboplatin/oxaliplatin), DNA alkylating agents (carmustine/dacarbazine) or anti-metabolic agents (5-fluorouracil/gemcitabine/capecitabine), as well as inhibitors of the mitotic spindles (paclitaxel/docetaxel/vinorelbine).

Recent progress in developing biological drugs (monoclonal antibodies, cytokines/kinase inhibitors, immunotherapies/vaccines) has proven their efficiency and specificity towards a subset of tumors. But they are often used in combination with chemical cytotoxics. Despite of many progresses in the development of new cytotoxic drugs, the drug resistance to chemotherapy is still a major clinical concern in the treatment of cancers. The understanding of the mechanism of drug resistance related to drug uptake/efflux, metabolic degradation, mutagenesis of target enhanced repair, signaling of cell death (apoptosis and necrosis) is essential for insuring efficiency of chemotherapy and improve therapeutic index, especially, in some treatment-resistant tumors.

The association between chemotherapy and radiotherapy was widely used in cancer treatment. Although still not completely elucidated, the biological basis of action of the cytotoxics relies on cellular mechanisms, such as cell cycle or DNA damage, which is also important for the radio-induced cell death, leading to the additive or even better synergistic benefits by combining different treatments in cancer therapies.

In the last decade, many investigations were carried out in this field, and the complexity of signal transduction in response to radiation began to be delineated. In this respect, genes of particular interest to be targeted with ionizing radiations are those involved in the regulation of radiation-induced lethality mechanisms, such as apoptosis or DNA repair. As DSBs are the most lethal DNA damages, the efficacy of ionizing radiation decreases as that of DSB repair increases.

Two mechanisms are involved in the repair of DSBs: non homologous end-joining (NHEJ, sequence-independent pathway) and homologous recombination (HR, sequence-dependent pathway) (reviewed by Jackson, 2002). Targeting genes involved in these two main DSB repair pathways has so far led to little or moderate radio-sensitivity, depending on the used approaches and cancer cell lines (Belenkov et al., 2002; Marangoni et al. 2000; Ohnishi et al, 1998).

Ku (e.g., Ku70 and Ku80) and DNA-PKcs proteins are important in the repair of radiation- or chemo-induced DNA DSBs. If damage cannot be repaired on time, cells die. Therefore, they represent potentially interesting molecular targets for sensitizing target cells and tissues to radiotherapy and chemotherapy. Many approaches have thus been conceived and carried out to try to inhibit these key proteins (Ku70/Ku80, DNA-PKcs, etc.) involved in the NHEJ pathway, which is predominant in mammalian cells:

1) Inhibitors of PI3K (phosphatidylinositol-3-kinase) (i.e., DNA-PKcs, ATM, ATR) (Boulton et al., 2000; Durant & Karran, 2003; Willmore et al., 2004; Vauger et al., 2004);
2) Negative dominant & peptides (C-terminal of KU80) (Marangoni et al., 2000; Kim et al., 2002);
3) Single chain antibody variable fragment (scFv) (DNA-PKcs) (Li et al. 2003);
4) RNA Aptamer (SELEX: RNA binding Ku) (Yoo & Dynan, 1998);
5) Antisense (Ku70, Ku80, DNA-PKcs) (Li et al., 2003b; Marangoni et al., 2000; Sak et al., 2002);
6) siRNA (DNA-PKcs) (Peng et al. 2000).

Despite these tremendous efforts, the combination of the targeting of genes involved in DNA repair pathways and cancer therapies is still in early experimental stages and no clinical study has shown any proven benefits so far. It is worth to note that the above described approaches share a common feature: they target a single effector (protein) involved in a complex cascade pathway (such as NHEJ) with possible bypass or compensation.

SUMMARY OF THE INVENTION

The present invention relates to novel compositions and methods of interfering with DNA repair pathways in mammalian cells. The invention particularly relates to nucleic acid molecules that interfere, in a non gene-specific manner, with DNA damage sensing, signaling and/or repair pathways, as well as to the uses thereof, particularly for triggering cell lethality of tumors submitted to anticancer therapies.

The inventors have found that the sensitivity of cells to direct or indirect DNA damaging therapies can be enhanced by using (chemically modified or not) short dsDNA molecules which act as mimics of broken DNA fragments and are recognized as DSB sites induced by the DNA damaging treatments (i.e. the substrate mimics of DSB).

As shown in the examples, the molecules of this invention are effective in vitro as well as in viva, and may be used to confer or increase sensitivity of any tumor cell to DNA damaging cancer therapy treatment.

An object of the invention thus relates to such dsDNA molecules, also designated by the name of "DSB bait" molecules (Dbait in short), which are capable of enhancing the response of treatment-resistant tumors to radiotherapy and chemotherapy. As will be disclosed further below, Dbait molecules act by baiting and hijacking the holocomplex of DNA repair enzymes, and thereby interfere with DNA lesion sensing, signaling and/or repair processes. This novel approach is named "DNA bait".

A further object of this invention resides in a composition comprising a Dbait molecule and a pharmaceutically acceptable carrier or excipient.

A further object of this invention resides in a Dbait molecule in combination with (a) physical and/or chemical agent(s) which can directly or indirectly cause DSBs of DNA.

A further object of this invention is a method for treating a proliferative disorder (e.g., a cancer) using a combination of a Dbait molecule and a therapy which directly or indirectly causes DNA damage(s).

Another object of the invention relates to the use of Dbait molecules for making anticancer therapeutic adjuvant for enhancing efficiency of cancer treatment, particularly for the tumors poorly responding to radio- and/or chemotherapies.

A further object of this invention is a method of enhancing tumor sensitivity to DNA damaging anticancer therapy, the method comprising administering to a subject a Dbait molecule as defined above.

A further object of this invention is a method of treating cancer, the method comprising administering to a subject a Dbait molecule in combination with a DNA damaging anticancer therapy.

A further object of this invention is a composition for use in association with a DNA breaking treatment, particularly radiotherapy or chemotherapy, said composition comprising at least one Dbait molecule in combination with a pharmaceutically acceptable carrier, in an efficient amount to be introduced in the nucleus of tumor cells.

The invention may be used to confer sensitivity to cancer therapy in various types of cancers in mammalian subjects, particularly in human subjects, such as solid cancers and leukemia, particularly radio- or chemo-resistant cancers.

LEGEND TO THE FIGURES

FIG. 1.1: Band-shift assays performed on different $^{32}$P radio-labelled Dbait molecules (previously named DRIL molecules) in the presence of various amounts of nuclear extract (0, 10, 20, 40, 80, 160, 320 ng/μl) from Hep2 cells. The shifted bands were numbered 1 and 2. The band 3 is loading well.

FIG. 1.2: Identification of the presence of Ku proteins in the retarded bands of different $^{32}$P radio-labelled Dbait molecules (previously named DRIL molecules) involving proteins in Hep2 cell nuclear extract (0, 20, 80, 320 ng/μl). On line α-Ku, it is indicated when anti-Ku antibodies were added (+) or not (−) to the binding reaction before loading of sample on the gel. The shifted bands were numbered 1, 2 and 3 and a star was added to number for bands showing a shifted migration after anti-Ku binding.

FIG. 1.3: DNA end-joining assay with 20 μg Hep2 nuclear protein extract. Upper panel: the ligation of 0.2 μM $^{32}$P-labeled DNA fragments in the absence and in the presence of 20 μM Dbait in 20 μl assay buffer over various times. The bands 1-4 indicate the initial 300-bp DNA fragments (monomers [1]), the ligation products which migrate as dimers [2], trimers [3] or tetramers [4]. Lower panel: The percentage of ligation products was quantified and shown as a function of time (diamonds, without Dbait, circles, with 200 nM Dbait32H (SEQ ID NO: 1)), and as a function of the chemical structure of Dbait molecules (after 2 hour incubation with 200 nM various Dbait).

FIG. 1.4: DNA-dependent protein kinase (DNA-PK) activity assay in 1.5 μg of Hep2 nuclear protein extract of a number of 2 μg Dbait molecules with various lengths, sequences and chemical structures including modified backbones: Dbait32ss (SEQ ID NO: 1) and Dbait32css (SEQ ID NO: 6) are two 32-nt single strand DNA; Dbait32C (SEQ ID NO: 1) is a dumbbell 32-bp double strand DNA (without free blunt end); Dbait8H (SEQ ID NO: 4), Dbait16H (SEQ ID NO: 3), Dbait24H (SEQ ID NO: 2) and Dbait32H (SEQ ID NO: 1) are hairpin double strand DNA with a stem of 8, 16, 24 and 32-bp, respectively. Dbait32H (SEQ ID NO: 1), Dbait32Hb (SEQ ID NO: 5), Dbait32Hc (SEQ ID NO: 6) and Dbait32Hd (SEQ ID NO: 7) are 32-bp hairpin DNA with different sequences but the same base composition; Dbait32d-F (SEQ ID NO: 7) and DbaitHc-cy3 (SEQ ID NO: 6) are fluorescein and cyanine 3 tagged Dbait32Hd (SEQ ID NO: 7) and Dbat32Hc (SEQ ID NO: 6), respectively; Dbait32H-po (SEQ ID NO: 1) is a full length phosphodiester Dbait32H (SEQ ID NO: 1), as compared to other Dbait molecules which have 3-bp phosphorothioate at the free blunt end, except DbaitHc-3'mp (SEQ ID NO: 6) and Dbait32Hc-5'3'mp (SEQ ID NO: 6) which have 3-nt methylphosphonate at either the 3'-end or the both 5' and 3' end, respectively Dbait32Hc5'5' (SEQ ID NO: 5) has a 3'-3' linkage, thus exhibiting a 5'/5' blunt end; Cf. table 1.1 and table 1.2 for the details of these Dbait molecules. Data represent the mean value and standard deviation of at least 3 independent experiments.

FIG. 2.1: Clonogenic survival assay of Hela cells after 4×0.5 Gy (spaced 2 hours) irradiation performed with γ-rays from a $^{137}$Cesium source in the presence of various Dbait molecules (previously named DRIL molecules). Panel A: Dose-dependence of normalized survival clone number in the presence of Dbait32 (SEQ ID NO: 1) and Dbait32H (SEQ ID NO: 1). Panel B: Normalized survival clone number in the presence of different Dbait molecules at 83 nM (concentration in culture medium).

FIG. 2.2: Additional clonogenic survival assay of Hela cells after 4×0.5 Gy (spaced 2 hours) irradiation performed with γ-rays from a $^{137}$Cesium source in the presence of various Dbait molecules. Upper panel: Dose-dependence of normalized survival clone number in the presence of Dbait32H (SEQ ID NO: 1) and Dbait8H (SEQ ID NO: 4). Lower panel: Normalized survival clone number in the presence of different 2 μg Dbait molecules.

FIG. 2.3: Inhibition of radiation-enhanced illegitimate integration of a linear plasmid fragment (2 μg) carrying the gene coding for neomycin resistance by 2 μg Dbait32H molecules (SEQ ID NO: 1) (previously named DRIL32-PEG molecule).

FIG. 2.4: Additional assays of the inhibition of radiation-enhanced illegitimate integration of a linear plasmid fragment (2 µg) carrying the gene coding for puromycin resistance by various Dbait32 molecules (2 µg). Upper panel: Dose-dependence of Dait32H molecule (SEQ ID NO: 1) in the presence of fractionated (4×0.5 Gy) irradiation (filled circles) or in the absence of irradiation (filled triangles); Lower panel: The efficiency of plasmid integration in the presence 2 µg various Dbait molecules or 200 µM DNA-PK inhibitors (wortmannin or NU7026), and with (black) or without irradiation (grey).

FIG. 2.5: Immunodetection of double strand break (DSB) sites as revealed by γ-H2AX foci in Hela cells transfected by fluorescent Dbait32H-FITC molecules (SEQ ID NO: 1) (previously named DRIL32-FITC molecule) at 2 hours after 2 Gy irradiation. Left panel: fluorescence of Dbait32H-FITC (SEQ ID NO: 1) (bright dots and patches) and DSB sties detected by immunofluorescence of γ-H2AX antibody in nuclei; Right panel: the same image of nuclei with DSB sites detected by immunofluorescence of γ-H2AX antibody and DAPI counterstaining. The arrows at the lower left corner show the absence of Dbait32H-FITC (SEQ ID NO: 1) and γ-H2AX signal in nucleus. The arrows at the upper right corner show the co-localized Dbait32H-FITC (SEQ ID NO: 1) and γ-H2AX signals.

FIG. 2.6: Upper panel: Histone H2AX phosphorylation by PIKKs. Total cell extracts were analyzed by western blotting for the level of phosphorylated form of histone H2AX (γ-H2AX) as compared to the total H2AX protein. Hep2 cells were transfected 5 hours with various Dbait molecules 32Hc (SEQ ID NO: 6), 24H (SEQ ID NO: 2), 16H (SEQ ID NO: 3) and 8H (SEQ ID NO: 4) for 5 h, or not transfected. They were irradiated at the end of transfection, incubated for one hour and then analyzed. The resultants are presented as histogram of normalized ratio of γ-H2AX/H2AX.

Lower panel: Kinetics of the persistence of DSB sites revealed by γ-H2AX foci by FACS in the irradiated (IR) cells: Dbait32Hc+IR (solid line), IR alone (dashed line) and untreated (dotted line).

FIG. 3.1: FACS analyses of the untreated GMA32 cells, the cells transfected alone, or transfected with different Dbait molecules (previously named DRIL molecules) by lipofectamine, but without further irradiation or mitotic inhibitor treatment. The M1 phase represents the percentage of cells in sub-G1 stage indicative of cell death.

FIG. 3.2: Immunodetection of DNA repair foci by γ-H2AX labeling (bright dots or patches in nuclei) in the untreated GMA32 cells, the cells transfected alone, or transfected with different Dbait molecules (previously named DRIL molecules) by lipofectamine. The counterstaining of cell membranes and nuclei were achieved by FITC-DiOC6 and DAPI.

FIG. 3.3: Western blot analysis of the phosphorylation status of p53 serine 15 residue of the untreated GMA32 cells, the cells transfected alone, or transfected with different Dbait molecules (previously named DRIL molecules) by lipofectamine, but without further irradiation or mitotic inhibitor treatment.

FIG. 3.4: Clonogenical survival of untreated and treated GMA32 cells by 4 Gy irradiation or by different mitotic inhibitors (200 nM nocodazole, 100 nM navelbine (vinorelbine) or 200 nM taxol (paclitaxel)) in the presence of different Dbait molecules (previously named DRIL molecules).

FIG. 4.1: Growth of the xenografted human larynx tumor on mice monitored as the ratio of the tumor volume at time t over the initial volume ($V_t/V_i$) with or without treatments. Panel A: Untreated arm (n=38); Panel B: control arm with 20 µl culture medium (MEM)+3×2 Gy/week irradiation (n=30); Panel C: the arm with 1 nmole (20 µg) Dbait32H (SEQ ID NO: 1) (previously named DRIL32-PEG molecules)+3×2 Gy/week irradiation (n=35). MEM or Dbait32H (SEQ ID NO: 1) was delivered by intratumoral injection 5 hours prior irradiation. The split irradiation dose (2 Gy) was given one of every two days, three times a week. The treatment lasted 5 weeks totaling 30 Gy irradiation. The dots represent the time course of tumor volume of each mouse. The solid lines are the best polynomial fitting. Panel D shows a Kaplan-Meier plot of all mice of which the increase in tumor volume ($V_t/V_i$)<5.

FIG. 4.2: Distribution of cyanine C3 labelled Dbait32H (SEQ ID NO: 1) in Hep2 xenograft tumor in nude mice. 20 µg Dbait32H-Cy3 (SEQ ID NO: 1) formulated with Superfect (transfection agent) was injected into 1.5 cm³ Hep2 tumor. The mice were sacrificed 6 hours after the injection. The tumors were taken out and cryo-sliced for analysis without fixing. DAPI was used for nuclei staining.

FIG. 4.3: Radiosensitization of Hep2 xenografted tumors in nude mice. Tumor growth was monitored during treatment (15 sessions within 35 days; grey background) and after (white background) in four groups of 10 animals with different treatments. Individual tumor growth is indicated for each animal. The treatment protocol was indicated at the top. For each treatment session, 2 µg Dbait32H (SEQ ID NO: 1) formulated with transfection agent (PEI) was injected into tumor 5 hours prior 2 Gy irradiation. The average times for 5 fold increase of tumor volume of each group are also indicated. The p-value was calculated for the group received combined treatment as compared to the group received the irradiation alone.

FIG. 4.4: Upper panel: Kaplan-Meier representation of survival of mice subcutaneously xenografted by Hep2 tumor. The treatment protocol was described in FIG. 4.3. The five groups were included: untreated, mock-transfected and irradiated, treated by combined irradiation and increasing amount of Dbait32H (SEQ ID NO: 1) (20, 60 and 120 µg/session). Number of animals for each group is indicated in table 3.2. Grey background indicates the period of treatment. Lower panel: Pictures of tumors representative of the three groups (untreated, treated with 20 and 60 µg Dbait32H (SEQ ID NO: 1)/session associated with 2 Gy irradiation) which were taken 15 days after beginning of treatment, at the end of treatment (35 days) and 13 days after the end of treatment (35+13 days).

FIG. 4.5: Histological analysis of xenograted Hep2 tumors at mid-course treatment (7 sessions). Tumors were taken out 20 days after beginning of various treatment protocols as indicated. They were fixed in formalin and tissue sections were stained with hematoxylin, eosin and safran. Two tumors for each treatment protocol were analyzed by microscopy. Panel a: Pictures of representative fields of each protocol. Scale bars indicate 400 mm (panels 1-4) and 100 mm (panels 5-8). Color pictures are available upon request. Panel b: The extent of necrosis is expressed as the proportion of the surface area of the tissue section analyzed that was necrotic. The number of mitotic cells and apoptotic cells were estimated from representative non-necrotic fields of about 1,000 cells analyzed at high power.

FIG. 4.6: NMR imaging of xenografted Hep2 tumors at the mid-course treatment (7 sessions). Three representative cross-section images were shown with untreated tumor, tumor treated by irradiation (2 Gy/session), and by the combined Dbait32H (SEQ ID NO: 1) (20 µg/session) and irradiation (2 Gy/session). The tumors are outlined by white circle. The grey mass inside tumor indicated the necrotic area.

FIG. 4.7: shows Kaplan-Meier representation of survival of nude mice subcutaneously xenografted by various tumors (Hep2; squamous cell carcinoma; U87; glioblastoma;

LU1205 and SK28; two types of melanoma). The period for treatment is indicated by grey area.

FIG. 5.1: Panel A: Treatment protocol for three groups/arms of the K-Ras$^{V12G}$×Apc$^{1638N}$ transgenic mice at the mean age of 12 weeks: the control group (untreated), the group treated by 5FU+CPT11, the group treated by 5FU+CPT11 and Dbait32H (SEQ ID NO: 1) (previously named DRIL32-PEG molecules). It was performed by three cycles of treatment. Each cycle consists of intraperitoneal injection of 0.6 mg 5FU and 0.6 mg CPT11, along with 0.1 mg Dbait32H (SEQ ID NO: 1) by oral administration, three times a week, followed by one week rest. The number of mice involved in each groups is indicated in parenthesis. The end point is the time of survival; Panel B: Kaplan-Meyer plot of survival curves of the three groups; Panel C: The median survival time of three groups as shown in panel B.

FIG. 5.2: Mean number of tumors in digestive tract per animal by macroscopy or histology examination of the groups treated by 5FU+CPT11 and by 5FU+CPT11 and Dbait32H (SEQ ID NO: 1) (previously named DRIL32-PEG molecules). The number of animals in each group was indicated in parenthesis. All mice were sacrificed two weeks (week 18) after the protocol shown in the upper panel. The mean number of the control arm (untreated group, n=101) is 30.8/animal (data not shown).

FIG. 5.3. Fluorescence microscopy analysis of digestive tract tissue. Panel A: Protocol schema (i.p.: intraperitoneal injection; o.: oral administration). Panel B: Fluorescence of Dbait32H-FITC molecules (SEQ ID NO: 1) (previously named DRIL32-FITC molecule) (left) and of immunofluorescence labelled γ-H2AX (right) on the 5 μm section from the tumor tissue of the treated animal according to the protocol given in panel A. Lower parts show the details (using 63× lens) of the indicated zone in the upper parts (using 10× lens, white box). Co-localization of fluorescent Dbait32H-FITC (SEQ ID NO: 1) and labelled γ-H2AX appears as bright dots over DAPI counterstained nuclei.

DETAILED DESCRIPTION OF THE INVENTION

As discussed above, the invention discloses a novel class of therapeutic molecules which can interfere, in a non gene-specific manner, with DNA repair systems in mammalian cells. These new molecules, termed Dbait molecules, are substrates for the holocomplex of proteins involved in the NHEJ pathway (sequence-independent pathway), particularly Ku and/or DNA-PKcs proteins, and can neutralize the DNA repair capacity of cells, thereby increasing their sensitivity to DNA damaging treatments.

The invention thus relates to such molecules, their manufacture and their therapeutic use, particularly for treating proliferative diseases in combination with a DNA damaging treatment.

Dbait molecules of the present invention may be defined by a number of characteristics, such as their minimal length, the presence of a free end at least, and the presence of a double stranded portion. As will be discussed below, an important feature of Dbait molecules is that their precise nucleotide sequence does not impact substantially on their activity. Furthermore, Dbait molecules may contain a modified and/or non-natural backbone.

Accordingly, a first object of this invention resides in a nucleic acid molecule, wherein said molecule comprises a double stranded portion of at least about 16 bp, has at least one free end, and binds at least a Ku complex involved in the NHEJ pathway.

The molecule is preferably of non-human origin (i.e., its nucleotide sequence and/or conformation (e.g., hairpin) do not exist as such in a human cell), most preferably of recombinant and/or synthetic origin.

According to the mechanism of action of Dbait molecules, the sequence of the Dbait molecules plays little, if any, role. Accordingly, in contrast with molecules used in the prior art for gene/protein-specific targeting (e.g., antisense, antigene, siRNA, aptamer, ribozyme, etc.), Dbait molecules may not have any significant degree of sequence homology or identity to known genes, promoters, enhancers, 5'- or 3' upstream sequences, exons, introns, etc. In other words, the action of Dbait molecules to interfere with NHEJ pathway is sequence-independent, and Dbait molecules can have less than 70%, even less than 50% sequence identity to any gene in a human genome.

This sequence independent mechanism of action is a hallmark of Dbait molecules, which clearly distinguishes them from other gene-specific or protein-specific (sequence dependent) therapeutic agents such as antisense oligonucleotides, small interference RNA (siRNA, shRNA and miRNA), and immunostimulating CpG oligonucleotides, as well as aptamers designed to trap a specific proteins.

In a preferred embodiment, the sequence of the Dbait molecules has an overall degree of identity to human nucleic acid sequences which is less than about 70%, 60%, 55% or 50%. Methods of determining sequence identity are well known in the art and include, e.g., Blast.

In a particular embodiment, the Dbait molecule does not hybridize, under stringent conditions, with human genomic DNA. Typical stringent conditions are such that they allow to discriminate fully complementary nucleic acids from partially complementary nucleic acids (Cf e.g. Sambrook et al).

In a preferred embodiment, the sequence of the Dait molecules is devoid of CpG in order to avoid the well known toll-like receptor-mediated immunological reactions, if such effect is undesirable.

Considering their mechanism of action, the length of Dbait molecules may be variable, as long as it is sufficient to allow appropriate binding of Ku protein complex. The experimental section shows that the minimal length of Dbait molecules is about 16 bp, to ensure binding to a Ku complex. Preferably, Dbait molecules comprise between 16-200 bp, and most preferably between 24-100 bp. Specific examples of Dbait molecules contain 24 bp, most preferably 32 bp. As shown in the examples, such a length is sufficient to allow binding of a Ku complex comprising Ku and DNA-PKc proteins.

Particularly preferred Dbait molecules comprise 28-100 bp, and more advantageously 32-100 bp.

The Dbait molecules according to the invention must have at least one free end, as a mimic of DSB. Said free end may be either a free blunt end or a 5'-/3'-protruding end. In a particular embodiment, they contain only one free end. In another particular embodiment, they contain two free ends.

Dbait molecules can be linear or, preferably, made of hairpin double-stranded nucleic acids. In such a case, the loop can be nucleic acids, or other chemical groups known by skilled person, preferably a linker such as hexaethyleneglycol or tetradeoxythymidylate (T4).

In a preferred embodiment, the Dbait molecules are such that:

1) the double-stranded Dbait molecules are capable of being uptaken by cells/tissue body into the cell nucleus when used with pharmaceutically acceptable carriers/excipients;

2) the at least one free end of the Dbait molecules is recognizable by the holocomplex of enzymes involved in DSB damage sensing, signaling and/or repair processes;

3) the at least one free end of the Dbait molecules is amenable by said complex to be incorporated in the tumor cell genomic DNA.

In a particular embodiment, the Dbait molecules have a non replicative structure, due their structure and/or backbone.

In this respect, the Dbait molecules according to the invention may have exclusively or mainly (above 50%) a native phosphodiester backbone or a chemically modified phosphodiester backbone, or another backbone with chemical groups or mixtures of chemical groups, provided the modified dsDNA remain substrates for the holocomplex involved in the NHEJ pathway, particularly Ku and DA-PKcs proteins, as well as DSB damage sensing or signaling pathway. Advantageously, the chemical modifications are intended to confer chemical stability to Dbait molecules and/or to prevent them for further replication (potential cause of mutagenic effect) upon their genomic integration if it occurs.

They can also have sugar mimics such as 2'-O-alkylribose, 2'-O-alkyl-C4' branched ribose, cyclobutyls or other carbocyclics or hexitol in place of the pentofuranosyl group.

Preferred Dbait comprise one or several chemical groups at the end of one or of each strand. Preferred chemical groups comprise phosphorothioates. Alternatively, preferred Dbait have 3'-3' nucleotide linkage, or nucleotides with methylphosphonate backbone.

Other modified backbones of the invention comprise phosphoramidates, morpholino nucleic acid, 2'-0,4'-C methylene/ethylene bridged locked nucleic acid, peptide nucleic acid (PNA) and short chain alkyl, or cycloalkyl intersugar linkages or short chain heteroatomic or heterocyclic intrasugar linkages of variable length, or any modified nucleotides known by skilled person.

U.S. Pat. No. 5,677,437 describes heteroaromatic oligonucleoside linkages. Nitrogen linkers or groups containing nitrogen can also be used to prepare oligonucleotide mimics (U.S. Pat. No. 5,792,844 and U.S. Pat. No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phophodiester backbone of the oligonucleotide may be replaced with a polyamide backbone, the bases being bound directly or indirectly to the aza nitrogen atoms of the polyamide backbone. Other synthetic oligonucleotides may contain substituted sugar moieties comprising one of the following at the 2'position: OH, SH, OCH3, SCH3, F, OCN, OCH2CH2OCH3, O(CH2)nNH2 or O (CH2) nCH3 where n is from 1 to about 10; Cl to C10 lower alkyl, substituted lower alkyl, alkaryl or aralkyl; Cl; Br; CN; CF3; OCF3.; 0-S—; or N-alkyl; 0-, S—, or N-alkenyl; SOCH3; S02CH3; ONO; NO; N3

SaID NO:n-replicable element(s) can be incorporated at the internal position or at the end of the double-stranded fragment. It (they) may comprise: a) a unit which cannot be used as a template for DNA replication, such as a polyethyleneglycol chain, preferably a hexaethyleneglycol chain, or any hydrocarbon chain, eventually interrupted and/or substituted by one or more heteroatoms e.g. oxygen, sulfur, nitrogen, or heteroatomic or heterocyclic groups comprising one or more of heteroatoms; b) a unit which is a blocking element as it is not amenable by DNA polymerases or exonucleases, such as any 3'-modified nucleotides, or other ones known by skilled person; c) a native oligonucleotide, such as Tn, when used in the loop of an hairpin fragment, such as a tetradeoxythymidylate (T4).

Said strands are made by chemical synthesis, semi-biosynthesis or biosynthesis, any method of amplification, followed by any extraction and preparation methods and any chemical modification.

The bioactivity of Dbait molecules can be assessed by in vitro and cultured cell based assays, as described e.g., in examples 2 and 3, and/or also by in vivo assays, as described e.g., in examples 4 and 5. The most easy and relevant assay is the DNA-dependent protein kinase activity assay (cf. example 2, FIG. 1.4). This simple assay has been so far predictive of in vivo activity of Dbait molecules. However, other cultured cell based assays, such as the assay of the inhibition of radiation-enhanced illegitimate integration is also relevant (cf. example 3, FIG. 2.3 & FIG. 2.4).

In a particular embodiment, the Dbait molecules of this invention are capable of activating DNA-PK.

In a particular embodiment, the Dbait molecules of this invention are capable of inhibiting radiation-enhanced illegitimate DNA integration.

In an other particular embodiment, the Dbait molecules of this invention bind a Ku complex in vitro, e.g., as determined by gel shift assay. Such a Ku complex may comprise one or several Ku proteins only, such as Ku70 and/or Ku80, or a combination of one or several Ku proteins and at least a DNA-PKc protein.

In an other particular embodiment, the Dbait molecules of this invention penetrate the nucleus.

Most preferred Dbait molecules of this invention combine several or all of the above characteristics.

The experiments carried out in cultured cells and in xenografted tumors on nude mice and genetically modified mice have shown that Dbait molecules of this invention trigger cell/tissue lethality of tumors submitted to a radio- and/or chemotherapy.

The invention thus also relates to adjuvant compositions to be used in association with a DNA breaking treatment, said compositions comprising a Dbait molecule such as above defined, in combination with a pharmaceutically acceptable carrier/excipient, in an efficient amount to be introduced in the nucleus of tumor cells.

The invention also relates to a method for promoting tumor sensibility to anticancer therapies which comprises, in association, introducing into cancer cell/tissue Dbait molecules such as above defined, and inducing in cells, DNA breakage by a DNA damaging method.

According to an embodiment of the invention, a transfection agent is used in said introduction step.

Based on the protocol used in in vivo studies, the invention provides rational to establish clinical protocol of the use of Dbait molecules in combination with radiotherapy or chemotherapy. The rational underlying any protocol is that the Dbait molecules should be delivered in the nucleus of cells when DNA damaging event occurs. Therefore, Dbait molecules shall preferably be administered prior to radiotherapy, whereas they can be given along with chemotherapeutic agent(s) depending on the administration mode and the pharmacokinetics of each drug.

A typical protocol comprises administration of Dbait molecules before irradiation, for example 5 hours. The use of a fractionated irradiation is particularly efficient, for example 15×2 Gy in six weeks, or 6×5 Gy in two weeks.

Advantageously, said method comprises coupling the treatment with Dbait molecules with a double chemotherapy. For example 5FU and CPT 11 are injected together 3 times, 3 consecutive days, spaced by a full week of rest. Alternatively the treatment with Dbait molecules is coupled with radiotherapy.

It will be easily adapted for humans by the one skilled in the art, particularly depending on the weight/body surface of the patient.

In a preferred embodiment, the Dbait molecules are chemically modified Dbait molecules such as above defined and other practice in human therapy.

In another embodiment, the Dbait molecules are not chemically modified and correspond to native nucleic acid fragments, but exhibit the characteristics of chemically modified fragments, particularly have the number of base pairs and properties defined with respect to said chemically modified Dbait molecules.

More particularly DNA strand breakage is achieved by ionized radiation (radiotherapy) or chemical reaction (chemotherapy).

Such a method is a new therapeutic adjuvant in conjunction with DNA damaging therapies to treatment the diseases resulting from uncontrolled cell proliferation, in particular cancer. In other words, Dbait is mainly intended to be used in anticancer therapies, but it may also be used in many antiproliferation treatments, such as for treating psoriasis.

This method is addressable to treat proliferative disorders:

They can be non malignant, such as psoriasis and vascular proliferative stenosis/restenosis.

They can be malignant.

The concerned organ or region can be: lung and bronchi, head and neck, gastro-intestinal tract, colorectal cancer, genito urinary tract, gynecologic organs, breast, endocrines, skin, retina, CNS, hematological organs, metastasis of known or unknown primary site, remnants (thymus for instance).

Histological nature can be epithelial, squamous cell carcinoma, adenocarcinoma, transitional carcinoma, fibroblast/angioblast derived (sarcomas), neuronal, glial derived, endocrine, carcinoid, gastrointestinal stroma, endothelial, hematopoietic, embryonic.

The invention also relates to the use of saID NO:n-chemically modified Dbait molecules for making anticancer drugs for treating tumors, particularly highly resistant tumors to radio- and/or chemotherapies, said drugs being used in association with a DNA breaking (e.g. damaging) treatment, particularly radiotherapy or chemotherapy.

In vivo, the chemically modified or non-modified Dbait molecules are administrated by any appropriate route, with appropriate acceptable carrier/excipient, such as oral, or intravenous, or intratumoral administration, or sub-cutaneous injections, or topic administration, or others.

A further object of this invention resides in the use of a Dbait molecule as defined above for the manufacture of a medicine to enhance cell (e.g., tumor) sensitivity to DNA damaging therapy.

A further object of this invention resides in the use of a Dbait molecule as defined above for the manufacture of medicine for treating cancer in combination with a DNA damaging anticancer therapy.

Preferably, the DNA damaging anticancer therapy is selected from radiotherapy and chemotherapy. Further preferably, the molecule is administered prior to radiotherapy and/or prior to and/or along with chemotherapy.

Others characteristics and advantages of the invention will be given in the following examples, with reference to the attached figures and Tables.

EXAMPLES

Molecular and cellular studies as well as assays in xenografted human radio-resistant tumor (head & neck squamous cell carcinoma, glioblastoma, melanoma) on nude mice and in $Ras^{V12G} \times Apc^{1638N}$ double mutation induced tumor in digestive track on transgenic mice were performed in order to:

i) assess the biological activities of Dbait molecules;

ii) validate DNA bait approach by using Dbait molecules in sensitizing anticancer therapies;

iii) elucidate molecular and cellular mechanisms underlying the observed Dbait-mediated sensitization. The outcomes of these investigations are outlined and summarized in the examples.

Example 1

Design, Synthesis and Preparation of Dbait Molecules

Two types of Dbait molecules were designed: linear or hairpin dsDNA fragments. For hairpin Dbait molecules, a hexaethyleneglycol linker or a tetradeoxythymydylate was used as loop.

The end(s) of dsDNA stem can be protected against chemical degradation by 3'-exonucleases by the incorporation of phosphorothioates, methylphosphonates or 3'-3'nucleotide linkage. In principle other chemical modifications can be used provided that they are compatible with Ku70/Ku80 binding and DNA-PKcs activation (Martensson & Hammarten, 2002). Different Dbait molecules with various stem length 8 bp (Dbait8H) (SEQ ID NO: 4), 16 bp (Dbait16H) (SEQ ID NO: 3), 24 bp (Dbait24H) (SEQ ID NO: 2) and 32 bp (Dbait32H) (SEQ ID NO: 1), as well as different stem sequences were assayed. A dumbell dsDNA fragment (Dbait32C) (SEQ ID NO: 1) where both ends were sealed by two hexaethylene loops was also designed, as control. Some Dbait molecules were labelled via a T tagged with fluorescein (Dbait32H-FITC) (SEQ ID NO: 1), cyanine 3 (Dbait32H-Cy3) (SEQ ID NO: 1), cyanine 5 (Dbait32Hc-Cy5) (SEQ ID NO: 1), or biotin (Dbait32H-Biot) (SEQ ID NO: 1). Table 1.1, 1.2 and 1.3 summarized the sequences and chemical structures of Dbait molecules used in this work.

TABLE 1.1

Sequences and chemical structures of Dbait molecules. The uppercase letters are nucleotides with phosphodiester backbone. The bold uppercase letters are nucleotides with phosphorothioate backbone. Half circle solid line symbolizes hexaethyleneglycol linker. Dbait32-T4 (SEQ ID NO: 1) contains four thymines ($T_4$) as a linker instead of a hexaethyleneglycol linker. Dbait32C (SEQ ID NO: 1) is a dumbbell (closed) molecule. Dbait32Hc-5'5' (SEQ ID NO: 5) has a shuffled sequence (same base composition but in different order, cf. Dbait32Hc (SEQ ID NO: 6) in table 1.2) and a 3'-3' linkage. Various labelled (fluorescent dye or biotin) Dbait32H (SEQ ID NO: 1) molecules are indicated.

| Dbait molecules (Designation used in the current CIP) | DRIL molecules (Designation used in PCT/EP04 012857) | Sequences and chemical structures |
|---|---|---|
| Dbait32 | DRIL32 | 5'ACGCACGGGTGTTGGGTCGTTTGTTCGGATCT3'<br>3'TGCGTGCCCACAACCCAGCAAACAAGCCTAGA5' |
| Dbait32H-po | DRIL32po-PEG | 5'ACGCACGGGTGTTGGGTCGTTTGTTCGGATCT3' ⎞<br>3'TGCGTGCCCACAACCCAGCAAACAAGCCTAGA5' ⎠ |
| Dbait32H | DRIL32-PEG | 5'ACGCACGGGTGTTGGGTCGTTTGTTCGGATCT3' ⎞<br>3'TGCGTGCCCACAACCCAGCAAACAAGCCTAGA5' ⎠ |
| Dbait24H | DRIL24-PEG | 5'ACGCACGGGTGTTGGGTCGTTTGT3' ⎞<br>3'TGCGTGCCCACAACCCAGCAAACA5' ⎠ |
| Dbait16H | DRIL16-PEG | 5'ACGCACGGGTGTTGGG3' ⎞<br>3'TGCGTGCCCACAACCC5' ⎠ |
| Dbait8H | DRIL8-PEG | 5'ACGCACGG3' ⎞<br>3'TGCGTGCC5' ⎠ |
| Dbait32ss | DRIL32ss | 5'ACGCACGGGTGTTGGGTCGTTTGTTCGGATCT-3' |
| Dbait32-T4 | DRIL32-T4 | 5'ACGCACGGGTGTTGGGTCGTTTGTTCGGATCT ⎞ $T_4$<br>3'TGCGTGCCCACAACCCAGCAAACAACCCTAGA ⎠ |
| Dbait32C | DRIL32-2xPEG | ⎛ 5'ACGCACGGGTGTTGGGTCGTTTGTTCGGATCT3' ⎞<br>⎝ 3'TGCGTGCCCACAACCCAGCAAACAAGCCTAGA5' ⎠ |
| Dbait32Hc-5'5' | DRIL32s33-PEG | 5'ACGCACGGGTGTTGGGTCGTTTGTTCGGATCT3' ⎞<br>5'C3'-3'GATCCGAACAAACGACCCAACATCCGTGTCG5' ⎠ |
| Dbait32-NH2 | DRIL32-NH2 | 5'ACGCACGGGTGTTGGGTCGTTTGTTCGGATCT3'-$NH_2$ ⎞<br>3'TGCGTGCCCACAACCCAGCAAACAAGCCTAGA5'-$NH_2$ ⎠ |
| Dbait32H-FITC<br>Dbait32H-Cy3<br>Dbait32H-Biot | DRIL32-FITC<br>DRIL32-Cy3<br>DRIL32-Biot | 5'ACGCACGGGTGTTGGGTCGTTTGTTCGGATCt3' ⎞<br>3'TGCGTGCCCACAACCCAGCAAACAAGCCTAGA5' ⎠<br>t = fluorescein (FITC), cyanine 3 (Cy3) or biotin (BIOT)-tagged T |
|  |  | t = fluorescein (FITC), cyanine 3 (Cy3) or biotin (BIOT)-tagged T |

Debait32 (SEQ ID NO: 1), Dbait32H-po (SEQ ID NO: 1), Dbait32H (SEQ ID NO: 1), Dbait24H (SEQ ID NO: 2), Dbait16H (SEQ ID NO: 3), Dbait8H (SEQ ID NO: 4), Dbait32ss (SEQ ID NO: 1), Dbait32-T4 (SEQ ID NO: 1), Dbait32C (SEQ ID NO: 1), Dbait32Hc-5'5' (SEQ ID NO: 5), Dbait32-NH2 (SEQ ID NO: 1), Dbait32H-FITC (SEQ ID NO: 1), Dbait32H-Cy3 (SEQ ID NO: 1), Dbait32H-Biot (SEQ ID NO: 1).

TABLE 1.2

Sequences and chemical structures of additional Dbait molecules.
Dbait 32Ha (SEQ ID NO: 6), Dbait32Hb (SEQ ID NO: 5), Dbait32Hc (SEQ ID NO: 6) and Dbait32Hd (SEQ ID NO: 7) have the same base composition but in different order as compared to the sequence of Dbait32H (SEQ ID NO: 1) (cf. table 1.1). The uppercase letters are nucleotides with phosphodiester backbone. The bold uppercase letters are nucleotides with phosphorothioate backbone. The bold lowercase letters are nucleotides with methylphosphonate backbone. Half circle solid line symbolizes hexaethyleneglycol linker. Various labelled (cyanine 3 or 5, FITC) Dbat8Hc (SEQ ID No: 8), Dbait32Hc (SEQ ID NO: 6) and Dbait32Hd (SEQ ID NO: 7) molecules are indicated

| Dbait molecules (Designation used in the current CIP) | DRIL molecules (Designation used in PCT/EP04 012857) | Sequences and chemical structures |
|---|---|---|
| Dbait32Ha | | 5'GCTGTGCCCACAACCCAGCAAACAAGCCTAGA3'<br>3'CGACACGGGTGTTGGGTCGTTTGTTCGGATCT5' |
| Dbait32Hb | | 5'GCTAGGCTTGTTTGCTGGGTTGTAGGCACAGC3'<br>3'CGATCCGAACAAACGACCCAACATCCGTGTCG5' |
| Dbait32Hc | | 5'GCTGTGCCCACAACCCAGCAAACAAGCCTAGA3'<br>3'CGACACGGGTGTTGGGTCGTTTGTTCGGATCT5' |
| Dbait32Hd | | 5'GCTAGGTCTGTTTGGTGGCTTTGCAGTGGCAC3'<br>3'CGATCCAGACAAACCACCGAAACGTCACCGTG5' |
| Dbait32Hc-3'mp | | 5'GCTGTGCCCACAACCCAGCAAACAAGCCTAGA3'<br>3'cgaCACGGGTGTTGGGTCGTTTGTTCGGATCT5' |
| Dbait32Hc-5'3'mp | | 5'gctGTGCCCACAACCCAGCAAACAAGCCTAGA3'<br>3'cgaCACGGGTGTTGGGTCGTTTGTTCGGATCT5' |
| Dbait32Hcss-po | | 5'GCTGTGCCCACAACCCAGCAAACAAGCCTAGA3' |
| Dbait8Hc-Cy3 | | 5'GCTGTGCA3'<br>3'CGACACGt5'<br>t = cyanine 3 (Cy3)-tagged T |
| Dbait32Hc-Cy3<br>Dbait32Hc-Cy5 | | 5'GCTGTGCCCACAACCCAGCAAACAAGCCTAGA3'<br>3'CGACACGGGTGTTGGGTCGTTTGTTCGGATCT5'<br>t = cyanine 3 (Cy3) or Cyanine 5 (Cy5)-tagged T |
| Dbait32Hd-FITC | | 5'GCTAGGTCTGTTTGGTGGCTTTGCAGTGGCAC3'<br>3'CGACACGGGTGTTGGGTCGTTTGTTCGGATCT5'<br>t = fluorescein (FITC)-tagged T |

Dbait32Ha (SEQ ID NO: 6), Dbait32Hb (SEQ ID NO: 5), Dbait32Hc (SEQ ID NO: 6), Dbait32Hd (SEQ ID NO: 7), Dbait32Hc-3'mp (SEQ ID NO: 6), Dbait32Hc-5'3'mp (SEQ ID NO: 6), Dbait32Hcss-po (SEQ ID NO: 6), Dbait8Hc-Cy3 (SEQ ID NO: 8), Dbait32Hc-Cy3 (SEQ ID NO: 6), Dbait32Hc-Cy5 (SEQ ID NO: 6), Dbait32Hd-FITC (SEQ ID NO: 7).

TABLE 1.3

Sequences and chemical structures of 64-bp Dbait64 (SEQ ID NO: 9) and Dbait64L (SEQ ID NO: 9) molecules previously named DRIL64 and DRIL64-PEG molecules, respectively.

| Dbait molecules | Sequences and chemical structures |
|---|---|
| Dbait64 | 5'ACGCACGGGTGTTGGGTCGTTTGTTCGGATCTACGCACGGTCGTTTGTTCGGTGTTGGCGATCT3'<br>3'TGCGTGCCCACAACCCAGCAAACAAGCCTAGATGCGTGCCAGCAAACAAGCCACAACCGCTAGA5' |
| Dbait64L | 5'ACGCACGGGTGTTGGGTCGTTTGTTCGGATCT_____ACGCACGGTCGTTTGTTCGGTGTTGGCGATCT3'<br>3'TGCGTGCCCACAACCCAGCAAACAAGCCTAGA_____TGCGTGCCAGCAAACAAGCCACAACCGCTAGA5' |

Dbait64 (SEQ ID NO: 9), Dbait64L (SEQ ID NO: 9)
The uppercase letters are nucleotides with phosphodiester backbone.
The bold uppercase letters are nucleotides with phosphorothioate backbone.
Solid line symbolizes a hexaethyleneglycol linker.

All Dbait molecules were made by automated solid phase oligonucleotide synthesis (Eurogentec, Belgium). They were purified by denaturing reverse phase HPLC. Denaturing capillary gel electrophoresis. MALDI-TOF/LC-MS were used for quality control. More than 90% of oligonucleotides are full length. All samples were lyophilized before shipping.

Upon reception, all samples were dissolved in bi-distilled water. The concentrations of Dbait molecules were calculated from absorbance at 260 nm (Cantor & Warshaw, 1970) under denaturing condition (60° C.-90° C. depending on the thermal stability of Dbait molecules). The concentrations of fluorescent dye tagged Dbait molecules were calculated from absorbance at the appropriate wavelength of the particular dye (FITC: $\epsilon$=80000 $M^{-1} \cdot cm^{-1}$ at 490 nm; Cy3: $\epsilon$=150000 $M^{-1} \cdot cm^{-1}$ at 550 nm; Cy5: $\epsilon$=250000 $M^{-1} \cdot cm^{-1}$ at 650 nm). The dumbell dsDNA fragment (Dbait32C) (SEQ ID NO: 1) was prepared by annealing and ligation by DNA T4 ligase (BioLabs) of two semi hairpins carrying hexaethyleneglycol linker and with 3'-protruding and complementary ends.

Based on the thermodynamic and kinetic considerations, the following protocols were used for preparing the samples of Dbait molecules, according to their molecularity:

For bi-molecular Dbait molecules (Dbait32 (SEQ ID NO: 1), Dbait32-NH2 (SEQ ID NO: 1), Dbait64 (SEQ ID NO: 9) and Dbait64L (SEQ ID NO: 9)):

The mixture of 1:1 stock solution (highest concentration possible) of each strand in bi-distilled water has to be heated at 90° C. for 5 minutes for complete denaturation of each strand. The annealing was carried out by smooth return to room temperature (the samples are typically left in water bath) and the resulting duplex molecules were stored in aliquot at −20° C.

For mono-molecular Dbait molecules (hairpin):

The solution containing 200 µM of hairpin Dbait molecules in bi-distilled water has to be heated at 90° C. for 5 minutes for complete denaturation. The annealing has to be carried out by chilling the samples into ice-water (0° C.). Storage of aliquots was at −20° C.

Example 2

Biochemical Analysis of Dbait Molecules

As the first step to dissect the mechanism of action of Dbait molecules, a series of band-shift assays were carried out with different $^{32}$P radio-labelled Dbait molecules in the presence of nuclear protein extracts from Hep2 cells according to standard protocol. Typically, 10 nM $^{32}$P radio-labelled Dbait molecules were incubated in the presence of various concentrations of nuclear proteins (0, 10, 20, 40, 80, 160, and 320 ng/µL) at 30° C. for 10 minutes in TBE buffer. Then the samples were loaded on a 5% acrylamide native gel. The electrophoresis was run at 95V for 2 hours at 4° C. The gel was dried and scanned by phosphorimager (Molecular Dynamics).

FIG. 1.1 shows the retarded band pattern of the titration of Hep2 nuclear protein extracts with various Dbait molecules of different lengths. Except the shortest 8 bp long Dbait molecule (Dbait8H) (SEQ ID NO: 4), up to 2 retarded bands were observed for longer Dbait molecules:. One retarded band was observed for the 16-, 24-bp long Dbait molecules (Dbait16H (SEQ ID NO: 3) and Dbait24H (SEQ ID NO: 2)), whereas two retarded band were observed for 32-bp long Dbait molecules (Dbait32H (SEQ ID NO: 1), Dbait32H-po (SEQ ID NO: 1) and Dbait32 (SEQ ID NO: 1)). For 32-bp Dbait molecules, the intensity of the retarded band 1 increases and then decreases as the concentration of protein increases, while the intensity of the retarded band 2 increases as a function of the concentration of nuclear protein extracts.

The combination of immunobinding and band-shift assays with mouse monoclonal anti-Ku70 antibody (Santa Cruz Biotechnology) revealed that retarded bands 1 and 2 contain the Ku complex Band 1 and 2 were further shifted into band1* and 2* upon addition of anti-Ku70 antibody (FIG. 1.2). It is likely that band 1 has one Ku70/80 complex bound to the 16 to 32-bp Dbait, whereas the band 2 has two Ku70/80 complexes bound to the 32-bp Dbait molecules. Control experiments performed with purified Ku proteins confirmed this interpretation.

The identification of Ku proteins clearly indicates that Dbait molecules interact with NHEJ machinery in a length-dependent manner.

DNA end-joining was monitored by incubating $^{32}$P-labeled 605-bp linear DNA fragments with Hep2 nuclear extract in the presence of various Dbait molecules. Ligation products migrate as dimers, trimers or tetramers, starting 605 bp monomer.

FIG. 1.3 shows the effect of various Dbait molecules on DNA end-joining reaction in the nuclear extracts of Hep2 cells. Approximately 16% of the $^{32}$P-labeled blunt linear duplex DNA molecules were ligated into dimers and trimers during the first 2 h of incubation. The amount of high molecular weight ligation products increased up to 30% of the total input DNA after 16 h. When Dbait32H (SEQ ID NO: 1) was added to the reaction in a 100-fold molar excess compared to the linear $^{32}$P-labeled fragment the reaction was strongly inhibited. Similar inhibition of end-joining activity was also observed with extracts prepared from HeLa cells (data not shown). In most experiments, Dbait32H (SEQ ID NO: 1) was added simultaneously with the labeled DNA fragments to the nuclear extract. When Dbait32H (SEQ ID NO: 1) was incubated with the extract for 30 min before addition of fragments, the extent of inhibition was similar. By contrast, when Dbait32H (SEQ ID NO: 1) was added 30 min after the nuclear extract there was no inhibition of the ligation (data not shown). These data indicate that Dbait molecules are competitors of DNA end-joining reaction, but do not displace the bound complex.

Various Dbait molecules were tested for their effect on the cell-free assay by adding the molecules to nuclear extract and incubating for 2 h with the DNA fragments. Ligation was largely unaffected by the short molecule (Dbait8H) (SEQ ID NO: 4), the single strand 32-nt long molecule (Dbait32ss) (SEQ ID NO: 1), or the dumbell molecule (Dbait32C) (SEQ ID NO: 1). Dbait24H (SEQ ID NO: 2) and Dbait16H (SEQ ID NO: 3), which bind only one Ku heterodimer, inhibited the ligation as efficiently as Dbait32H (SEQ ID NO: 1). These data indicate that DNA fragment religation is strongly inhibited by Dbait molecules that are able to recruit Ku.

DNA-PK activity was monitored using the kit SignaTECT DNA-dependent Protein Kinase Assay System (Promega, Madison, USA). Increasing amounts of Hep2 nuclear extract (cleaned of endogenous DNA by DEAE-Sepharose filtration) were assayed in the presence of 250 nM Dbait. Extract, biotinylated peptide substrate and various amount of nuclear extract were incubated 5 minutes at 30° C. with $(\gamma\text{-}^{32}P)$ATP according to manufacturer indications. The biotinylated substrate was capture on streptavidine membrane, washed and counted in a scintillation counter. Percentage of phosphorylation is calculated by dividing the bound radioactivity by the total count of $(\gamma\text{-}^{32}P)$ATP per sample. Reactions (10 µl) were carried out in 60 mM KOAc, 100 µg/ml BSA, 0.5 mM $Mg(Cl)_2$, 1 µl T4 DNA ligase 10× buffer (Promega, Madison, USA). Nuclear extract and Dbait were incubated 2 minutes before addition of $^{32}$P-labeled DNA (10 ng). Samples were incubated various time at 37° C. before ligation being stopped by 20 mM EDTA and 1 mg/ml Proteinase K addition. Ligation products were analyzed by electrophoresis through 0.7% agarose gels followed by autoradiography and quantification by phosphorimaging.

FIG. 1.4 shows DNA-dependent protein kinase (DNA-PK) activity of a number of 2 µg Dbait molecules with various lengths, sequences and chemical structures including modified backbones, in 1.5 µg of Hep2 nuclear protein extract. The kinase activity depended directly on the length and structure of the double-stranded 'stem' of the Dbait molecule. High DNA-PK activation was observed with the 32-bp long Dbait molecules which were nound by two Ku dimmer complexes. The Dbait molecules that bound only one Ku dimer (Dbait16H (SEQ ID NO: 3) and Dbait24H (SEQ ID NO: 2)) were as inefficient as the short Dbait8H (SEQ ID NO: 4) that dID NO:t bind Ku. Similarly, the single strand Dbait32ss (SEQ ID NO: 1)/Dbait32css (SEQ ID NO: 6) and dumbell Dbait32C(SEQ ID NO: 1), which have no free double-stranded ends, dID NO:t activate DNA-PK. In addition, various backbone modifications (phosphothioate, methyphosphonate, 3'-3' linkage) at the free blunt end (up to 3-bp), as well as the internally tagged ligands (e.g. fluorescent dyes), are capable of activating DNA-PK activity. It is worthy noticing that the DNA-PK activity does not significantly, if any, depend on the sequence of Dbait molecules, as shown by Dbait32H (SEQ ID NO: 1), Dbait32Hb (SEQ ID NO: 5), Dbait32Hc (SEQ ID NO: 6) and Dbait32Hd (SEQ ID NO: 7).

This simple cell free DNA-PK activity assay points out that only the length (at least about 32-bp) and the double stranded DNA with a free end of Dbait molecules are required for the kinase activation, regardless their sequence and chemical modifications to some extent. This is consistent with the implication of DNA-PK in the NHEJ pathway, a sequence independent DNA end joining mechanism.

Example 3

In Vitro Activity of Dbait Molecules

The activity of Dbait molecules in cultured cells was studied by clonogenic survival assay in two radio-resistant human cancer cell lines derived from a female cervix carcinoma (HeLa) and from HNSCC (Hep2) in association with ionizing radiation, by the inhibition of illegitimate integration of exogenous DNA fragment and by detecting the persisting DSB foci after irradiation in the cells transfected by Dbait molecules.

Established human cell lines Hep2 (head and neck squamous cell carcinoma, HNSCC), LU1205 and SK28 (melanomas) were used for animal studies. Studies of cells in culture were performed using Hep2, HeLa S3 (epithelia cervical carcinoma), MO59K and MO59J (glioblastoma). Cells were grown at 37° C. in monolayer cultures in complete DMEM containing 10% heat-inactivated fetal bovine serum (FBS; Invitrogen, Cergy Pontoise, France) and antibiotics (100 µg/ml streptomycin and 100 µg/ml penicillin) under conditions of 100% humidity, 95% air and 5% $CO_2$. LU1205 were grown in MCDB containing 4% heat-inactivated FBS, 1% glutamine and antibiotics (100 µg/ml streptomycin and 100 µg/ml penicillin).

Exponentially growing cells in six-well plates were harvested and incubated with 700 ml of complete DMEM containing a mixture of Dbait molecules and Superfect reagent (Qiagen, Courtaboeuf, France) in a ratio of 10 µl Superfect per µg DNA. After 5 h at 37° C. under standard conditions, the cells were washed with PBS and complete DMEM was added. Where indicated, cells were exposed to irradiation either in one session (10 Gy) 5 h after the beginning of transfection or in four sessions of 0.5 Gy administered with a $^{137}$Cs unit (1 Gy/min) 3, 4, 5 and 6 h after the beginning of transfection and allowed to grow for two weeks. When plasmid integration was measured, 2 µg of plasmid was added to Dbait transfection and puromycin (1.7 µg/ml) was added to the growth medium 48 h after transfection. Plasmid transfection efficiency was estimated by analyzing 10,000 cells for GFP expression on a FACScan flow cytometer (FACSalibur, Beckton-Dickinson, USA).

3.1) Induced Cell Lethality

Upon 8 hours transfection of Dbait molecules in Hela cells and four irradiation with 0.5 Gy fractionated irradiation spaced 2 hours (4×0.5 Gy), performed with γ-rays from a $^{137}$Cs source, a significant reduction of clonogenic survival was observed as compared to untransfected cells. The results are given on FIG. 2.1 wherein Panel A gives the dose-dependence of normalized survival clone number in the presence of Dbait32 (SEQ ID NO: 1) and Dbait32H (SEQ ID NO: 1), and Panel B, the normalized survival clone number in the presence of different Dbait molecules at 83 nM (concentration in culture medium). Cell culture was in MEM supplemented with 10% serum. Superfect (Qiagene) was used as transfection agent according to the manufacturer's instruction. Clonogenic survival was estimated as the number of treated cells forming colonies on the number of untreated cells.

The effect depends on the length and the chemical nature of Dbait molecules in a dose-dependent manner. In this assay, the hairpin Dbait molecules (Dbait32H (SEQ ID NO: 1), Dbait32-T4 (SEQ ID NO: 1) and Dbait24H (SEQ ID NO: 2)) and the linear double-stranded Dbait molecules (Dbait64 (SEQ ID NO: 9) and Dbait64L (SEQ ID NO: 9)) significantly reduced clonogenic survival. It is worth to note that the dumbell Dbait32C (SEQ ID NO: 1) molecule which lacks free dsDNA ends (capped by hexaethyleneglycol linker at both ends) dID NO:t exhibit any effect. The chemical nature of loop dID NO:t matter (Dbait32H (SEQ ID NO: 1) versus Dbait32-T4 (SEQ ID NO: 1)). These observations indicate that some of the Dbait molecules can effectively sensitize cells to ionizing radiation in cultured cells.

FIG. 2.2 confirms the previous observations, and provides additional data that either single strand or short 8-bp Dbait molecules dID NO:t have any effect. In addition, it shows that the effect was not sequence-dendent (Dbait32H (SEQ ID NO: 1) versus Dbait32Hc (SEQ ID NO: 6)).

TABLE 2

Cell survival in DNA-PK competent cell (MO59K) and DNA-PK deficient cell (MO59J) after treatment with radiation and Dbait.

| Cell line | treatment | | survival |
|---|---|---|---|
| | Irradiation | Transfection | % |
| MO59K | no | no | 100 (4.41) |
| | 10 Gy | no | 9.83 (0.61) |
| | 10 Gy | Dbait32Hc | 3.47 (1.01) |
| MO59J DNA-PK-null | no | no | 100 (2.97) |
| | 10 Gy | no | 3.97 (0.38) |
| | 10 Gy | Dbait32Hc | 3.98 (0.35) |

Cells were diluted and plated to form colonies on flasks that were then either irradiated with 10 Gy and/or transfected with 2 µg Dbait32Hc (SEQ ID NO: 6). When both treatments were conjugated the irradiation was performed 5 h after transfection. Survival is calculated as the number of cells forming clones after treatment divided by the number of cells forming clones in the non-treated sample. The mean value and the standard deviation (in brackets) were calculated from three independent experiments.

The effect of Dbait32Hc (SEQ ID NO: 6) transfection on DNA-PK wild-type and mutant cell survival after γ-irradiation was estimated by colony formation. Survival after irradiation decreased from 9.83% in untransfected MO59K cells to 3.47% in Dbait32Hc (SEQ ID NO: 6)-transfected cells. In the corresponding DNA-PK-null mutant cell line, MO59J, by contrast, survival was unaffected by transfection with Dbait32Hc (SEQ ID NO: 6). The level of survival was similar in the irradiated and Dbait32Hc (SEQ ID NO: 6)-transfected wild-type cell line to that observed in the DNA-PK-null mutant cells after only irradiation (3.47% compared to 3.97%). This suggests that Dbait32Hc (SEQ ID NO: 6) inhibits DNA-PK-dependent repair in the wild-type transfected cells.

3.2) Inhibition of Illegitimate Integration of Exogenous DNA by Dbait Molecules

Ionizing radiation is known to improve illegitimate integration of exogenous DNA, a process termed radiation-enhanced integration. Hela cell culture was used for this assay. Cells were transfected during 8 hours by 2 µg of a linear plasmid carrying the gene coding for neomycin resistance, and three different ratio of DNA/superfect (1:2, 1:5, 1:10). During transfection time, the cells were exposed to different irradiation protocols: no irradiation, one single irradiation of 1 Gy and 2 Gy, as well as a 2 Gy irradiation delivered by fractionated doses of 0.5 Gy every 2 hours (4×0.5 Gy). The integration of the plasmid was monitored by selection of Neo$^R$ cells growing in a medium containing 0.6 mg/ml of G418. Plasmid integration was significantly enhanced by the fractionated irradiation protocol. When 2 µg of Dbait32H (SEQ ID NO: 1) molecules were added to the transfection mix, the radiation-enhanced integration was abolished (FIG. 2.3).

FIG. 2.4 provides additional data which shows that only the 32-bp Dbait molecules (Dbait32H (SEQ ID NO: 1) and Dbait32Hc (SEQ ID NO: 6)) were capable of inhibiting radiation-enhanced illegitimate integration of a circular plasmid carrying the gene conding for puromycin resistance, whereas shorter Dbait molecules (Dbait16H (SEQ ID NO: 3), Dbait8H (SEQ ID NO: 4)), single strand or dumbell Dbait molecules (Dbait32ss (SEQ ID NO: 1) and Dbait32C (SEQ ID NO: 1)) were not effective. Wortmann (Wort) and NU7026 (NU) which are known inhibitors of PI3K (including DNA-PK) were used as control.

These experiments showed that the radiation-enhanced illegitimate integration of exogeneous DNA which required Ku, DNA-PK and ATM proteins (Nimura et al., 2002) is inhibited by 32-p Dbait molecules in a sequence-independent way, as expected, as the mechanism of action of these Dbait molecules act through the kidnapping the proteins involved in a NHEJ pathway.

3.3) Persistence of DSB Sites after Irradiation in the Cells Transfected by Dbait Molecules DSB sites in nuclei can be monitored by immunofluorescence of γ-H2AX antibody which binds on the phosphorylated H2AX (a variant of the histone H2A). Most of the γ-H2AX foci appear rapidly after irradiation and disappeared as DSB repair process progressed.

Transfection and irradiation protocols were similar to those described above. For immunodetection, the cells were grown on surface coverslip in 5 cm diameter Petri dishes, transfected with 2 µg Dbait32H-FITC (SEQ ID NO: 1) molecules labeled with FITC with Superfect (Qiagene) according to the manufacturer's instruction. Four hours after the beginning of the transfection, cells were irradiated (2 Gy), then rest for 2 hours in the medium at 37° C. After 3 washing cycles, the cells were fixated with 2% PFA for 10 minutes. After one additional washings, the presence of γ-H2AX was detected with rabbit anti-γ-H2AX antibody (4411-PC, Trevigen) diluted 1/100 in 1×PBS, 1% BSA. Cells were washed three times with 1×PBS, 0.5% TritonX-100, then incubated for 1 hour at room temperature with rhodamine-conjugated goat anti-rabbit antibodies diluted 1/100 in 1×PBS, 1% BSA. Cells were visualized by epifluorescence microscopy.

FIG. 2.5 shows the results obtained with Hela cells transfected by fluorescent Dbait32H-FITC (SEQ ID NO: 1) molecules at 2 hours after 2 Gy irradiation. Left panel: fluorescence of Dbait32H-FITC (SEQ ID NO: 1) (bright dots and patches) and DBS foci detected by immunofluorescence of γ-H2AX antibody in nuclei; Right panel: the same image of nuclei with DSB foci detected by immunofluorescence of γ-H2AX antibody and DAPI counterstaining. The arrows at the lower left corner show the absence of Dbait32H-FITC (SEQ ID NO: 1) and γ-H2AX signal in nucleus. The arrows at the upper right corner show the co-localized Dbait32H-FITC (SEQ ID NO: 1) and γ-H2AX signals. As shown on FIG. 2.5, DSB sites persisted in Hela cells transfected by Dbait32H-FITC (SEQ ID NO: 1) molecules two hours after irradiation (2 Gy), as shown by double fluorescent labelling with Dbait32H-FITC (SEQ ID NO: 1) and that of γ-H2AX antibody. It is worth to note that the DSB foci were almost undetectable in the cells that were not efficiently transfected by Dbait32H-FITC (SEQ ID NO: 1). These data suggest that DSB repair was impaired in the cells efficiently transfected by Dbait32H (SEQ ID NO: 1), while the DNA repair was complete in the cells less well transfected.

Western blotting was performed using rabbit monoclonal anti-phospho Thr68-Chk2 (Cell Signaling Technology, Denver, USA), monoclonal anti-β-actin clone AC-15 (Sigma, Miss., USA), anti-H2AX (Cell Signaling Technology, Denver, USA) and a mouse anti-phospho-Histone H2AX (Ser139) (Upstate, Tempcula, Calif., USA).

FIG. 2.6 upper panel shows the western blot analysis of the phosphorylated form of histone H2AX (γ-H2AX) as compared to the total H2AX protein phosphorylation of the histone H2AX by PIKKs. Hep2 cells were transfected 5 hours with various Dbait molecules 32Hc (SEQ ID NO: 6), 24H (SEQ ID NO: 2), 16H (SEQ ID NO: 3) and 8H (SEQ ID NO: 4) for 5 h, or not transfected. They were irradiated at the end of transfection, incubated for one hour and then analyzed. It shows that Dbait32Hc (SEQ ID NO: 6) greatly enhanced the phosphorylated form of H2AX (γ-H2AX) as compared to the control (both irradiated cells, or none). Other shorter Dbait molecules had much less or none effect.

To investigate the effect of Dbait on ionizing radiation-induced g-H2AX foci formation and loss, Dbait32H-Cy3 (SEQ ID NO: 1) were transfected in the Hep2 cells by superfect (Qiagen). Transfected or untransfected Hep2 cells were irradiated at 10 Gy. Cells were fixed at different times (0 min, 30 min, 1 hour, 5 hours, 24 hours, 48 hours, 72 hours and 7 days). Primary mouse monoclonal antibody for g-H2AX (ser139) (Upstate, Tempcula, Calif., USA) was used in 1/500 dilution and incubated for 2 hours at 0° C., then washed by PBS buffer and incubated with Alexa 488-conjugated second antibody anti mouse IgG (Molecular Probe, Eugene, Oreg., USA) diluted in 1/200 for 1 hour in dark room.

The kinetics of the persistence of DSB sites was revealed by γ-H2AX in the irradiated cells by FACScan flow cytometer (FACSalibur, Beckton-Dickinson, USA). FIG. 2.6 lower panel shows that the level of γ-H2AX remained high and long in the Dbait32H (SEQ ID NO: 1) transfected cells as compared to the controls (either irradiated but untransfected or untreated cells). This experiment indicated that Dbait32H (SEQ ID NO: 1) substantially retarded the repair of ionizing radiation-induced DSBs.

Example 4

Effects of Dbait Molecules in GMA32 Cell Line and their Association with Irradiation or Mitotic Inhibitors The GMA32 Chinese hamster fibroblast cells permissive of DNA breaks were maintained in MEM medium (Gibco)

supplemented with 1 mM sodium pyruvate, 2 mM glutamine, 1×MEM non essential amino acids, 1× penicillin/streptomycin and 10% horse serum. Typically, $2\times10^5$ to $4\times10^5$ cells were seeded in medium without antibiotics, in 5 cm diameter Petri dishes 24 hours before the transfection of different Dbait molecules (4.5 μg) with lipofectamine 2000 (LifeTechnologies) as transfection agent (in a 1:3 ratio), according to the manufacturer's instructions. At the end of the transfection the cells were either irradiated (4 Gy) or treated with mitotic inhibitors: nocodazole (200 nM), navelbine (100 nM) or taxol (200 nM).

About 16 hour later the drug was removed and the cells were allowed to recover. Cell irradiation was performed with γ-rays from a $^{137}$Cs source. After a 24 hours recovery, the cells were collected and used either for FACS, western blot analyses or to determine the clonogenicity (survival) and the effect of each treatment.

FIG. 3.1 shows FACS analyses of the untreated GMA32 cells, the cells transfected alone, or transfected with different Dbait molecules by lipofectamine, but without further irradiation or mitotic inhibitor treatment. The M1 phase represents the percentage of cells in sub-G1 stage indicative of cell death. Significant cell death was observed only in the presence of double-stranded Dbait32 (SEQ ID NO: 1) and hairpin Dbait32H (SEQ ID NO: 1) molecules, whereas hairpin Dbait16H (SEQ ID NO: 3) and single-strand Dbait32ss (SEQ ID NO: 1) induced intermediate and moderate cell death, respectively. The shortest hairpin Dait8H (SEQ ID NO: 4) failed to trigger cell death as compared to the control (cells transfected by lipofectamine alone).

The experiments were performed with a FACS calibur flow cytometer (Becton Dickinson). Cells were collected, suspended in 1 ml of cold GM buffer (6.5 mM glucose, 137 mM NaCl, 5.4 mM KCl, 2 mM Na2HP04, 1 mM KHPO4, 0.5 mM EDTA), and stored at 4° C. for at least 2 hours after addition of 3 ml of cold 100% ethanol.

At that stage, cells were eventually washed with 1×PBS, then stained for 30 minutes at room temperature in PI solution (50 μg/ml propidium iodide, 25 μg/ml RNase A in 1×PBS buffer). 10,000 events were analyzed with Cellquest software, and cell aggregates were gated out. The percentage of cells with a sub-G1 content of DNA was scored.

Under the same conditions, the immunodetection of DSB foci of γ-H2AX phosphorylated on serine 139 by γ-H2AX labeling (bright dots or patches in nuclei) was performed in the untreated GMA32 cells, the cells transfected alone, or transfected with different Dbait molecules by lipofectamine. The counterstaining of cell membranes and nuclei were achieved by FITC-DiOC6 and DAPI. Similar effects of Dbait molecules were observed (FIG. 3.2). This experiment shows that both double-stranded Dbait32 (SEQ ID NO: 1) and hairpin Dbait32H (SEQ ID NO: 1) can effectively trigger similar cell response as if DNA damages were occurred in nuclei. This provides visual evidence that these Dbait molecules can be used for trapping proteins involved in DSB repair via NHEJ pathway.

For immunodetection, the cells were grown on coverslip in 5 cm diameter Petri dishes 24 hours before the transfection with different Dbait molecules. One day after the transfection, FITC-DiOC6 (Molecular probes) was added in the medium 5 minutes at 37° C. (to counterstain the membranes). After 3 washing cycles, the cells were fixated with 4% PFA for 20 minutes.

After additional washing, γ-H2AX phosphorylated on serine 139 (γ-H2AX) was detected with, rabbit anti-γ-H2AX antibody (4411-PC, Trevigen) diluted 1/100 in 1×PBS, 1% BSA. Cells were washed three times with 1×PBS, 0.5%, TritonX-100, then incubated for 1 hour at room temperature with goat anti-rabbit antibodies Alexa 594 (Molecular Probes) diluted 1/100 in 1×PBS, 1% BSA. Cells were visualized by epifluorescence microscopy.

Further experiment was carried out in order to look for evidence of DNA damage signaling. The protein p53 is a well known major protein in mediating DNA damage signaling and in coordinating appropriate responses (DNA repair, apoptosis, etc.) by changing its phosphorylation status. In particular, the phosphorylation of serine 15 residue is involved in the interaction with MDM2 protein which acts as a feed back control Thus, the phosphorylation status of the serine 15 of p53 was assessed by Western blot. FIG. 3.3 shows that the p53 serine 15 was highly phosphorylated when cells were transfected by either double-stranded Dbait32 (SEQ ID NO: 1) or hairpin Dbait32H (SEQ ID NO: 1) molecules, whereas the shorter hairpin Dbait16H (SEQ ID NO: 3) induced moderate phosphorylation. Neither the shortest Dbait8H (SEQ ID NO: 4) nor single strand Dbaut32ss (SEQ ID NO: 1) molecules were able to induced significant phosphorylation on the serine 15 of p53 protein.

This experiment provides additional evidence that the presence of both double-stranded Dbait32 (SEQ ID NO: 1) and hairpin Dbait32H (SEQ ID NO: 1) in GMA32 cells was detected as DNA damage and induced the signal to transducer responses such as p53 protein phosphorylation, likely through ATM activation pathway.

For Western blot analysis, cells were lysed in Laemmli buffer. Equal amounts of lysates were resolved in 12% polyacrylamide gels. Proteins were transferred to nitrocellulose membranes, which were blocked with 5% nonfat milk (1 hour) before overnight incubation with anti-p53Ser15 antibody (9284, Cell Signaling) diluted 500 folds in TBST buffer (10 mM Tris-HCl pH7.5, 150 mM NaCl, 0.1% Tween 20) containing 5% nonfat milk. Blots were then incubated with horseradish peroxidase-conjugated goat anti-rabbit IgG secondary antibodies (P0448, Dako) diluted 1/5000 in TBST. Protein-antibody complexes were detected by enhanced chemiluminescence (RPN2106 ECL, Amersham).

The effect of radiosensitization and chemosensitization of Dbait molecules in GMA32 cells was evaluated by clonogenicity (clonal survival) assay. For the clonogenicity assay, serial dilutions were made after counting the cells to seed 5 cm Petri dishes with different amounts of cells. The number of cells range from 100-200 (control cells) to 3000 (transfected or/and treated cells). Ten days after, the cells (forming clone) were fixed with 4% paraformaldehyde (20 minutes), then colored with methylene blue (15 minutes), and the number of clone in each plate (in triplicates) was scored.

FIG. 3.4 shows that the radiosensitization to 4 Gy irradiation was observed in GMA32 cells transfected with either double-stranded Dbait32 (SEQ ID NO: 1) or hairpin Dbait32H (SEQ ID NO: 1) molecules. In addition, the chemosensitization was also observed for GMA32 cells transfected with either double-stranded Dbait32 (SEQ ID NO: 1) or hairpin Dbait32H (SEQ ID NO: 1) molecules when they were treated by mitotic inhibitors (200 nM nocodazole, 100 nM navelbine (vinorelbine) or 200 nM taxol (paclitaxel)). These drugs are known as potent inhibitors of either polymerization or depolymerization of microtubules. Dbait32 (SEQ ID NO: 1) and Dait32H (SEQ ID NO: 1) were able to enhance to cytotoxic activity of these mitotic inhibitors.

Example 5

Radiosensitization of the Treatment of Xenografted Human Tumors on Nude Mice In vivo activity of Dbait molecules in association with radiotherapy was assessed by using nude mice xenografted with human tumors by subcutaneous injection of radio-resistant cell lines (Hep2 derived from head and neck squmous cell carcinoma, HNSCC) or tumor fragments (previously obtained by subcutaneous injection of the U87 cell lines derived of glioblastoma).

Investigations were mainly carried out on the mice xenografted with radio-resistant human HNSCC tumors in order to establish proof of concept in vivo. Irradiation was performed with γ-rays from a $^{137}$Cs source with appropriate protection of mice in order to perform localized irradiation of tumors. Typical assay condition consists of intratumoral injection of an appropriate preparation of 1 nmole Dbait molecules with transfecting agents (cationic dendrimer (Superfect, Qiagene), dioctadecylamidoglycyl-spermine (DOGS, Polyplus transfection), polyethyleneimine (PEI, Polyplus Transfection) according to manufacturers instruction, 5 hours prior irradiation. A total dose of 30 Gy was delivered in 5 weeks: i) 3×2 Gy/week (about one every two days); ii) 5 Gy/week; iii) 15 Gy/2 weeks.

The size of tumor was measured 2-3 times a week. Treatment by irradiation and intratumoral injection of MEM medium (the Dbait dilution buffer), was used as a control of irradiation treatment without Dbait. The volume of tumor was calculated ($V=2 \times a \times b^2$, where a=length, b=width). The ratio of volume measured at t time over the initial volume ($V_t/V_i$) was used as indicator of tumor progression. The mice were followed up to 100 days. At least 4 independent series of six animals were tested.

The results are illustrated by FIG. 4.1 (Panel A: Untreated arm (n=38; Panel B: control arm with 20 μl culture medium (MEM)+3×2 Gy/week irradiation (n=30); Panel C: the arm with 1 nmole (20 μg) Dbait32H (SEQ ID NO: 1)+3×2 Gy/week irradiation (n=35).

MEM or Dbait32H (SEQ ID NO: 1) was delivered by intratumoral injection 5 hours prior irradiation. The fractionated irradiation dose (2 Gy) was given one of every two days, three times a week. The treatment lasted 5 weeks totaling 30 Gy irradiation. The dots represent the time course of tumor volume of each mouse. The solid lines are the best polynomial fitting. Panel D shows a Kaplan-Meyer plot of all mice of which the increase in tumor volume ($V_t/V_i$)<5.

A significant amount of data has been accumulated on the arm of Dbait32H (SEQ ID NO: 1) with 3×2 Gy/week irradiation (panel C, n=35) which clearly showed radiosensitization as compared to the control arms: untreated (panel A, n=38), MEM+3×2 Gy (panel B, n=30). The Man and Whitney statistical test gave p-value=0.00067 for the arm of Dbait32H (SEQ ID NO: 1)+3×2 Gy versus MEM+3×2 Gy. The same trend was observed in a Kaplan-Meyer plot of mice with a tumor volume ($V_t/V_i$<5) smaller than five-fold the initial volume (panel D).

Further investigations were subsequently carried out on mice with xenografted human HNSCC, U87, LU1205 and SK28 tumors in order to define molecular features of Dait molecules and optimal protocol for in vivo activity. The data obtained from the studied cohort were consistent with molecular features of Dbait molecules observed in biochemical and in vitro studies (cf. examples 2, 3 and 4). In addition, it was shown that the radiosensitization is dependent on the dwell time between the intratumoral injection of Dbait32H (SEQ ID NO: 1) and the ionizing radiation: 5 hours>>1 hour.

Radio-sensitization was also observed in mice xenografted with human glioblastoma tumors. The glioblastoma is the highest grade of brain-tumor, and is characterized by its extraordinary aggressive progression with fast fatal outcome and resistance to radio- and chemotherapies. 2-3 millions of U87 cells derived from human glioblastoma was first injected subcutaneously in nude mouse. The grafted tumor was then took out and used to seed subsequently other nude mice by subcutaneous transplant of about 8 mm$^3$ glioblastoma tumor.

Table 3.1 shows data of a pilot series of xenografted human glioblastome tumors on nude mice 50% mice in the arm which received Dbait32H (SEQ ID NO: 1) (1 nmole) by intratumoral injection and irradiation (1×15 Gy/week or 3×5 Gy/week, followed by one week rest, then second treatment cycle, the total dose of ionizing radiation was 30 Gy) had tumor volume <4 cm$^3$ at the day 25 after the start of treatment, whereas 100% mice in the control arms (untreated or irradiated and injected with saline solution (PBS) had tumor volume well exceeded 4 cm3, and were killed before the end of the assay according to current regulation on animal ethics before the end of the treatment.

TABLE 3.1

Assay of radiosensitization of xenografted human glioblastoma on nude mice by Dbait32H (SEQ ID NO: 1) (1 nmole/intratumoral injection) previously named DRIL32-PEG.

| Assay groups (xenografted Glioblastome) | Number of mice where Tumor volume <4 cm$^3$ At the day 25 (6 mice per group) |
| --- | --- |
| Untreated | 0/6 |
| PBS + 1 × 15 Gy/week | 0/6 |
| Dbait32H + 1 × 15 Gy/week | 3/6 |
| PBS + 3 × 5 Gy/week | 0/6 |
| Dbait32H + 3 × 5 Gy/week | 3/6 |

Two protocols of irradiation (5 hours after intratumoral injection) were used: 1 × 15 Gy/week, or 3 × 5 Gy/week, followed by one week rest, the second treatment cycle. The total irradiation dose was 30 Gy. Control groups were the untreated or the groups received saline solution (PBS) injection.

Based on these encouraging in vivo data which provided evidence that the Dbait molecules can efficiently enhance the efficacy of radiotherapy, further experiments were designed and carried out to provide additional data related to the use of the Dbait molecules as an adjuvant agent to sensitize radiotherapy, and thus to strengthen the proof of principle of DNA bait approach in anticancer therapy.

FIG. 4.2 shows the distribution of cyanine 3 labelled Dbait32H (SEQ ID NO: 1) in Hep2 (HNSCC cell line) xenograft tumor in nude mice. 20 μg Dbait32H-Cy3 (SEQ ID NO: 1) formulated with Superfect (transfection agent) was injected into 1.5 cm$^3$ Hep2 tumor. The mice were sacrificed 6 hours after the injection. The tumors were taken out and cryo-sliced for analysis without fixing. DAPI was used for nuclei staining. The fluorescence of cyanine 3 shows that the Dbait32H-Cy3 (SEQ ID NO: 1) molecules were distributed in the tumor tissue from blood capillary vessel, and were localized in the cell nucleus.

FIG. 4.3 shows another experiment on Hep2 xenografted tumors as described in FIG. 4.1. Tumor growth was monitored during treatment and after in four groups of 10 animals with different treatments (untreated, treated with Dbait3S2H (SEQ ID NO: 1) alone, treated by irradiation alone, and the combined Dbait32H (SEQ ID NO: 1) and irradiation). Individual tumor growth is indicated for each animal. The treatment protocol was the same as described in FIG. 4.1. The experiment started when the volume of Hep2 tumors reached 150-200 mm$^3$. For each treatment session, 20 µg Dbait32H (SEQ ID NO: 1) formulated with polyethyleneimine (PEI, Polyplus Transfection, Strasbourg, France) according to the manufacturer's instruction was injected into tumor 5 hours prior 2 Gy irradiation. Tumor growth was greatly reduced in group treated by the combined Dbait32H (SEQ ID NO: 1) and irradiation as compared to the groups treated by irradiation or Dbait32H (SEQ ID NO: 1) alone.

FIG. 4.4 shows Kaplan-Meier representation of survival of mice subcutaneously xenografted by Hep2 tumor. For ethical reason, the animals were sacrificed when their tumors reached 2 cm$^3$. This end-point was used as death in survival analysis. The treatment protocol was described in FIG. 4.3. The five groups were included: untreated, mock-transfected and irradiated, treated by combined irradiation and increasing amount of Dbait32H (SEQ ID NO: 1) (20, 60 and 120 µg/session). Number of animals for each group is indicated in table 3.2. A clear dose-dependent effect was observed in the groups treated by Dbait32H (SEQ ID NO: 1) and 2 Gy irradiation. Pictures of tumors representative of the groups (untreated, treated with 20 and 60 µg Dbait32H/session associated with 2 Gy irradiation) which were taken 15 days after beginning of treatment, at the end of treatment (35 days) and 13 days after the end of treatment (35+13 days). They provided clear visual comparison of the benefit of the combined Dbait32H (SEQ ID NO: 1) and irradiation treatment.

FIG. 4.5 shows the histological analysis of xenograted Hep2 tumors at mid-course treatment (7 sessions). Tumors were taken out 20 days after beginning of various treatment protocols as indicated in FIG. 4.3. They were fixed in formalin and tissue sections were stained with hematoxylin, eosin and safran. Two tumors for each treatment protocol were analyzed by microscopy. The enhancement of necrosis and apoptosis was observed in the tumors treated by combined Dbait32H (SEQ ID NO: 1) and irradiation as compared to the tumors treated by irradiation alone.

FIG. 4.6 shows NMR imaging of xenografted Hep2 tumors at the mid-course treatment (7 sessions). Three representative cross-section images were shown with untreated tumor, tumor treated by irradiation, and by the combined Dbait32H (SEQ ID NO: 1) (20 µg/session) and irradiation (2 Gy/session). The necrotic area was more important in the tumor treated by Dbait32H (SEQ ID NO: 1) and irradiation than that treated by irradiation alone. This is consistent with the cytological analysis of tumors (cf. FIG. 4.5).

FIG. 4.7 shows Kaplan-Meier representation of survival of mice subcutaneously xenografted by Hep2, U87, LU1205 and SK28 tumors, and their controls groups (untreated, treated by irradiation alone). The protocol of Hep2 was described in FIG. 4.3. Other tumors were treated by a modified protocol where a 5 Gy fractionated irradiation was applied in three consecutive days, and followed four day rest, and the treatment was repeated once. The total irradiation dose (6×5 Gy) is equal to that of the protocol used to treat Hep2 tumor (15×2 Gy).

The benefit outcome of the combined Dbaut32H (SEQ ID NO: 1) and irradiation was observed in all four xenografted human tumors. As the underlying mechanism of action of Dbait molecules and the ubiquitous NHEJ pathway in all cells, it is anticipated that this holds true for other tumors with different histology.

Descriptive analyses of the tumor response were performed for each treatment and each tumor type. Day 1 was the day of the first treatment session. All the animals were followed for at least 150 days or until their ethical sacrifice. Median lifetime was estimated according to the Kaplan-Meier method. TGD was calculated by subtracting the mean tumor volume quadrupling time of the control group from tumor volume quadrupling times of individual mice in each treated group. The mean TGD was calculated for each treated group using the individual measurements.

Overall survival curves were assessed by Kaplan-Meier estimates and compared using the non-parametric Log Rank test since the data do not follow a normal distribution. The analysis used S-Plus 6.2 version software (MathSoft Inc., Seattle, Wash.) and statEL (ad Science, Paris, France). A global Log Rank was first performed for each group with a same tumor type. Then treatments with Dbait were compared to the mock-treated control. The number of animals (n), the relative risk (RR) and the P value are reported in Table 3.2. All tests were considered significant at the 0.05 significance level.

| Cell line | Irradiation | Dbait | Dbait concentration | Number of mice | Number of cured mice*** | Median survival time (days) | **Relative risk (P value) | **Mean TGD | **STD TGD | **Range TGD | **Mean % TGD |
|---|---|---|---|---|---|---|---|---|---|---|---|
| Hep2 | — | — | — | 21 | | 49 | C | 0 | 3.8 | −5; 12 | 100 |
| Hep2 | — | 32H | 15 × 20 µg (1 nmole) | 10 | | 55 | 0.62 (p < 0.24) | 7 | 6.7 | −3; 17 | 168 |
| Hep2 | — | 32ss | 15 × 120 µg (12 nmole) | 12 | | 46 | 0.71 (p < 0.29) | 6 | 4.9 | 0; 19 | 156 |
| Hep2 | 15 × 2 Gy | Mock | — | 17 | | 61 | C* | 12 | 14.2 | −3; 45 | 217 |
| Hep2 | 15 × 2 Gy | 32H | 15 × 20 µg (1 nmole) | 15 | | 93 | 0.42 (p < 9.55.10$^{-3}$) | 49 | 26.6 | 8; 134 | 561 |
| Hep2 | 15 × 2 Gy | 32Hc | 15 × 20 µg (1 nmole) | 11 | | 94 | 0.55 (p < 0.14) | >56 | 41.1 | 6; 139 | 629 |
| Hep2 | 15 × 2 Gy | 32H | 15 × 60 µg (3 nmole) | 20 | 3 | 129 | 0.28 (p < 4.16.10$^{-4}$) | >83 | 50.7 | −3; 139 | 880 |
| Hep2 | 15 × 2 Gy | 32Hc | 15 × 60 µg (3 nmole) | 23 | 3 | 123 | 0.36 (p < 1.2.10$^{-3}$) | >59 | 40.7 | 0; 139 | 652 |
| Hep2 | 15 × 2 Gy | 32H | 15 × 120 µg (6 nmole) | 20 | 4 | 150 | 0.18 (p < 4.10$^{-6}$) | >91 | 44.4 | 1; 139 | 952 |
| Hep2 | 15 × 2 Gy | 32ss | 15 × 120 µg (12 nmole) | 12 | | 80 | 0.57 (p < 0.15) | 29 | 19.8 | 3; 59 | 374 |
| LU | — | — | — | 21 | | 24 | C | 0 | 2.8 | −4; 4 | 100 |
| LU | 6 × 5 Gy | Mock | — | 30 | | 61 | C* | >22 | 29.2 | −7; 140 | 348 |

-continued

| Cell line | Irradiation | Dbait | Dbait concentration | Number of mice | Number of cured mice*** | Median survival time (days) | **Relative risk (P value) | **Mean TGD | **STD TGD | **Range TGD | **Mean % TGD |
|---|---|---|---|---|---|---|---|---|---|---|---|
| LU | 6 × 5 Gy | 32Hc | 6 × 60 μg (3 nmole) | 17 | 1 | 80 | 0.45 (p < 1.03.10$^{-2}$) | 27 | 13.8 | −7; 58 | 400 |
| SK | — | — | — | 21 | | 54 | C | 0 | 8.2 | −19; 14 | 100 |
| SK | 6 × 5 Gy | Mock | — | 17 | | 86 | C* | 17 | 19.5 | −3; 83 | 187 |
| SK | 6 × 5 Gy | 32H | 6 × 60 μg (3 nmole) | 10 | 2 | 176 | 0.22 (p < 1.27.10$^{-4}$) | 64 | 44.9 | −3; 156 | 422 |
| SK | 6 × 5 Gy | 32Hc | 6 × 60 μg (3 nmole) | 22 | 3 | 135 | 0.29 (p < 1.89 10$^{-3}$) | 32 | 26.9 | −8; 100 | 261 |
| SK | 6 × 5 Gy | 8H | 6 × 60 μg (3 nmole) | 8 | | 76 | 0.68 (p < 0.46) | 19 | 10.9 | 0; 40 | 194 |

Table 3.2 summarizes part of the above described data and provides the comparison of survival of xenografted animals treated by different protocols (various Dbait32 molecules + irradiation versus irradiation + Mock injection) in three human tumor cell lines subcutaneously xenografted in nude mice. In addition, it shows that the sequence of Dbait molecules does not matter as evidenced by the similar outcome of Dbait32Hc (SEQ ID NO: 6) as compared to Dbait32H (SEQ ID NO: 1). It shows also that the single strand Dbaut32ss was inactive even at high dose.

It should be pointed out that the Dbait32Hc (SEQ ID NO: 6) is devoid of CpG in its sequence in order to avoid the effect of immunological reaction due to well known Toll-like receptor-mediated immunostimulations.

In conclusion, the significant reduction in tumor growth of human radio-resistant tumors (IHep2, U87 and SK28) and radio-sensitive tumor (LU1205) xenografted on nude mice provides evidence that the Dbait molecules can efficiently radiosensitize the effect of radiotherapy on these aggressive tumors. Thus, proof of concept of DNA bait approach has been achieved in vivo.

Example 6

Chemosensitization of the Treatment of Digestive Tumors Induced in K-Ras$^{V12G}$×Apc$^{1638N}$ Transgenic Mice An endogenous mouse tumor model was chosen to assess the ability of Dbait molecules to sensitize anticancer chemotherapy. To this end, transgenic mice carrying K-Ras$^{V12G}$ and Apc$^{1638N}$ mutations were used. They were obtained by breeding two transgenic mice: one carries K-Ras$^{V12G}$ mutant under the control of the mouse villin promoter (pVill/K-Ras$^{V12G}$) (Janssen et al., 2002), the other contains Apc$^{1638N}$ mutation in one allele (Fodde et al., 1994). Transgenic mice with pVill/K-Ras$^{V12G}$×Apc$^{1638N}$ mutations developed spontaneous tumors in the digestive tract at the age of about 5 months and died rapidly.

They were treated at the mean age of 12 weeks by a combination of chemotherapy (5FU+CPT11) and of Dbait32H (SEQ ID NO: 1) versus chemotherapy alone, according to the protocol shown in FIG. 5.1 panel A. The protocol includes three treatment cycles.

Each cycle consists of intraperitoneal injection of 0.6 mg 5FU and 0.6 mg CPT11, along with 0.1 mg Dbait32H (SEQ ID NO: 1) by oral administration, three times a week, followed by one week rest.

5FU (5 fluorouracile, Teva) was prepared in 0.9% NaCl solution at the concentration of 50 mg/ml. CPT11/irinotecan (Campto, Aventis) was prepared in 0.9% NaCl solution at the concentration of 20 mg/ml. The health status and survival of the mice were monitored till the death. No clinical indication of additional toxic effect due to Dbait molecules was observed.

The results are shown on FIG. 5.1. Panel A: Treatment protocol for three groups/arms of the K-Ras$^{V12G}$×Apc$^{1638N}$ transgenic mice at the mean age of 12 weeks: the control group (untreated), the group treated by 5FU+CPT11, the group treated by 5FU+CPT11 and Dbait32H (SEQ ID NO: 1). It was performed by three cycles of treatment. Each cycle consists of intraperitoneal injection of 0.6 mg 5FU and 0.6 mg CPT11, along with 0.1 mg Dbait32H (SEQ ID NO: 1) by oral administration, three times a week, followed by one week rest. The number of mice involved in each groups is indicated in parenthesis. The end point is the time of survival; Panel B: Kaplan-Meier plot of survival curves of the three. groups; Panel C: The median survival time of three groups as shown in panel B.

Despite reduced cohort, an improvement of survival time was observed in the arm which received the combination of chemotherapy (5FU+11CPT) and Dbait32H (SEQ ID NO: 1) (median survival=226 days, p-value=0.2), as compared to that of chemotherapy alone (173 days) and control arm (175 days) (panel B and C).

Additional assays are currently underway to increase the cohort of 5FU+CPT11+Dbait32H (SEQ ID NO: 1) and 5FU+CPT11 arms, in order to enhance statistical significance.

A series of mice was sacrificed two weeks after the end of treatment (at the mean age of 18 weeks) in order to evaluate the mean number of tumors per animal. The intestine was examined by macroscopy and histology examination (standard staining by Hematoxyline-Eosine-Safran).

The results are given on FIG. 5.2. The number of animals in each group was indicated in parenthesis. All mice were sacrificed two weeks (week 18) after the protocol shown in FIG. 5.1 panel A. The mean number of the control arm (untreated group, n=101) is 30.8/animal.

Both examinations consistently showed a significant reduction of tumor numbers (>30%) in the arm which received the combination of 5FU+CPT11 and Dbait32H (SEQ ID NO: 1) (n=8) as compared to the arm which received chemotherapy alone (n=7) (FIG. 5.2). It is worthy to note that the mean number of the control arm (untreated group, n=101) is 30.8/animal.

Tumor samples prepared from animals treated with Dbait molecules tagged by fluorescein (Dbait32H-FITC) (SEQ ID NO: 1) and 5FU+CPT11 were analysed using immunofluorescence staining methods. γ-H2AX labeled foci were costained with fluorescent Dbait molecules, in reminiscence of the in vitro finding (cf. example 3.3 and 4). FIG. 5.3 shows an additional assay where a 18 week-old K-Ras$^{V12G}$×Apc$^{1638N}$ transgenic mouse was consecutively treated by chemotherapy (5FU+CPT11) and Dbait32H-FITC (SEQ ID NO: 1) for three days and sacrificed two hours later after the last treatment as indicated in the panel A. The intestine was taken out and washed by PBS. Then the tumor tissues were sampled and frozen at −80° C. For the analysis, 5 µm histological samples were made from the frozen tumor tissues by cryostat. DNA repair foci were detected by immunofluorescence with polyclonal rabbit anti-γ-H2AX antibody (Trevigen) diluted 1/500 in PBS, then with goat anti-rabbit antibody tagged by cyanine 3 (Jackson) diluted 1/200 in PBS. The samples were also counterstained by DAPI Samples were visualized by epifluorescence microscopy. It was found that the fluorescence of Dbait32H-FITC (SEQ ID NO: 1) was heterogeneously disseminated in tumor tissues (epithelium and stroma between. glandular structures) and had preferential nucleus localization (FIG. 5.3, panel B, left). Similar pattern was found for γ-H2AX sites (FIG. 5.3, panel B, right). The co-localized Dbait32H-FITC (SEQ ID NO: 1) and γ-H2AX signals were almost observed.

In conclusion, the improvement of survival and the reduction of tumor number per animal consistently show the evidence of chemosensitization of the treatment of digestive tumors in the transgenic mice carrying K-Ras$^{V12G}$×Apc$^{1638N}$ mutations by Dbait molecules (Dbait32H (SEQ ID NO: 1)). In-depth analysis of tumor tissues in treated animals provides evidence that Dbait molecules interfere with DNA repair process.

It should be pointed out that the oral administration of Dbait32H (SEQ ID NO: 1) molecules dID NO:t include any transfection agent in this study.

To sum up, biochemical and in vitro data are clearly consistent with a mechanism of action of Dbait molecules through interference with DSB repair by NHEJ pathway, and the repair signal transduction pathway caused by direct or indirect DNA damage (ionizing radiation or chemotherapeutic agents). Due to the nature of the sequence-independent, NHEJ pathway (Jackson, 2002; Barnes, 2001; Downs & Jackon, 2004), there is no limitation on the sequences and the length of Dbait molecules beyond a minimal length (about 32-bp). In vivo studies have confirmed efficient radio- and chemo-sensitization of tumors in mice by Dbait molecules. Taken together, all data have consistently provided with proofs of concept of the DNA Bait approach, characterized the molecular features of Dbait molecules.

REFERENCES

Barnes, D. E. Non-homologous end joining as a mechanism of DNA repair. Curr. Biol. (2001)11, R455-7.

Belenkov A I, Paiement J P, Panasci L C, Monia B P, Chow T Y. An antisense oligonucleotide targeted to human Ku80 messenger RNA sensitizes M059K malignant glioma cells to ionizing radiation, bleomycin, and etoposide but not DNA cross-linking agents. Cancer Res. (2002), 62, 5888-96.

Bouton., S.: Kyle. S.: Durkacz. B. W. Mechanisms of enhancement of cytotoxicity in etoposide and ionising radiation-treated cells by the protein kinase inhibitor wortmannin. Eur. J Cancer (2000), 36, 535-41.

Cantor, C. R.; Warshaw, M. M.; Shapiro, H. Oligonucleotide interactions. III. Conformational differences between deoxy- and ribodinucleoside phosphates Biopolymers (1970), 9, 1059-77.

Cary, R. B.; Peterson, S. R.; Wang, J. T.; Bear, D. G.; Bradbury, E. M. & Chen, D. J. DNA looping by Ku and the DNA-dependent protein kinase. Proc. Natl. Acad. Sci. USA (1997) 94, 4267-4272.

Downs, J. A.; Jackson, S. P A means to a DNA end: The many roles of Ku. Nat. Rev. Mol. Cell. Biol. (2004), 5, 367-78.

Durant, S.; Karran, P. Vanillins—a novel family of DNA-PK inhibitors. Nucleic Acids Res. (2003), 31, 5501-12.

Fodde, R.; Edelmann, W.; Yang, K.; van Leeuwen, C.; Carlson, C.; Renault, B.; Breukel, C.; Alt, E.; Lipkin, M.; Khan, P. M. A targeted chain-termination mutation in the mouse Ape gene results in multiple intestinal tumors. Proc Natl Acad Sci USA. (1994), 91, 8969-73.

Jackson, S. P. Sensing and repairing DNA double-strand breaks. Carcinogenesis. (2002), 23, 687-96.

Janssen, K. P.; el-Marjou, F.; Pinto, D.; Sastre, X.; Rouillard, D.; Fouquet, C.; Soussi, T.; Louvard, D.; Robine, S. Targeted expression of oncogenic K-ras in intestinal epithelium causes spontaneoustumorigenesis in mice. Gastroenterology (2002), 123, 492-504.

Kim, C. H.; Park, S. J.; Lee, S. H.; A targeted inhibition of DNA-dependent protein kinase sensitizes breast cancer cells following ionizing radiation. J; Pharmacol. Exp. Ther. (2002), 303, 753-9.

Lee, H.; Sun, D.; Larner, J. M.; Wu, F. S. The tumor suppressor p53 can reduce stable transfection in the presence of irradiation. J Biomed. Sci. (1999), 6, 285-92.

Li, S.; Takeda, Y.; Wragg, S.; Barrett, J.; Phillips, A.; Dynan, W. S. Modification of the ionizing radiation response in living cells by an scFv against the DNA-dependent protein kinase. Nucleic Acid Res. (2003) 31, 5848-57.

Li, G. C.; He, F.; Shao, X.; Urano, M.; Shen, L.; Kim, D.; Borrelli, M.; Leibel, S. A.; Gutin, P. H.; Ling, C. C. Adenovirus-mediated heat-activated antisense Ku70 expression radiosensitizes tumor cells in vitro and in vivo. Cancer Res. (2003b), 63, 3268-74.

Maacke, H.; Jost, K.; Opitz, S.; Miska, S.; Yuan, Y.; Hasselbach, L.; Luttges, J.; Kalthoff, H.; Sturzbecher, H. W. DNA repair and recombination factor Rad51 is over-expressed in human pancreaticadenocarcinoma. Oncogene (2000). 19, 2791-5.

Mallya, S. M., Sikpi, M. O. Evidence of the involvement of p53 in gamma-radiation-induced DNA repair in human lymphoblasts. vint. J Radiat. Biol. (1998), 74, 231-8.

Marangoni, E.; Bay, J. O.; Verrelle, P.; Bourhis, J. Tranfert de gène pour modifier la réponse à la radiotherapie Cancer Radiother. (2000), 4, 175-80.

Marangoni, E.; Foray, N.; O'Driscoll, M.; Douc-Rasy, S.; Bernier, J.; Bourhis, J.; Jeggo, P. A Ku80 fragment with dominant negative activity imparts a radiosensitive phenotype to CHO-K1 cells. Nucleic Acid Res. (2000a), 28, 4778-82.

Marangoni, E.; Le Romancer, M.; Foray, N.; Muller, C.; Douc-Rasy, S.; Vaganay, S.; Abdulkarim, B.; Barrois, M.; Calsou, P.; Bernier, J.; Salles, B.; Bourhis J. Transfer of Ku80 RNA antisense decreases the radioresistance of human fibroblasts. Cancer Gene Ther. (2000b), 7, 339-46.

Martensson, S.; Hammarsten, O. DNA-dependent protein kinase catalytic subunit: structural requirements for kinase activity by DNA ends, J Biol. Che77i. (2002), 277, 3020-29.

Mimori, T.; Hardin, J. A. Mechanism of interaction between Ku protein and DNA. J Biol. Chem. (1986), 261, 10375-10379.

Nimura, Y.; Ismail, S. M.; Kurimas, A.; Chen, D. J.; Stevens, C. W. DNA-PK and ATM are required for radiation-enhanced integration. Radiat Res. (2002), 157, 562-7.

O'Driscoll, M.; Jeggo, P. Immunological disorders and DNA repair. Mutat Res. (2002), 509, 109-26.

Ohnishi, T.; Taki, T.; Hiraga, S.; Arita, N.; Morita, T. In vitro and in vivo potentiation of radiosensitivity of malignant gliomas by antisense inhibition of the RAD51 gene. Biochem Biophys Res Commun. (1998), 245, 319-24.

Pang, D. L.; Yoo, S. H.; Dynan, W. S.; Jung, M.; Dritschilo, A. Ku proteins join DNA fragments as shown by atomic force microscopy. Cancer Res. (1997), 57, 1412-5.

Peng, Y.; Zhang, Q.; Nagasawa, H.; Okayasu, R.; Liber, H. L.; Bedford, J. S. Silencing expression of the catalytic subunit of DNA-dependent protein kinase by small interfering RNA sensitizes human cells for radiation-induced chromosome damage, cell killing, and mutation. Cancer Res. (2002), 62, 6400-4.

Rassool, F. V. DNA double strand breaks (DSB) and non-homologous end joining (NHEJ) pathways in human leukemia. Cancer Lett. (2003), 193, 1-9.

Roddam, P. L.; Rollinson, S.; O'Driscoll, M.; Jeggo, P. A.; Jack, A.; Morgan, G. J. Genetic variants of NHEJ DNA ligase IV can affect the risk of developing multiple myeloma, a tumour characterised by aberrant class switch recombination. J: Med. Genet. (2002) 39, 900-5.

Sak, A.; Stuschke, M.; Wurm, R.; Schroeder, G.; Sinn, B.; Wolf, G.; Budach, V. Selective inactivation of DNA-dependent protein kinase with antisense oligodeoxynucleotides: consequences for the rejoining of radiation-induced DNA double-strand breaks and radiosensitivity of human cancer cell lines. Cancer Res. (2002), 62, 6621-24.

Stevens, C. W.; Zeng, M.; Cerniglia, G. J. Ionizing radiation greatly improves gene transfer efficiency in mammalian cells. Hure Gene Ther. (1996), 7, 1727-34.

Stevens, C. W.; Stamato, T. D., Mauldin, S. K.; Getts, R. C.; Zeng, M.; Cerniglia, G. J. Radiation-induced recombination is dependent on KU80. Radiat Res. (1999), 151, 408-13.

Stevens, C. W.; Cerniglia, G. J.; Giandomenico, A. R.; Koch, C. J. DNA damaging agents improve stable gene transfer efficiency in mammalian cells. Radiat Oncollnvestig. (1998), 6, 1-9.

Verrelle, P.; Bourhis, J. Modulation de la réponse cellulaire aux radiations ionisantes: vers de nouvelles cibles moléculaires. Cancer Radiother. (1997), 1, 484-93.

Walker, J. R.; Corpina, R. A.; Goldberg, J. Structure of the Ku heterodimer bound to DNA and its implications for double-strand break repair. Nature (2001), 412, 607-14.

Yoo, S. H.; Dynan, W. S. Characterization of the RNA binding properties of Ku protein. Biochemistry (1998), 37, 1336-43.

Yoo, S. H.; Kimzey, A.; Dynan, W. S. Photocross-linking of an oriented DNA repair complex. Ku bound at a single DNA end. J. Biol. Chem. (1999), 274, 20034-9.

Yoo, S. H.; Dynan, W. S. Geometry of a complex formed by double strand break repair proteins at a single DNA end: recruitment of DNA-PKcs induces inward translocation of Ku protein. Nucleic Acid Res. (1999), 27, 4679-86.

Zhao, J. K.; Wang, J. T.; Chen, D. J.; Peterson, S. R.; Trewhella, J. The solution structure of the DNA double-stranded break repair protein Ku and its complex with DNA: a neutron contrast variation study. Biochemistry (1999), 3, 2152-9.

SEQUENCE LISTING

```
<160> NUMBER OF SEQ ID NOS: 9

<210> SEQ ID NO 1
<211> LENGTH: 32
<212> TYPE: DNA
<213> ORGANISM: artificial sequence
<220> FEATURE:
<223> OTHER INFORMATION: Dbait32, Dbait32H-po, Dbait32H, Dbait32ss,
      Dbait32-T4, Dbait32C, Dbait32NH2, Dbait32H-FITC, Dbait32H-Cy3,
      Dbait32H-Biot
<220> FEATURE:
<221> NAME/KEY: misc_feature
<222> LOCATION: (1)..(32)
<223> OTHER INFORMATION: Dbait32 : double stranded DNA with the three
      last nucleotides at the 5' and 3' ends of both strands with
      phosphorothioate backbone
<220> FEATURE:
<221> NAME/KEY: misc_feature
<222> LOCATION: (1)..(32)
<223> OTHER INFORMATION: Dbait32ss : single stranded DNA with the three
      last nucleotides at the 5' and 3' ends with phosphorothioate
      backbone
<220> FEATURE:
<221> NAME/KEY: misc_feature
<222> LOCATION: (1)..(32)
<223> OTHER INFORMATION: Dbait32-T4 : stem (1)..(32), a loop at (32) is
      a four thymines linker, the first three nucleotides at 5' end of
      the + strand and the last three nucleotides at 3' end of the -
      strand with phosphorothioate backbone
<220> FEATURE:
<221> NAME/KEY: misc_feature
<222> LOCATION: (1)..(32)
<223> OTHER INFORMATION: Dbait32H-po : stem (1)..(32) and a loop at (32)
      is hexaethyleneglycol linker
<220> FEATURE:
```

```
<221> NAME/KEY: misc_feature
<222> LOCATION: (1)..(32)
<223> OTHER INFORMATION: Dbait32H : stem (1)..(32), a loop at (32) is
      hexaethyleneglycol linker, the first three nucleotides at 5' end
      of + strand and the last three nucleotides at 3' end of the -
      strand with phosphorothioate backbone
<220> FEATURE:
<221> NAME/KEY: misc_feature
<222> LOCATION: (1)..(32)
<223> OTHER INFORMATION: Dbait32C : stem (1)..(32), two loops at (1) and
      (32) are hexaethyleneglycol linkers
<220> FEATURE:
<221> NAME/KEY: misc_feature
<222> LOCATION: (1)..(32)
<223> OTHER INFORMATION: Dbait32NH2 : ds DNA with the first three
      nucleotides at 5' end of the + strand and the last three
      nucleotides at 3' end of the - strand with phosphorothioate
      backbone, and a NH2 group at the 3' end of the + strand and at the
      5' end of the - strand
<220> FEATURE:
<221> NAME/KEY: misc_feature
<222> LOCATION: (1)..(32)
<223> OTHER INFORMATION: Dbait32H-FITC: stem (1)..(32), a loop at (32)
      is hexaethyleneglycol linker, the first 3 nucleotides at 5' end of
      + strand and the last 3 nucleotides at 3' end of the - strand with
      phosphorothioate backbone, FITC bound to nt (32) of the + strand
<220> FEATURE:
<221> NAME/KEY: misc_feature
<222> LOCATION: (1)..(32)
<223> OTHER INFORMATION: Dbait32H-Cy3: stem (1)..(32), a loop at (32) is
      hexaethyleneglycol linker, the first 3 nucleotides at 5' end of +
      strand and the last 3 nucleotides at 3' end of the - strand with
      phosphorothioate backbone, cy3 bound to nt (32) of the + strand
<220> FEATURE:
<221> NAME/KEY: misc_feature
<222> LOCATION: (1)..(32)
<223> OTHER INFORMATION: Dbait32H-Biot: stem (1)..(32), a loop at (32)
      is hexaethyleneglycol linker, the first 3 nucleotides at 5' end of
      + strand and the last 3 nucleotides at 3' end of the - strand with
      phosphorothioate backbone, Biot bound to nt (32) of the + strand

<400> SEQUENCE: 1
acgcacgggt gttgggtcgt ttgttcggat ct                                    32

<210> SEQ ID NO 2
<211> LENGTH: 24
<212> TYPE: DNA
<213> ORGANISM: artificial sequence
<220> FEATURE:
<223> OTHER INFORMATION: Dbait24H
<220> FEATURE:
<221> NAME/KEY: misc_feature
<222> LOCATION: (1)..(24)
<223> OTHER INFORMATION: stem (1)..(24), a loop at (24) is
      hexaethyleneglycol linker, the first three nucleotides at 5' end
      of + strand and the last three nucleotides at 3' end of the -
      strand with phosphorothioate backbone

<400> SEQUENCE: 2
acgcacgggt gttgggtcgt ttgt                                             24

<210> SEQ ID NO 3
<211> LENGTH: 16
<212> TYPE: DNA
<213> ORGANISM: artificial sequence
<220> FEATURE:
<223> OTHER INFORMATION: Dbait16H
<220> FEATURE:
<221> NAME/KEY: misc_feature
<222> LOCATION: (1)..(16)
<223> OTHER INFORMATION: stem (1)..(16), a loop at (16) is
      hexaethyleneglycol linker, the first three nucleotides at 5' end
      of + strand and the last three nucleotides at 3' end of the -
      strand with phosphorothioate backbone
```

-continued

```
<400> SEQUENCE: 3
acgcacgggt gttggg                                                          16

<210> SEQ ID NO 4
<211> LENGTH: 8
<212> TYPE: DNA
<213> ORGANISM: artificial sequence
<220> FEATURE:
<223> OTHER INFORMATION: Dbait8H
<220> FEATURE:
<221> NAME/KEY: misc_feature
<222> LOCATION: (1)..(8)
<223> OTHER INFORMATION: stem (1)..(8), a loop at (8) is
      hexaethyleneglycol linker, the first three nucleotides at 5' end
      of + strand and the last three nucleotides at 3' end of the -
      strand with phosphorothioate backbone

<400> SEQUENCE: 4 acgcacgg                                                                    8

<210> SEQ ID NO 5
<211> LENGTH: 32
<212> TYPE: DNA
<213> ORGANISM: artificial sequence
<220> FEATURE:
<223> OTHER INFORMATION: Dbait32Hb,DBait32Hc-5'5'
<220> FEATURE:
<221> NAME/KEY: misc_feature
<222> LOCATION: (1)..(32)
<223> OTHER INFORMATION: Dbait32Hb : stem (1)..(32), a loop at (32) is
      hexaethyleneglycol linker, the first three nucleotides at 5' end
      of + strand and the last three nucleotides at 3' end of the -
      strand with phosphorothioate backbone
<220> FEATURE:
<221> NAME/KEY: misc_feature
<222> LOCATION: (1)..(32)
<223> OTHER INFORMATION: Dbait32Hc5'5' : stem (1)..(32), a loop at (32)
      is hexaethyleneglycol linker, the first 3 nt at 5' end of + strand
      and the last 3 nt at 3' end of - strand with phosphorothioate
      backbone, the last nt at the 3' end of - strand with 3'-3' linkage

<400> SEQUENCE: 5
gctaggcttg tttgctgggt tgtaggcaca gc                                        32

<210> SEQ ID NO 6
<211> LENGTH: 32
<212> TYPE: DNA
<213> ORGANISM: artificial sequence
<220> FEATURE:
<223> OTHER INFORMATION: Dbait32Ha, Dbait32Hc, Dbait32Hc-3'mp,
      Dbait32Hc-5'3'mp, Dbait32Hcss-po, Dbait32Hc-Cy3, Dbait32Hc-Cy5
<220> FEATURE:
<221> NAME/KEY: misc_feature
<222> LOCATION: (1)..(32)
<223> OTHER INFORMATION: Dbait32Ha : stem (1)..(32), a loop at (32) is
      hexaethyleneglycol linker, the first three nucleotides at 5' end
      of + strand and the last three nucleotides at 3' end of the -
      strand with phosphorothioate backbone
<220> FEATURE:
<221> NAME/KEY: misc_feature
<222> LOCATION: (1)..(32)
<223> OTHER INFORMATION: Dbait32Hc : stem (1)..(32), a loop at (32) is
      hexaethyleneglycol linker, the first three nucleotides at 5' end
      of + strand and the last three nucleotides at 3' end of the -
      strand with phosphorothioate backbone
<220> FEATURE:
<221> NAME/KEY: misc_feature
<222> LOCATION: (1)..(32)
<223> OTHER INFORMATION: Dbait32Hc-3'mp : stem (1)..(32), a loop at (32)
      is hexaethyleneglycol linker, the last three nucleotides at 3' end
      of the - strand with methylphosphonate backbone
<220> FEATURE:
<221> NAME/KEY: misc_feature
```

```
<222> LOCATION: (1)..(32)
<223> OTHER INFORMATION: Dbait32Hc-5'3'mp : stem (1)..(32), a loop at
      (32) is hexaethyleneglycol linker, the first three nucleotides at
      5' end of + strand and the last three nucleotides at 3' end of the
      - strand with methylphosphonate backbone
<220> FEATURE:
<221> NAME/KEY: misc_feature
<222> LOCATION: (1)..(32)
<223> OTHER INFORMATION: Dbait32Hcss-po : single strand DNA
<220> FEATURE:
<221> NAME/KEY: misc_feature
<222> LOCATION: (1)..(32)
<223> OTHER INFORMATION: Dbait32Hc-Cy3 : stem (1)..(32), a loop at (32)
      is hexaethyleneglycol linker, the first 3 nucleotides at 5' end of
      + strand and the last 3 nucleotides at 3' end of the - strand with
      phosphorothioate backbone, cy3 bound to nt (31) of the - strand
<220> FEATURE:
<221> NAME/KEY: misc_feature
<222> LOCATION: (1)..(32)
<223> OTHER INFORMATION: Dbait32Hc-Cy5 : stem (1)..(32), a loop at (32)
      is hexaethyleneglycol linker, the first 3 nucleotides at 5' end of
      + strand and the last 3 nucleotides at 3' end of the - strand with
      phosphorothioate backbone, cy5 bound to nt (31) of the - strand

<400> SEQUENCE: 6
gctgtgccca cacccagca aacaagccta ga                                  32

<210> SEQ ID NO 7
<211> LENGTH: 32
<212> TYPE: DNA
<213> ORGANISM: artificial sequence
<220> FEATURE:
<223> OTHER INFORMATION: Dbait32Hd, Dbait32Hd-FITC
<220> FEATURE:
<221> NAME/KEY: misc_feature
<222> LOCATION: (1)..(32)
<223> OTHER INFORMATION: Dbait32Hd : stem (1)..(32), a loop at (32) is
      hexaethyleneglycol linker, the first three nucleotides at 5' end
      of + strand and the last three nucleotides at 3' end of the -
      strand with phosphorothioate backbone
<220> FEATURE:
<221> NAME/KEY: misc_feature
<222> LOCATION: (1)..(32)
<223> OTHER INFORMATION: Dbait32Hd-FITC : stem (1)..(32), a loop at (32)
      is hexaethyleneglycol linker, the first 3 nucleotides at 5' end of
      + strand and the last 3 nucleotides at 3' end of the - strand with
      phosphorothioate backbone, FITC bound to nt (31) of the - strand

<400> SEQUENCE: 7
gctaggtctg tttggtggct ttgcagtggc ac                                 32

<210> SEQ ID NO 8
<211> LENGTH: 8
<212> TYPE: DNA
<213> ORGANISM: artificial sequence
<220> FEATURE:
<223> OTHER INFORMATION: Dbait8Hc-Cy3
<220> FEATURE:
<221> NAME/KEY: misc_feature
<222> LOCATION: (1)..(8)
<223> OTHER INFORMATION: stem (1)..(8), a loop at (8) is
      hexaethyleneglycol linker, the first three nucleotides at 5' end
      of + strand and the last three nucleotides at 3' end of the -
      strand with phosphorothioate backbone, Cyanin3 bound to nucleotide
      (8) of of the - strand

<400> SEQUENCE: 8 gctgtgca                                                             8

<210> SEQ ID NO 9
<211> LENGTH: 64
<212> TYPE: DNA
<213> ORGANISM: artificial sequence
```

-continued

```
<220> FEATURE:
<223> OTHER INFORMATION: Dbait64 and Dbait64L
<220> FEATURE:
<221> NAME/KEY: misc_feature
<222> LOCATION: (1)..(64)
<223> OTHER INFORMATION: Dbait64 : double stranded DNA with the three
      last nucleotides at the 5' and 3' ends of both strands with
      phosphorothioate backbone
<220> FEATURE:
<221> NAME/KEY: misc_feature
<222> LOCATION: (1)..(64)
<223> OTHER INFORMATION: Dbait64L : double stranded DNA with the three
      last nucleotides at the 5' and 3' ends of both strands with
      phosphorothioate backbone, and an hexaethyleneglycol linker
      introduced between nucleotides (32) and (33) of both strands

<400> SEQUENCE: 9
acgcacgggt gttgggtcgt tgttcggat ctacgcacgg tcgtttgttc ggtgttggcg      60
atct                                                                  64
```

The invention claimed is:

1. A nucleic acid molecule, wherein said molecule comprises a double stranded portion with the sequence of SEQ ID NO:5, has at least one free end, and wherein said molecule is substrate for binding by at least a Ku protein involved in the Non-Homologous End-Joining (NHEJ) pathway of double strand breaks (DSB) repair.

2. The molecule of claim 1, wherein said molecule comprises between 16 and 200 bp.

3. The molecule of claim 1, wherein said molecule is a linear or a hairpin nucleic acid molecule.

4. The molecule of claim 3, wherein said molecule is a hairpin nucleic acid molecule and wherein the loop comprises nucleic acid or chemical groups.

5. The molecule of claim 1, wherein the free end is blunt or 5'- or 3'-protruding.

6. The molecule of claim 1, wherein said molecule binds in vitro a Ku complex comprising at least Ku70 or Ku80.

7. The molecule of claim 1, wherein said molecule binds in vitro a Ku complex comprising at least a DNA-PKc protein.

8. The molecule of claim 1, wherein said molecule is capable of being up-taken by cell into the cell nucleus.

9. The molecule of claim 1, wherein said molecule comprises a phosphodiester backbone or a chemically modified phosphodiester backbone, or another backbone with one or several chemical groups.

10. The molecule of claim 1, wherein said molecule comprises a 2'-deoxynucleotide backbone, and optionally comprises one or several modified nucleotides and/or nucleobases other than adenine, cytosine, guanine and thymine.

11. The molecule of claim 9, wherein said molecule comprises a backbone comprising methylphosphonates, phosphoramidates, morpholino nucleic acid, 2'-O,4'-Cmethylene/ethylene bridged locked nucleic acid, peptide nucleic acid (PNA), short chain alkyl, or cycloalkyl intersugar linkages or short chain heteroatomic or heterocyclic intrasugar linkages of variable length.

12. The molecule of claim 9, further comprising sugar mimetics in place of the pentofuranosyl group.

13. The molecule of claim 1, comprising one or several chemical groups at the end of each strand or, at least, at the 3' end of each strand.

14. The molecule of claim 13, comprising one or several phosphorothioates at the end of each strand or, at least, at the 3' end of each strand.

15. A molecule selected from Dbait32Hb (SEQ ID NO:5), and Dbait32Hc-5'5' (SEQ ID NO:5).

16. A method of enhancing tumor sensitivity to DNA damaging anticancer therapy, the method comprising administering to a subject a molecule of claim 1.

17. A method of treating cancer, the method comprising administering to a subject a molecule of claim 1 in combination with a DNA damaging anticancer therapy.

18. The method of claim 16, wherein the DNA damaging anticancer therapy is selected from radiotherapy and chemotherapy.

19. The method of claim 18, wherein the molecule is administered prior to radiotherapy.

20. The method of claim 18, wherein the molecule is administered prior to or along with chemotherapy.

21. The method of claim 16, wherein the cancer is selected from glioblastoma, head and neck, colon, liver, lung, skin, breast cancer and cervical cancer.

22. The method of claim 16, wherein the molecule is administered by intravenous, intra-tumoral or sub-cutaneous injection, intracranial or intra artery injection or infusion, or by oral route.

23. A composition for use in association with a DNA breaking treatment, particularly radiotherapy or chemotherapy, said composition comprising at least one molecule of claim 1 in combination with a pharmaceutically acceptable carrier, in an efficient amount for introduction into the nucleus of tumor cells.

* * * * *